(12) United States Patent
Tsujii et al.

(10) Patent No.: US 7,380,443 B2
(45) Date of Patent: Jun. 3, 2008

(54) HARDNESS TESTING APPARATUS

(75) Inventors: Masaharu Tsujii, Yamato (JP);
Fumihiko Koshimizu, Zama (JP); Eiji Furuta, Sagamihara (JP); Ryouji Nakamura, Ayase (JP); Satoko Nomaguchi, Sagamihara (JP); Ryotaro Fukuchi, Hikone (JP)

(73) Assignee: Mitutoyo Corporation, Kawasaki (JP)

( * ) Notice: Subject to any disclaimer, the term of this patent is extended or adjusted under 35 U.S.C. 154(b) by 0 days.

(21) Appl. No.: 11/512,169

(22) Filed: Aug. 30, 2006

(65) Prior Publication Data

US 2006/0288763 A1    Dec. 28, 2006

Related U.S. Application Data

(62) Division of application No. 10/744,813, filed on Dec. 24, 2003, now Pat. No. 7,121,136.

(30) Foreign Application Priority Data

| Dec. 25, 2002 | (JP) | ............................. | 2002-374670 |
| Jan. 27, 2003 | (JP) | ............................. | 2003-017427 |
| Feb. 19, 2003 | (JP) | ............................. | 2003-041062 |
| Aug. 22, 2003 | (JP) | ............................. | 2003-298764 |
| Oct. 9, 2003 | (JP) | ............................. | 2003-350747 |
| Oct. 9, 2003 | (JP) | ............................. | 2003-350796 |
| Oct. 22, 2003 | (JP) | ............................. | 2003-361881 |

(51) Int. Cl.
*G01N 3/40* (2006.01)
*G01N 3/42* (2006.01)

(52) U.S. Cl. ................................. 73/81; 73/83; 73/85

(58) Field of Classification Search ............... 73/12.09, 73/12.12, 14, 81, 82, 83, 85, 104, 760, 763, 73/769, 774, 778, 788, 818, 821
See application file for complete search history.

(56) References Cited

U.S. PATENT DOCUMENTS 3,564,908 A * 2/1971 Fischer .......................... 73/81
3,653,256 A * 4/1972 Mashimo ....................... 73/81

(Continued)

FOREIGN PATENT DOCUMENTS

EP    1 030 171 A2    8/2000

(Continued)

OTHER PUBLICATIONS

"Hardness Testing Machines Catalog", Mitutoyo, pp. 10 and 49.*

(Continued)

*Primary Examiner*—Hezron E. Williams
*Assistant Examiner*—David A. Rogers
(74) *Attorney, Agent, or Firm*—Oliff & Berridge, PLC

(57) ABSTRACT

A hardness testing apparatus has an indenter shaft having an indenter at a top thereof, a force motor for moving the indenter shaft in its axial direction and applying a predetermined test force to a sample through the indenter, an external force detection section for detecting an external force applied from outside of the hardness testing apparatus to the indenter shaft when the indenter shaft is moved by the force motor, and an external force adjustment and control section for controlling the force motor to apply the predetermined test force to the sample while deadening the external force detected by the external force detection section.

6 Claims, 24 Drawing Sheets

U.S. PATENT DOCUMENTS

| | | | |
|---|---|---|---|
| 4,104,901 A * | 8/1978 | Sidaway .................. | 73/81 |
| 4,255,966 A * | 3/1981 | Batie et al. .............. | 73/81 |
| 4,435,976 A | 3/1984 | Edward, Jr. | |
| 4,463,600 A * | 8/1984 | Hobbs et al. ............ | 73/81 |
| 4,627,096 A * | 12/1986 | Grattoni et al. .......... | 382/141 |
| 4,653,106 A * | 3/1987 | Yamatsuta et al. ....... | 382/141 |
| 4,841,764 A | 6/1989 | Fischer | |
| 4,848,141 A | 7/1989 | Oliver et al. | |
| 5,067,346 A | 11/1991 | Field | |
| 5,146,779 A * | 9/1992 | Sugimoto et al. ........ | 73/81 |
| 5,284,049 A * | 2/1994 | Fukumoto ................. | 73/82 |
| 5,309,754 A | 5/1994 | Ernst | |
| 6,142,010 A | 11/2000 | Merck, Jr. et al. | |
| 6,755,075 B2 * | 6/2004 | Nagashima et al. ...... | 73/105 |
| 2003/0140684 A1 | 7/2003 | Broz et al. | |
| 2004/0011119 A1 | 1/2004 | Jardret et al. | |

FOREIGN PATENT DOCUMENTS

| | | |
|---|---|---|
| JP | A 57172232 | 10/1982 |
| JP | A 02-290530 | 11/1990 |
| JP | A 07-049297 | 2/1995 |
| JP | A 09-095930 | 4/1997 |
| JP | A 09-145580 | 6/1997 |
| JP | A 60256030 | 2/1998 |
| JP | A 10-132722 | 5/1998 |
| JP | A 11-037915 | 2/1999 |
| JP | A 2000-105182 | 4/2000 |
| JP | 2000-146793 A | 5/2000 |
| JP | A 2000-292333 | 10/2000 |
| JP | A 2001-133376 | 5/2001 |
| JP | A 2001-296225 | 10/2001 |
| JP | A 2003-161684 | 6/2003 |
| WO | WO 98/08073 | 2/1998 |

OTHER PUBLICATIONS

VanLandingham, M., "Review of Instrumented Indentation", Journal of Research of the National Institute of Standards and Technology, Jul.-Aug. 2003, vol. 108, No. 4, pp. 249-265.

Olson et al., "Stiffness Measurement of the External Polymeric Coating of an Optical Fiber", Experimental Techniques, Nov.-Dec. 2002, pp. 51-56.

Asif et al., "Nanoindentation and Contact Stiffness Measurement Using Force Modulation with a Capacitive Load-Displacement Transducer", Review of Scientific Instruments, May 1999, pp. 1-6.

* cited by examiner

602(603)

HARDNESS TESTING APPARATUS

CROSS-REFERENCE TO RELATED APPLICATION

This is a Division of application Ser. No. 10/744,813 filed Dec. 24, 2003. The disclosure of the prior application is hereby incorporated by reference herein in its entirety.

BACKGROUND

The present invention relates to a hardness testing apparatus in which a hardness of a sample is measured by forming a dimple on the surface of the sample.

In a first earlier development, a hardness testing apparatus is used. In this apparatus, a load is applied to the surface of a sample by an indenter to form a dimple on the surface of the sample, and a hardness of the sample is measured.

For example, a hardness testing apparatus 500 shown in FIG. 25 is known (for example, refer to FIG. 2 of Published Japanese Patent Application (Tokkaihei) No. H10-132722).

As shown in FIG. 25, the hardness testing apparatus 500 has an indenter shaft unit 510 having an indenter shaft 502 and a load applying mechanism 530 for applying a predetermined load to the indenter shaft 502. An indenter 501 is arranged on the top of the indenter shaft 502 to form a dimple in a sample S mounted on a sample stand 555.

The indenter shaft unit 510 is placed above the sample stand 555 and has a supporting frame 503 arranged on a body (not shown) of the testing apparatus 500, a supporting spring 504 arranged on an indenter shaft support 503a which stands on the supporting frame 503, a motion plate 507 elastically supported by the supporting frame 503 through a plate spring 505 and a return spring 506, a push bar 508 arranged on the supporting frame 503 so as to be movable in the upper and lower directions, the indenter shaft 502 and the like. A lower end 508a of the push bar 508 comes in contact with an external end 507b of the motion plate 507. An upper end 502a of the indenter shaft 502 is attached to the supporting spring 504, and a contact member 502b of the indenter shaft 502 is supported by a shaft receiver 507a of the motion plate 507 placed below the indenter shaft 502.

The load applying mechanism 530 has a dead weight member 570 arranged above the indenter shaft unit 510 and a control lever 520.

The control lever 520 is supported by a rotational shaft 521 at the almost center of the control lever 520 so as to rotate around the body of the testing apparatus. A pressing member 522 is arranged on one end 520a of the control lever 520 to push down the upper end of the pushing bar 508 of the indenter shaft unit 510. A roller 524 being rotatably contacted with an eccentric cam 523 is attached to the other end 520b of the control lever 520. The control lever 520 extends from the rotational shaft 521 toward a position above the indenter shaft unit 510 and extends above the indenter shaft 502, and the end 520a of the control lever 520 pushes down the pushing bar 508 at an upper position of the pushing bar 508. A hole 520c extending in the vertical direction is formed in the control lever 520 at a position placed above the indenter shaft 502 of the control lever 520.

The dead weight member 570 has a plurality of dead weights 571, a load shaft 572 vertically extending in the center of the dead weight member 570, and a casing 573 covering the dead weights 571. A lower portion of the load shaft 572 penetrates through the hole 520c of the control lever 520 and extends downward, and a lower end 572a of the load shaft 572 is arranged so as to be opposite to an upper end 502a of the indenter shaft 502. A pin 574 projects from the load shaft 572 and comes in contact with the control lever 520 from its upper side.

In the above configuration of the hardness testing apparatus 500, the control lever 520 is rotated with the rotation of the eccentric cam 523 to push down the push bar 508 of the indenter shaft unit 510 or to release the push-down of the push bar 508. When the push bar 508 is pushed down, the supporting frame 503 (motion plate 507) is pushed down. The control lever 520 lowers the position of the dead weight member 570 to apply a predetermined load to the indenter shaft 502.

When the hardness test is performed by using the hardness testing apparatus 500, the sample S is mounted on the sample stand 555 placed below the indenter shaft 502 in the body of the hardness testing apparatus 500, and the position of the indenter shaft 502 is lowered by rotating the eccentric cam 523 and lowering the position of the dead weight member 570. When the position of the indenter shaft 502 is lowered so as to make the top of the indenter 501 come in contact with the sample S, the indenter shaft 502 is released from the shaft receiver 507a of the motion plate 507. Thereafter, the dead weight member 570 applies a predetermined load (weight of the dead weights 571; test force, for example, from almost 98 mN to 20N) to the indenter shaft 502, and a dimple is formed in the sample S by the indenter 501. After formation of the dimple, the control lever 520 is rotated in the direction reverse to that in the formation of the dimple to heighten the position of the supporting frame 503 (motion plate 507) and to move the indenter shaft 502 upward, and the indenter shaft 502 departs from the sample S. Therefore, the size of the dimple or the like is measured by observing the dimple formed in the sample S with a microscope (not shown) or the like, and a hardness of the sample S is determined.

However, in case of the Application No. H10-132722, when the test force is output from the dead weights 571 of the dead weight member 570 arranged in the hardness testing apparatus 500 so as to make the hardness testing apparatus 500 form the dimple in the sample S, a problem arises in that a repulsion force of both the supporting spring 504 and the return spring 506 elastically supporting the indenter shaft 502 acts to deaden the test force.

That is, in the hardness testing apparatus 500, the action force (repulsion force) influences the test force output based on the dead weights 571 of the dead weight member 570, and the hardness test is performed at a test force slightly different from the substantial test force.

Further, in the case of Application No. H10-132722, because the test force required to form the dimple in the sample S is output by the dead weight member 570 of the hardness testing apparatus 500, the test force is discretely output according to each dead weight 571 in the range based on the dead weights 571 of the dead weight member 570.

In a second earlier development, in a hardness testing apparatus 540 schematically shown in FIG. 26A, an indenter shaft 544 having an indenter 543 at the top thereof is elastically supported to a body 542 of the testing apparatus through supporting springs 545. A predetermined force F is applied to the indenter shaft 544 in its axial direction to push the indenter 543 to a sample, and a dimple is formed in the sample. A hardness of the sample is measured according to the shape of the dimple (for example, refer to Published Japanese Patent Application (Tokkaihei) No. H11-37915).

However, in the case of Application No. H11-37915, as shown in FIG. 26A, even though the force F is applied to the indenter shaft 544 in its axial direction, the shaft axis of the indenter shaft 544 sometimes slightly deviates in a direction perpendicular to the axial direction of the indenter shaft 544 because of warps of the supporting springs 545. When the shaft axis of the indenter shaft 544 deviates, as shown in FIG. 26B, flaws generated by the dragging of the indenter 543 along the surface of the sample are sometimes formed in the dimple. Therefore, the flaws sometimes prevent the correct recognition of the shape of the dimple, and a problem arises in that a hardness of the sample sometimes cannot be measured with high accuracy.

In a third earlier development, a hardness testing apparatus disclosed in Published Japanese Patent Application (Tokkai) No. 2003-161684 has an indenter supporting bar having an indenter at the top thereof, a supporting mechanism for movably supporting the indenter supporting bar, and an actuator for driving the indenter supporting bar in its axial direction.

The supporting mechanism has two plate springs supporting the top and bottom of the indenter supporting bar respectively and formed in an E shape. The plate springs are arranged at upper and lower positions of the indenter supporting bar respectively and extend parallel to each other in the same direction as each other. Open ends of both side spring portions in each plate spring are fixed to a fixed frame, and an open end of the central spring portion each plate spring is fixed to the indenter supporting bar supporting the indenter.

When a predetermined force is applied to the indenter supporting bar in an axial direction the indenter supporting bar, the side spring portions and the central spring portions of the plate springs are deformed. Circular motions of the side spring portions and the central spring portions in the plate springs arranged in parallel to each other cancel each other out with the deformation of the plate springs, and the indenter supporting bar can straight move. Therefore, the indenter always faces the surface of the sample without changing the direction of the indenter, and the indenter performs only straight movement.

However, in the above-described configuration of the supporting mechanism, when the moving speed of the indenter supporting bar is increased, the indenter supporting bar vibrates at its characteristic frequency due to the action force applied from the actuator to the indenter supporting bar, and the indenter violently collides with the sample. Therefore, a problem arises in that a hardness of the sample is erroneously measured.

Further, when the indenter supporting bar vibrates due to disturbance, the indenter supporting bar vibrates in the upper and lower directions at its characteristic frequency. As a result, the load applied to the sample is changed due to the influence of vibration of disturbance. Therefore, another problem arises in that a hardness of the sample is erroneously measured in the test of a low hardness of a film or the like.

Moreover, when the force is applied to the indenter supporting bar, the two upper and lower plate springs are independently moved. Therefore, the indenter supporting bar slightly deviates in the direction perpendicular to the axial direction of the bar, and the dimple formed by the indenter is deformed. As a result, another problem arises in that a hardness of the sample is erroneously measured.

In the hardness testing apparatus disclosed in Application No. 2003-161684, when the two upper and lower plate springs composing the supporting mechanism are connected to each other by a connecting member, movement of indenter supporting bar further can be made straight in the axial direction of the bar.

However, in this hardness testing apparatus, when the indenter reaches the surface of the sample while applying a predetermined force to the indenter supporting bar, the two plate springs are further warped as compared with in the before-test of the hardness.

Therefore, when vibration of disturbance occurs in the connecting member of the plate springs, the indenter supporting bar sometimes slightly deviates in the direction perpendicular to the axial direction of the bar, and the dimple formed by the indenter is deformed. Therefore, a problem arises in that a hardness of the sample is erroneously measured.

In a fourth earlier development, Vickers hardness testing apparatus is known as a hardness testing apparatus (for example, refer to Published Japanese Patent Application (Tokkai) No. 2000-292333). In this apparatus, the size (for example, length between predetermined points of dimple (length of diagonal line)) of a dimple formed by pushing an indenter to a sample at a predetermined force is measured, and a hardness of the sample is calculated. The Vickers hardness testing apparatus has an indenter for forming the dimple in the sample and an objective lens for displaying an enlarged image of the dimple formed by the indenter on a monitor. Normally, a plurality of objective lenses are prepared to measure dimples having various sizes.

When a user daily performs the hardness test of a fixed type of sample, it is easy to assume a hardness of the sample by user's experience. Therefore, the user determines an optimum objective lens according to information relating to the size of the dimple, a test force is set by user's experience to push the indenter to the sample according to the assumed hardness of the sample, and the hardness test is performed.

In the Vickers hardness testing apparatus of Application No. 2000-292333, to display the image of the dimple at its optimum size on the monitor, it is required to select an objective lens having a magnification optimum to the size of the dimple. However, because the selection of the objective lens based on the size of the dimple is performed by user's experience, the user requires a certain degree of skill.

Further, when the test force set by user's experience is not appropriate, a dimple having a size considerably far from the expected size is formed in the sample. Therefore, the image of the dimple cannot be displayed at the optimum size on the monitor, and a problem arises in that the hardness test cannot be accurately performed.

SUMMARY

In order to solve the above problem, a first object of the present invention is to provide a hardness testing apparatus, in which a hardness test is performed at a further correct test force.

A second object is to provide a hardness testing apparatus in which a hardness test is performed at various test forces of a wide range.

A third object is to provide a hardness testing apparatus in which a dimple is further accurately formed on the surface of a sample by an indenter.

A fourth object is to provide a hardness testing apparatus in which a hardness test is performed with further accuracy while reducing measurement error caused by influence of vibration of disturbance and/or a moving speed of an indenter.

A fifth object is to provide a hardness testing apparatus in which a hardness test is performed with further accuracy while reducing measurement error caused by influence of vibration of disturbance without any complicated mechanism.

A sixth object is to provide a hardness testing apparatus in which a test force corresponding to a hardness of a sample assumed by a user is set with accuracy.

A seventh object is to provide a hardness testing apparatus in which a person not sufficiently skilled in a hardness test can perform the hardness test.

In order to accomplish the above-mentioned first object, in accordance with a first aspect of the present invention, there is provided a hardness testing apparatus (41, 42, 43) comprising:
- an indenter shaft (2) having an indenter (1) at a top thereof;
- a force motor (10, 30) for moving the indenter shaft in its axial direction and applying a predetermined test force to a sample (S) through the indenter;
- an external force detection section (for example, a vibration detection section 60) for detecting an external force applied from outside of the hardness testing apparatus to the indenter shaft when the indenter shaft is moved by the force motor; and
- an external force adjustment and control section (for example, a vibration adjustment and control section 72) for controlling the force motor to apply the predetermined test force to the sample deadening the external force detected by the external force detection section.

In the hardness testing apparatus according to the first aspect of the present invention, when the force motor moves the indenter shaft having the indenter at the top thereof in its axial direction and applies the predetermined test force to the sample through the indenter, the external force adjustment and control section performs the control for deadening the external force applied from the outside of the hardness testing apparatus to the indenter shaft by adjusting the driving of the force motor so as to deaden the external force detected by the external force detection section.

That is, in the hardness testing apparatus, when the external force is applied from the outside of the hardness testing apparatus to the indenter shaft, the external force adjustment and control section controls the force motor to deaden influence of the external force on the movement of the indenter shaft. The force motor moves the indenter shaft in its axial direction so as to make the indenter apply the predetermined test force to the sample.

Concretely, for example, vibration from the outside of the hardness testing apparatus is applied to the indenter shaft as an external force so as to influence movement of the indenter shaft. When the indenter shaft applies force caused by the vibration to the sample through the indenter, the external force adjustment and control section adjusts and controls the movement of the indenter shaft performed by the force motor so as to reduce load equivalent to the force caused by the vibration. When force applied by the indenter shaft to the sample through the indenter is deadened by the vibration, the external force adjustment and control section adjusts and controls the movement of the indenter shaft performed by the force motor so as to increase load equivalent to the force caused by the vibration.

Therefore, even though the external force acts on the indenter shaft from the outside of the hardness testing apparatus, when the external force is deadened by controlling the operation of the force motor moving the indenter shaft, the predetermined test force can be applied to the sample through the indenter. Accordingly, the hardness testing apparatus can perform the hardness test at a further correct test force.

In order to accomplish the first object, in accordance with a second aspect of the present invention, there is provided a hardness testing apparatus (41, 42, 43) comprising:
- an indenter shaft (2) having an indenter (1) at a top thereof;
- a force motor (10, 30) for moving the indenter shaft in its axial direction and applying a predetermined test force to a sample (S) through the indenter; and
- a self-weight adjustment and control section (71) for controlling the force motor to apply the predetermined test force to the sample while deadening a load force acting on the indenter shaft according to a self-weight of the indenter shaft.

In the hardness testing apparatus according to the second aspect of the present invention, when the force motor moves the indenter shaft having the indenter at the top thereof in its axial direction and applies the predetermined test force to the sample through the indenter, the self-weight adjustment and control section performs the control for deadening a load force based on a self-weight of the indenter shaft and acting on the movement of the indenter shaft by adjusting the driving of the force motor.

That is, in the hardness testing apparatus, when the self-weight of the indenter shaft is applied as the load force acting on the indenter shaft, the self-weight adjustment and control section controls the driving of the force motor so as to deaden influence of the load force on the movement of the indenter shaft. The force motor moves the indenter shaft in its axial direction so as to make the indenter apply the predetermined test force to the sample.

Concretely, for example, the load force caused by the self-weight of the indenter shaft of the hardness testing apparatus influences on the movement of the indenter shaft. When the indenter shaft applies the load force to the sample through the indenter, the self-weight adjustment and control section adjusts and controls the movement of the indenter shaft performed by the force motor so as to reduce load equivalent to the load force.

Therefore, even though the load force based on the self-weight of the indenter shaft of the hardness testing apparatus acts on the indenter shaft, when the load force is deadened by controlling the operation of the force motor moving the indenter shaft, the predetermined test force can be applied to the sample through the indenter. Accordingly, the hardness testing apparatus can perform the hardness test at a further correct test force.

In order to accomplish the first object, in accordance with a third aspect of the present invention, there is provided a hardness testing apparatus (41, 42, 43) comprising:
- an indenter shaft (2) having an indenter (1) at a top thereof;
- a force motor (10, 30) for moving the indenter shaft in its axial direction and applying a predetermined test force to a sample (S) through the indenter;
- an elastic supporting structure (for example, supporting springs 3) for elastically supporting the indenter shaft on a body of the hardness testing apparatus (for example, testing apparatus body 75); and
- a repulsion force adjustment and control section (73) for controlling the force motor to apply the predetermined test force to the sample while deadening a repulsion force acting on the indenter shaft according to elastic deformation of the elastic supporting structure.

In the hardness testing apparatus according to the third aspect of the present invention, when the force motor moves the indenter shaft having the indenter at the top thereof in its axial direction and applies the predetermined test force to the sample through the indenter, the repulsion force adjustment and control section adjusts the driving of the force motor to perform the control for deadening a repulsion force acting on the indenter shaft due to deformation of the elastic supporting structure elastically supporting the indenter shaft when the indenter shaft is moved in its axial direction.

That is, in the hardness testing apparatus, a recovery action force is generated when the elastic supporting structure elastically deformed due to the movement of the indenter shaft in its axial direction is returned to the original shape. When the recovery action force is applied to the indenter shaft as a repulsion force acting on the indenter shaft, the repulsion force adjustment and control section controls the driving of the force motor so as to deaden influence of the repulsion force on the movement of the indenter shaft. The force motor moves the indenter shaft in its axial direction so as to make the indenter apply the predetermined test force to the sample.

Concretely, for example, the repulsion force generated by deformation of the elastic supporting structure elastically supporting the indenter shaft of the hardness testing apparatus is transmitted to the indenter shaft and influences on the movement of the indenter shaft. When a force applied to the sample by the indenter shaft through the indenter is deadened by the repulsion force, the repulsion force adjustment and control section adjusts and controls the movement of the indenter shaft performed by the force motor so as to increase load equivalent to the repulsion force.

Therefore, even though the repulsion force generated by deformation of the elastic supporting structure elastically supporting the indenter shaft of the hardness testing apparatus acts on the indenter shaft, when the repulsion force is deadened by controlling the operation of the force motor moving the indenter shaft, the predetermined test force can be applied to the sample through the indenter. Accordingly, the hardness testing apparatus can perform the hardness test at a further correct test force.

Preferably, the hardness testing apparatus further comprises:

a pressing member (for example, loading shaft 31) for pressing the indenter shaft in its axial direction, and the force motor comprises:

a first force motor (10) for moving the indenter shaft in its axial direction and applying a force within range of a first test force to the sample through the indenter; and a second force motor (30) for making the pressing member press the indenter shaft in its axial direction to move the indenter shaft and applying a force within range of a second test force to the sample through the indenter.

In this invention, the same effect as that in the hardness testing apparatus according to the first, second or third aspect can be obtained. Further, in the hardness testing apparatus with the indenter shaft having the indenter at the top thereof, the first force motor applies a force within range of a first test force to the sample through the indenter by moving the indenter shaft in its axial direction, and the second force motor applies a force within range of a second test force to the sample through the indenter by making the pressing member move the indenter shaft in its axial direction.

That is, the hardness testing apparatus can perform the hardness test at a force (test force) obtained by combining forces applied by the first and second force motors to the indenter shaft.

Accordingly, the hardness testing apparatus can perform the hardness test at various forces (test forces) obtained by combining test forces (load forces, driving forces) output from the first and second force motors.

For example, when the force motors can output the almost same test force as each other, the test force output by combining the forces of the force motors can become almost twice compared with the use of the single force motor. Accordingly, the hardness test can be performed at the test forces of further wide range.

Further, for example, when one force motor is appropriate for outputting a large test force and the other force motor is appropriate for outputting a small test force, the test force corresponding to the object can be output, and the hardness test can be performed with test forces of a wide range.

Moreover, in the hardness testing apparatus, the hardness testing apparatus can apply the predetermined test force to the sample through the indenter by adjusting and controlling one force motor to move the loading shaft so as to output a predetermined test force and adjusting and controlling the other force motor to move and drive the loading shaft so as to deaden the action force disturbing the action of the test force. Accordingly, the hardness testing apparatus can perform the hardness test at a further correct test force.

Preferably, the pressing member comprises a lever (for example, control lever 50) rotatably supported by a shaft (for example, rotational shaft 51) extending perpendicularly to the axial direction of the indenter shaft, an end (for example, another end 50b) of the lever pressing the indenter shaft while the lever is rotated, and the hardness testing apparatus further comprises a center-of-mass adjustment and control section (74) for controlling at least one of the first and second force motors to apply the predetermined test force to the sample while deadening a moment force acting on the indenter shaft due to movement of a center-of-mass of the lever caused by rotational movement of the lever when the indenter shaft is moved.

In this invention, the same effect as that in the hardness testing apparatus described just before can be obtained. Further, when the lever rotatably supported by the shaft extending perpendicularly to the axial direction of the indenter shaft is rotationally moved, the end of the lever applies the pressing force to the indenter shaft, moves the indenter shaft in its axial direction and applies the predetermined test force to the shaft through the indenter. In this case, when the center-of-mass adjustment and control section adjusts at least one of the driving forces of the first and second force motors, the center-of-mass adjustment and control section performs the control for deadening the moment force acting on the indenter shaft due to movement of the center-of-mass of the lever caused by the rotational movement of the lever.

That is, in the hardness testing apparatus, when balance change based on the movement of the center-of-mass of the lever due to inclination of the lever of the pressing member rotationally moved is applied as a moment force acting on the indenter shaft, the center-of-mass adjustment and control section controls the driving of the force motors so as to deaden influence of the moment force on the movement of the indenter shaft. The force motors move the indenter shaft in its axial direction to make the indenter apply the predetermined test force to the sample.

Concretely, for example, a moment force based on the movement of the center-of-mass of the lever toward the side of the indenter shaft due to inclination of the lever of the pressing member of the hardness testing apparatus rotationally moved is applied to the indenter shaft. When the indenter shaft makes the indenter apply a force based on the moment force to the sample, the center-of-mass adjustment and control section adjusts and controls the movement of the indenter shaft performed by the force motors so as to reduce the load equivalent to the moment force.

Therefore, even though the moment force based on the movement of the center-of-mass of the lever due to inclination of the lever of the pressing member of the hardness testing apparatus rotationally moved acts on the indenter shaft, when the moment force is deadened by controlling the operation of the force motors (first and second force motors) moving the indenter shaft, the predetermined test force can be applied to the sample through the indenter. Accordingly, the hardness testing apparatus can perform the hardness test at a further correct test force.

In order to accomplish the second object, in accordance with a forth aspect of the present invention, there is provided a hardness testing apparatus comprising:

an indenter shaft (2) having an indenter (1) at a top thereof;

a first load applying mechanism (for example, force motor 10) for moving the indenter shaft in its axial direction and applying a force within range of a first test force to a sample (S) through the indenter; and a second load applying mechanism (for example, force motor 30), having a pressing member (for example, loading shaft 31) for applying a force within range of a second test force to the sample through the indenter by making the pressing member move the indenter shaft in its axial direction.

According to the fourth aspect of the present invention, in the hardness testing apparatus with the indenter shaft having the indenter at the top thereof, the first load applying mechanism applies the force within range of a first test force to the sample through the indenter by moving the indenter shaft in its axial direction, and the second load applying mechanism applies the force within range of a second test force to the sample through the indenter by making the pressing member move the indenter shaft in its axial direction. That is, the hardness testing apparatus can perform the hardness test by the force (test force) obtained by combing forces applied to the indenter shafts by the first and second load applying mechanisms.

Accordingly, the hardness testing apparatus can perform the hardness test at various forces (test forces) obtained by combining the test forces (loading forces, driving forces) output from the two load applying mechanisms.

For example, when the two load applying mechanisms can output almost the same test force as each other, the test force output by combining the forces of the two load applying mechanisms can become almost twice that compared with the use of the single load applying mechanism. Accordingly, the hardness test can be performed at test forces of a further wide range.

Further, for example, when one load applying mechanism is appropriate for outputting a large test force and the other load applying mechanism is appropriate for outputting a small test force, the hardness testing apparatus can output various test forces in a wide range by outputting a combined force of the two load applying mechanisms, and the hardness test can be performed at test forces of a wide range.

Preferably, the pressing member comprises a lever (for example, control lever 50) rotatably supported by a shaft (for example, rotational shaft 51) extending perpendicularly to the axial direction of the indenter shaft, and the second load applying mechanism apply an action force to an end (50*a*) of the lever to make another end (50*b*) of the lever press the indenter shaft and apply the second test force to the sample in the axial direction of the indenter shaft.

In this invention, the same effect as that in the hardness testing apparatus according to the fourth aspect can be obtained. Further, the second load applying mechanism applies an action force to one end of the lever rotatably supported by the shaft extending perpendicularly to the axial direction of the indenter shaft, and the other end of the lever applies a pressing force to the indenter shaft. That is, in the hardness testing apparatus, the second load applying mechanism presses the indenter shaft through the lever and applies the second test force to the sample in the axial direction of the indenter shaft.

Accordingly, in the hardness testing apparatus, even in the case of a small test force, the second load applying mechanism can apply the test force to the indenter shaft as a larger pressing force by using so-called "principle of lever".

Preferably, the first and second load applying mechanisms are force motors (10, 30).

In this invention, the same effect as that in the hardness testing apparatus according to the fourth aspect can be obtained. Further, because the first and second load applying mechanisms are force motors, the load applying mechanisms generate an arbitrary driving force according to an amount of current supplied to the force motors and can apply various forces (test forces) to the indenter shaft according to the driving force. Particularly, the load applying mechanisms output stepless driving forces by adjusting the amount of current supplied to the force motors in stepless, and the load applying mechanisms can apply stepless forces (test forces) to the indenter shaft.

In order to accomplish the third object, in accordance with a fifth aspect of the present invention, there is provided a hardness testing apparatus (44, 45, 46, 47, 48) comprising:

an indenter shaft (104) having an indenter (103) at a top thereof;

a supporting structure (105, 115, 205, 305) for supporting the indenter shaft movably in its axial direction, the supporting structure comprising:

a first elastic member (153, 113, 213, 223, 353) having an end fixed to the indenter shaft;

a second elastic member (154, 114, 214, 224, 354) having an end fixed to a body of the hardness testing apparatus; and a connecting portion (155, 355) for connecting another end of the first elastic member and another end of the second elastic member; and a load applying mechanism (106) for applying a predetermined force to the indenter shaft in its axial direction, wherein the second elastic member is warped to deaden movement of the indenter shaft which is caused by warp of the first elastic member in the axial direction of the indenter shaft, when the load applying mechanism applies the predetermined force to the indenter shaft, and is directed in a direction perpendicular to the axial direction of the indenter shaft.

In the hardness testing apparatus according to the fifth aspect of the present invention, when the load applying mechanism applies the predetermined force to the indenter shaft in its axial direction, the indenter shaft is moved while warping the first elastic member having the end fixed to the indenter shaft. Further, the predetermined force of the load applying mechanism is transmitted to the second elastic member connected to the other end of the first elastic member through the connecting portion, and the second elastic member is also warped. Because the first elastic member is warped by the warp of the second elastic member, the movement of the indenter shaft in the direction perpendicular to the axial direction of the indenter shaft is deadened. Therefore, the indenter shaft can be moved along its axial direction without displacing the shaft axis of the indenter shaft in the direction perpendicular to the axial direction of the indenter shaft.

Accordingly, because the indenter can be pressed to the sample in the axial direction of the indenter shaft, a dimple can be formed with further accuracy, and the measuring test of the hardness of the sample can be performed with further accuracy.

Preferably, the first and second elastic members are integrally formed out of a plate spring (151, 351).

In this invention, the same effect as that in the hardness testing apparatus according to the fifth aspect can be obtained. Further, because the first and second elastic members are integrally formed out of a plate spring, spring constants and amounts of warp of the first and second elastic members can be easily adjusted by adjusting shapes of the first and second elastic members. For example, the first and second elastic members can have almost the same spring constant and almost the same amount of warp as each other by setting the first and second elastic members having almost the same shape as each other.

Preferably, the supporting structure comprises at least two structures (151), and each structure comprise the first elastic member, the second elastic member and the connecting portion.

In this invention, the same effect as that in the hardness testing apparatus according to the fifth aspect can be obtained. Further, because the indenter shaft is supported on the test apparatus body by the structures at least two points, the displacement and inclination of the shaft axis of the indenter shaft can be further easily prevented, and the indenter shaft can be further stably moved in its axial direction.

In order to accomplish the fourth object, preferably, the hardness testing apparatus further comprises an attenuator (for example, damping coil 164 and the like) for attenuating vibration of the indenter shaft.

In this invention for the fourth object, because vibration of the indenter shaft occurring due to moving speed of the indenter and/or influence of vibration of disturbance can be attenuated by the attenuator, measuring error can be reduced, and a measuring result can be attenuated with further accuracy.

In the hardness testing apparatus for the fourth object, preferably, the load applying mechanism comprises:
 a magnetic field inducing member (160) for inducing a magnetic field;
 a driving coil (162), arranged in the magnetic field induced by the magnetic field inducing member, for receiving a driving current;
 a power supply (not shown) for supplying the driving current to the driving coil; and
 a pressing member (for example, coil bobbin 163) for pressing the indenter shaft by a driving force generated by the driving coil to which the power supply supplies the driving current, and
 the attenuator comprise:
 a damping coil (164) arranged in the magnetic field induced by the magnetic field inducing member.

In this invention, the same effect as that in the hardness testing apparatus for the fourth object can be obtained. Further, when vibration of disturbance acts on the indenter shaft to vibrate the indenter shaft, an electromotive force is generated in the damping coil arranged in the magnetic field induced by the magnetic field inducing member, and current flows. Accordingly, because an attenuation force is generated, vibration of the indenter shaft can be appropriately attenuated.

Preferably, the attenuator further comprises a variable resistor (165) connected to the damping coil.

In this invention, the same effect as that in the hardness testing apparatus for the fourth object can be obtained. Further, because the resistance value of the damping coil can be changed by the variable resistor connected to the damping coil, the attenuation force attenuating vibration of the indenter shaft can be adjusted.

Preferably, the load applying mechanism comprises:
 a magnetic field inducing member (160) for inducing a magnetic field;
 a driving coil (162), arranged in the magnetic field induced by the magnetic field inducing member, for receiving a driving current;
 a power supply (not shown) for supplying the driving current to the driving coil; and
 a pressing member (for example, coil bobbin 163) for pressing the indenter shaft by a driving force generated by the driving coil to which the power supply supplies the driving current, and
 the attenuator comprises:
 a coil bobbin (163) made of conductor, the driving coil being wound on the coil bobbin.

In this invention, the same effect as that in the hardness testing apparatus for the fourth object can be obtained. Further, when vibration of disturbance acts on the indenter shaft to vibrate the indenter shaft, an electromotive force is generated in the coil bobbin made of conductor on which the driving coil is wound, and current flows. Accordingly, because an attenuation force is generated, vibration of the indenter shaft can be appropriately and easily attenuated.

Preferably, the supporting structure comprises:
 a plurality of structures (151) arranged along the axial direction of the indenter shaft, each structure comprising the first elastic member, the second elastic member and the connecting portion; and
 a connecting member (152) for connecting the connecting portions of each pair of structures adjacent to each other.

In this invention, the same effect as that in the hardness testing apparatus for the fourth object can be obtained. Further, because the connecting member connects the connecting portions of each pair of structures adjacent to each other, independent motion of the connecting portions can be prevented, and the indenter shaft can be straight moved in its axial direction.

Preferably, the hardness testing apparatus further comprises a connecting member attenuator (190; 191) for attenuating vibration of the connecting member.

In this invention, the same effect as that in the hardness testing apparatus just described before can be obtained. Further, because vibration of the connecting member is attenuated by the connecting member attenuator, the attenuation force can be further enlarged.

In the hardness testing apparatus according to the fifth aspect of the present invention, preferably, the supporting structure comprises:

- a plurality of structures (151) arranged along the axial direction of the indenter shaft, each structure comprising the first elastic member, the second elastic member and the connecting portion;
- a connecting member (152) for connecting the connecting portions of each pair of structures adjacent to each other; and
- a connecting member attenuator (for example, connecting member damping coil 190) for attenuating vibration of the connecting member.

In this invention, the same effect as that in the hardness testing apparatus according to the fifth aspect can be obtained. Further, the connecting member connects the connecting portions of each pair of structures adjacent to each other, and vibration of the connecting member can be attenuated by the connecting member attenuator. Therefore, vibration of the indenter shaft occurring due to the moving speed of the indenter and/or influence of vibration of disturbance can be attenuated in the hardness test. Accordingly, measuring error can be reduced, and a measuring result can be obtained with further accuracy.

Preferably, the connecting member attenuator comprises:
- a connecting member damping coil (190) arranged in the connecting member; and
- a connecting member magnetic field inducing member (180) for inducing a magnetic field, and
- a portion of the connecting member is arranged in the magnetic field induced by the connecting member magnetic field inducing member.

In this invention, the same effect as that in the hardness testing apparatus according to the fifth aspect can be obtained. Further, particularly, when vibration of disturbance acts on the indenter shaft to vibrate the indenter shaft, an electromotive force is generated in the connecting member damping coil arranged in the magnetic field induced by the magnetic field inducing member, and current flows. Accordingly, because an attenuation force is generated, vibration of the indenter shaft can be appropriately attenuated.

Preferably, the connecting member attenuator further comprises:
- a connecting member variable resistor (191) connected to the connecting member damping coil.

In this invention, the same effect as that in the hardness testing apparatus just described before can be obtained. Further, because the resistance value of the connecting member damping coil can be changed by the connecting member variable resistor connected to the connecting member damping coil, the attenuation force attenuating vibration of the indenter shaft can be adjusted.

Preferably, the connecting member is made of non-magnetic conductor, the connecting member attenuator comprises a connecting member magnetic field inducing member (180) for inducing a magnetic field, and a portion of the connecting member is arranged in the magnetic field induced by the connecting member magnetic field inducing member.

In this invention, the same effect as that in the hardness testing apparatus for the fourth object can be obtained. Further, particularly, the connecting member is made of non-magnetic conductor, and the connecting member attenuator comprises the connecting member magnetic field inducing member for inducing the magnetic field. Because the connecting member is arranged in the magnetic field induced by the connecting member magnetic field inducing member, an electromotive force is generated in the connecting member, and current flows through the connecting member. Accordingly, because an attenuation force is generated, vibration of the indenter shaft can be appropriately and easily attenuated.

In order to accomplish the fifth object, preferably, as shown in FIG. 16, the supporting structure comprises:
- a plurality of structures (351) arranged along the axial direction of the indenter shaft, each structure comprising the first elastic member, the second elastic member and the connecting portion; and
- a connecting member (352) for connecting the connecting portions of each pair of structures adjacent to each other, and
- warped shapes of the first and second elastic members of the supporting structure approach straight shapes while the indenter shaft is moved toward a sample, and the first and second elastic members extend in almost straight shapes in a direction perpendicular to the axial direction of the indenter shaft when the indenter reaches a surface of the sample.

In this invention for the fifth object, the warped shapes of the first and second elastic members of the supporting structure approach the straight shapes while the indenter shaft is moved toward the sample, and the first and second elastic members extend in the almost straight shapes in the direction perpendicular to the axial direction of the indenter shaft when the indenter reaches the surface of the sample. Therefore, even though vibration of disturbance acts on the connecting member of the supporting structure when a dimple is formed on the surface of the sample by the indenter, the indenter shaft is not displaced in the direction perpendicular to its axial direction. Accordingly, because the dimple formed by the indenter is not deformed, error in measuring a hardness can be reduced without any complicated mechanism.

Preferably, spring constants of the first and second elastic members are increased as displacement of the first and second elastic members becomes small, and the spring constants of the first and second elastic members are decreased as the displacement of the first and second elastic members becomes large.

In this invention, the same effect as that in the hardness testing apparatus for the fifth object is obtained. Further, particularly, the first and second elastic members have a non-linear elastic characteristic. That is, the spring constants of the first and second elastic members are increased as displacement of the first and second elastic members becomes small, and the spring constants of the first and second elastic members are decreased as the displacement of the first and second elastic members becomes large. Therefore, when displacement of the first and second elastic members is large, that is, when the first and second elastic members extend to change warped shapes to straight shapes by applying the predetermined test force to the indenter shaft to move the indenter shaft toward the sample, the spring constants of the first and second elastic members are decreased, and stiffness of the first and second elastic members in the axial direction of the indenter shaft can be decreased. Accordingly, because an amount of correction in calculation of a substantial test force can be reduced, error in measuring a hardness can be further reduced without any complicated mechanism. In view of further reducing the amount of correction, it is desirable that the first and second elastic members are thinly formed.

Further, because the first and second elastic members have the non-linear elastic characteristic, the indenter shaft can be supported only by the first elastic member.

Accordingly, no other mechanism for supporting the indenter shaft having the self-weight is not required.

In order to accomplish the sixth object, in accordance with a sixth aspect of the present invention, as shown in FIGS. 21, 22 and 23 as an example, there is provided a hardness testing apparatus (for example, hardness testing apparatus 601), which has a plurality of object lenses (for example, object lenses 407) to display an enlarged image of a dimple formed on a surface of a sample (for example, sample S) by an indenter (for example, indenter 405) on a display and measures a hardness of the sample according to the dimple, comprising:

- a test force applying section (for example, arm driver 404) for applying a predetermined test force at which the indenter is pushed to the surface of the sample;
- a penetration detection section (for example, indenter shaft displacement detector 420) for detecting an amount of penetration of the indenter into the sample when the indenter is pushed into the sample by the test force applied by the test force applying section to form a dimple;
- a distance calculation section (for example, control section 611) for calculating a distance between predetermined characteristic points of the dimple according to the amount of penetration detected by the penetration detection section;
- an objective lens selection section (for example, control section 611) for selecting one predetermined objective lens from the objective lenses according to the distance calculated by the distance calculation section; and
- a notification section for notifying of a specification of the predetermined objective lens selected by the objective lens selection section.

In the hardness testing apparatus according to the sixth aspect of the present invention, when the test force applying section applies a predetermined test force to the indenter, the indenter is pushed into the sample, and a dimple is formed. At this time, the penetration detection section detects an amount of penetration of the indenter into the sample, and the distance calculation section calculates a distance between predetermined characteristic points of the dimple according to the distance. Thereafter, the objective lens selection section selects one predetermined objective lens from the objective lenses according to the distance, and the notification section notifies the user of a specification of the selected predetermined objective lens. That is, though the user performs the selection of one objective lens corresponding to the dimple by user's experience in the earlier development, the hardness testing apparatus automatically performs the selection of one objective lens corresponding to the dimple.

Accordingly, because the user of the hardness testing apparatus is not required to select one objective lens by user's experience or acknowledge in the hardness test, even a person insufficiently skilled in the hardness test can easily perform the hardness test.

Preferably, the hardness testing apparatus further comprises:

- a supporting section (for example, turret 408) for supporting the indenter and the objective lenses;
- a driving section (for example, driving motor 483) for driving the supporting section to make the indenter and the objective lenses be movable; and
- a driving control section (for example, control section 611) for controlling the driving section to move the indenter after formation of the dimple and to move the predetermined objective lens selected by the objective lens selection section above the dimple.

In this invention, the same effect as that in the hardness testing apparatus according to the sixth aspect is obtained. Further, after formation of the dimple, the driving control section controls the driving section to move the indenter and to move the selected predetermined objective lens above the dimple.

Accordingly, the user of the hardness testing apparatus is not required to select one objective lens by user's experience or knowledge in the hardness test. Further, because the user is not required to set one objective lens corresponding to the dimple by himself or herself, even a person insufficiently skilled in the hardness test can easily perform the hardness test.

In order to accomplish the sixth object, in accordance with a seventh aspect of the present invention, as shown in FIGS. 21, 22 and 23 as an example, there is provided a hardness testing apparatus (for example, hardness testing apparatus 601), which has a plurality of object lenses (for example, object lenses 407) to display an enlarged image of a dimple formed on a surface of a sample (for example, sample S) by an indenter (for example, indenter 405) on a display and measures a hardness of the sample according to the dimple, comprises:

- a test force applying section (for example, arm driver 404) for applying a predetermined test force at which the indenter is pushed to the surface of the sample;
- a penetration detection section (for example, indenter shaft displacement detector 420) for detecting an amount of penetration of the indenter into the sample when the indenter is pushed into the sample by the test force applied by the test force applying section to form a dimple;
- a distance calculation section (for example, control section 611) for calculating a distance between predetermined characteristic points of the dimple according to the amount of penetration detected by the penetration detection section;
- an objective lens selection section (for example, control section 611) for selecting one predetermined objective lens from the objective lenses according to the distance calculated by the distance calculation section;
- a supporting section (for example, turret 408) for supporting the indenter and the objective lenses;
- a driving section (for example, driving motor 483) for driving the supporting section to make the indenter and the objective lenses be movable; and
- a driving control section (for example, control section 611) for controlling the driving section to move the indenter after formation of the dimple and to move the predetermined objective lens selected by the objective lens selection section above the dimple.

In the hardness testing apparatus according to the seventh aspect of the present invention, when the test force applying section applies a predetermined test force to the indenter, the indenter is pushed into the sample, and a dimple is formed. At this time, the penetration detection section detects an amount of penetration of the indenter into the sample, and the distance calculation section calculates a distance between predetermined characteristic points of the dimple according to the amount of penetration. Thereafter, the objective lens selection section selects one predetermined objective lens from the objective lenses according to the distance, and the driving control section controls the driving section to move the indenter after formation of the dimple and to move the selected predetermined objective lens above the dimple. That is, though the user performs the selection of one objective lens corresponding to the dimple by user's experience in the earlier development, the hardness testing apparatus automatically performs the selection of one objective lens corresponding to the dimple.

Therefore, the user of the hardness testing apparatus is not required to select one objective lens by user's experience or knowledge in the hardness test, and the user is not required to set one objective lens corresponding to the dimple by himself or herself. Accordingly, even a person insufficiently skilled in the hardness test can easily perform the hardness test.

Preferably, the objective lens selection section selects one objective lens to display the largest image of the dimple on the display among images based on the objective lenses.

In this invention, the same effect as that in the hardness testing apparatus according to the seventh aspect is obtained. Further, because the objective lens selection section selects one objective lens to display the largest image of the dimple on the display among images based on the objective lenses, the user can easily grasp features of the dimple.

In order to accomplish the seventh object, in accordance with an eighth aspect of the present invention, as shown in FIGS. 21, 22 and 24 as an example, there is provided a hardness testing apparatus (for example, hardness testing apparatus 602), which has a test force applying section (for example, arm driver 404) for applying a predetermined test force at which an indenter is pushed (for example, indenter 405) to a surface of a sample (for example sample S), and a plurality of object lenses (for example, object lenses 407) to display an enlarged image of a dimple formed on the surface of the sample by the indenter on a display (for example, display 416) and measures a hardness of the sample according to the dimple, comprising:

an assumed hardness input section (for example, input section 415) for receiving a hardness of the sample assumed by a user;

a dimple information input section (for example, input section 415) for receiving information relating to a size of the dimple from the user;

an objective lens selection section (for example, control section 612) for selecting one objective lens to be used for observation of the dimple according to the information relating to the size of the dimple input by the dimple information input section; and a test force calculation section (for example, control section 612) for calculating a test force, at which the indenter is pushed to the surface of the sample, according to the hardness of the sample input by the assumed hardness input section and a magnification of the objective lens selected by the objective lens selection section.

The information relating to the size of the dimple, for example, indicates information of the size of the dimple required to observe the dimple by an objective lens having a comparatively high magnification with high accuracy, information of the size of the dimple required to observe inside of the dimple at top priority by an objective lens having a comparatively low magnification, or the like.

In the hardness testing apparatus according to the eighth aspect of the present invention, the user inputs a hardness of the sample assumed by the user to the assumed hardness input section, and the user inputs information relating to a size of the dimple to the dimple information input section.

The objective lens selection section selects one objective lens to be used for observation of the dimple according to the information relating to the size of the dimple input by the dimple information input section, and the test force calculation section calculates a test force, at which the indenter is pushed to the surface of the sample, according to the hardness of the sample input by the assumed hardness input section and a magnification of the objective lens selected by the objective lens selection section.

Therefore, when the user inputs only a hardness of the sample for the hardness test, the hardness testing apparatus selects the magnification of the objective lens to be used for observation of the dimple and calculates the test force required for formation of the dimple. Accordingly, the user is not required to set the test force by user's experience, and an accurate test force corresponding to the hardness of the sample assumed by the user can be set.

In order to accomplish the seventh object, in accordance with a ninth aspect of the present invention, as shown in FIGS. 21, 22 and 24 as an example, there is provided a hardness testing apparatus (for example, hardness testing apparatus 602), which has a test force applying section (for example, arm driver 404) for applying a predetermined test force at which an indenter is pushed (for example, indenter 405) to a surface of a sample (for example sample S), and a plurality of object lenses (for example, object lenses 407) to display an enlarged image of a dimple formed on the surface of the sample by the indenter on a display (for example, display 416) and measures a hardness of the sample according to the dimple, comprising:

an assumed hardness input section (for example, input section 415) for receiving a hardness of the sample assumed by a user;

an objective lens selection section (for example, input section 415) for making the user select one objective lens to be used for observation of the dimple;

a recognition section (for example, control section 612) for recognizing a magnification of the objective lens selected in the objective lens selection section; and a test force calculation section (for example, control section 612) for calculating a test force, at which the indenter is pushed to the surface of the sample, according to the hardness of the sample input by the assumed hardness input section and the magnification of the objective lens recognized by the recognition section.

In the hardness testing apparatus according to the ninth aspect of the present invention, the user inputs a hardness of the sample assumed by the user to the assumed hardness input section, and the objective lens selection section selects one objective lens to be used for observation of the dimple. The recognition section recognizes a magnification of the objective lens selected by the objective lens selection section, and the test force calculation section calculates a test force, at which the indenter is pushed to the surface of the sample, according to the hardness of the sample input by the assumed hardness input section and the magnification of the objective lens recognized by the recognition section.

Therefore, when the user inputs a hardness of the sample for the hardness test and selects a magnification of an objective lens to be used for observation of the dimple, the hardness testing apparatus calculates the test force required for formation of the dimple. Accordingly, the user is not required to set the test force by user's experience, and an accurate test force corresponding to the hardness of the sample assumed by the user can be set.

Preferably, the display displays the test force calculated by the test force calculation section.

In this invention, the same effect as that in the hardness testing apparatuses according to the eighth or ninth aspect is obtained. Further, because the display displays the test force calculated by the test force calculation section, the test force can be visually notified to the user, the hardness test can be easily performed, and it is convenient to record the test force.

Preferably, the hardness testing apparatus further comprises:

a supporting section (for example, turret 408) for supporting the indenter and the objective lenses;

a driving section (for example, driving motor 483) for driving the supporting section to make the indenter and the objective lenses be movable; and a driving control section (for example, control section 612) for controlling the driving section to move the indenter after formation of the dimple and to move the objective lens selected by the objective lens selection section above the dimple.

In this invention, the same effect as that in the hardness testing apparatuses according to the eighth or ninth aspect is obtained. Further, the driving control section controls the driving section to move the indenter after formation of the dimple and to move the selected objective lens above the dimple.

Therefore, when the user inputs only a hardness of the sample for the hardness test, the hardness testing apparatus selects the objective lens to be used for observation of the dimple and calculates the test force required for formation of the dimple.

Accordingly, the user is not required to set the test force by user's experience, and an accurate test force corresponding to the hardness of the sample assumed by the user can be set.

BRIEF DESCRIPTION OF THE DRAWINGS

The present invention will become more fully understood from the detailed description given hereinbelow and the accompanying drawing which are given by way of illustration only, and thus are not intended as a definition of the limits of the present invention, and wherein.

DETAILED DESCRIPTION OF EMBODIMENTS

Hereinafter, embodiments of the present invention will be explained with reference to the drawings.

First Embodiment

Figure 1:
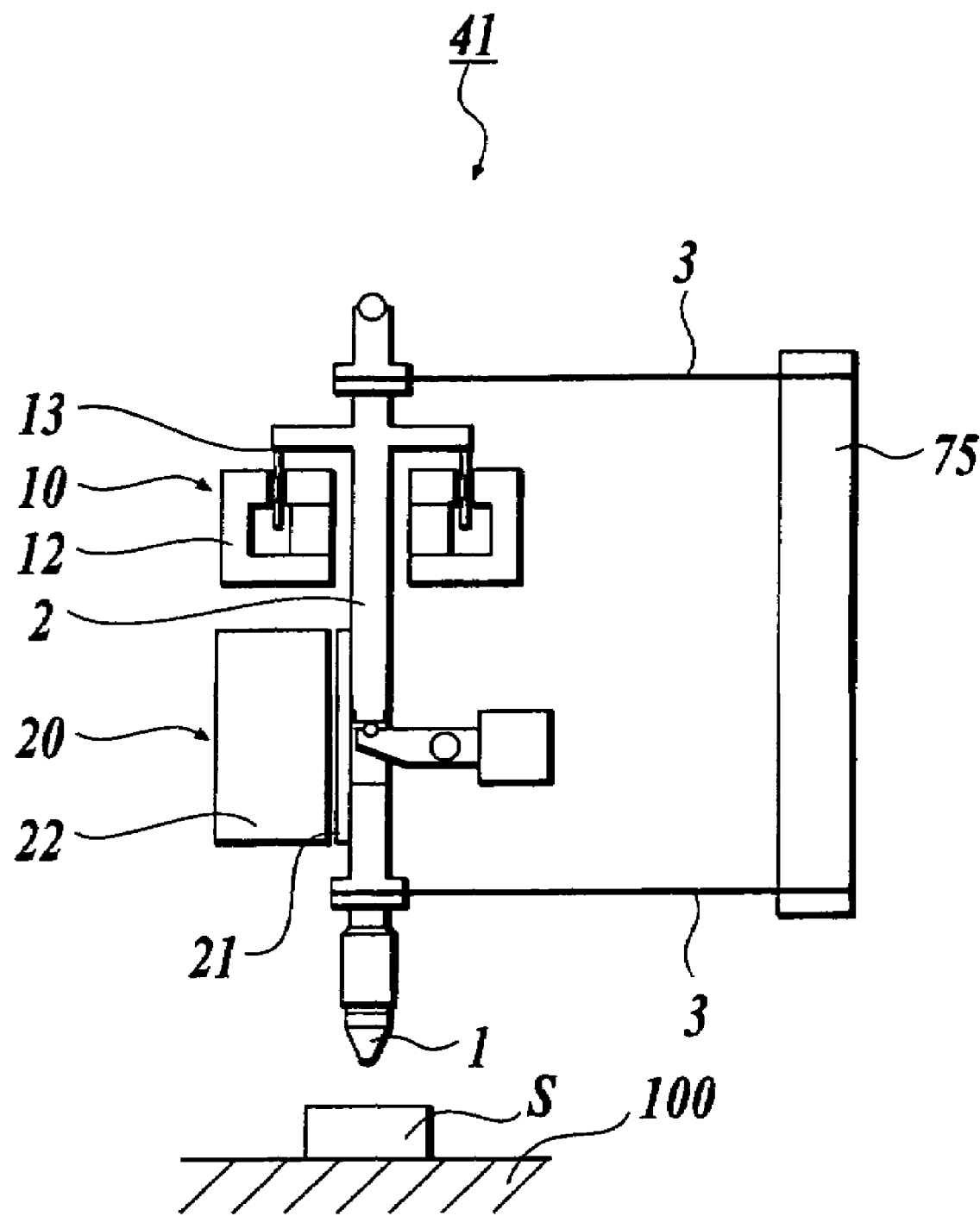
FIG. 1 is a side view in partial cross-section of a hardness testing apparatus according to the first embodiment of the present invention.

FIG. 1 is a side view in partial cross-section of a hardness testing apparatus.

Figure 2:
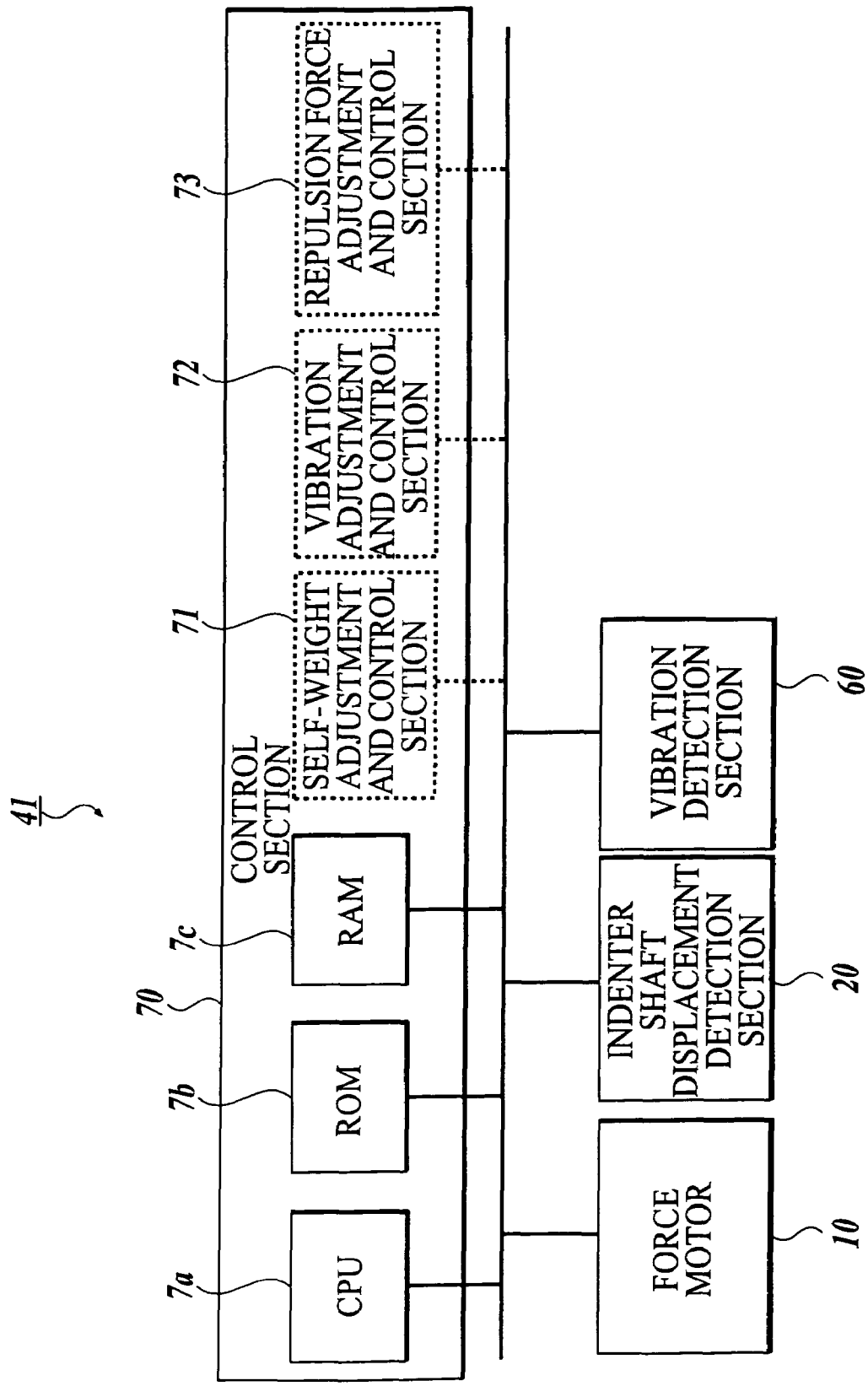
FIG. 2 is a block diagram showing a main section of the hardness testing apparatus according to the first embodiment of the present invention.

FIG. 2 is a block diagram showing a main section of the hardness testing apparatus shown in FIG. 1.

As shown in FIGS. 1 and 2, a hardness testing apparatus 41 comprises an indenter shaft 2 having a top on which an indenter 1 is arranged to form a dimple in a sample S mounted on a sample stand 100, two supporting springs 3 connected to a testing apparatus body 75 and elastically supporting the upper and lower ends of the indenter shaft 2 respectively so as to function as an elastic supporting structure, a force motor 10 for applying a predetermined force to the indenter shaft 2 in an axial direction of the indenter shaft 2 to move the indenter shaft 2 in the axial direction, an indenter shaft displacement detection section 20 for detecting an amount of displacement of the indenter shaft 2, a vibration detection section 60 for detecting vibration acting on the indenter shaft 2 to function as an external force detection section, and a control section 70 for controlling operations of the constituent elements of the testing apparatus 41 described above.

The indenter 1 is used for dimple forming hardness tests such as Vickers hardness test, Knoop indenter hardness test, Brinell hardness test, Rockwell hardness test and the like.

One end of each supporting spring 3 is fixed to the testing apparatus body 75, and the supporting spring 3 extends in the almost horizontal direction from the body 75. The other ends of the supporting springs 3 are connected to the upper and lower ends of the indenter shaft 2 respectively. The supporting springs 3 elastically supports the indenter shaft 2 to make the indenter shaft 2 be perpendicular to the sample stand 100. When the indenter shaft 2 is moved in the upper and lower directions by the force motor 10 or the like, the supporting springs 3 are warped and deformed so as to maintain the posture of the indenter shaft 2 perpendicular to the sample stand 100.

The force motor 10 comprises a magnetic circuit structure 12 and a driving coil 13 arranged on the side of the indenter shaft 2. The force motor 10 generates a force in the magnetic circuit structure 12 by electromagnetic induction which is based on both a magnetic field induced in a gap by a magnet and a current flowing through the driving coil 13 arranged in the gap. The force motor 10 uses the force as a driving force to move the indenter shaft 2 in its axial direction and to apply a predetermined force to the sample S through the indenter 1 arranged on the indenter shaft 2.

That is, the force motor 10 generates an arbitrary driving force according to an amount of current supplied to the driving coil 13, moves the indenter shaft 2 according to the driving force and applies various test forces to the sample S. Further, when the amount of current flowing through the driving coil 13 is adjusted in a stepless manner, the force motor 10 can output one of stepless driving forces and apply one of stepless test forces to the sample S.

The current supplied from the force motor 10 to the driving coil 13 is controlled by the control section 70 described later. The force motor 10 generates the driving force according to an amount of current (and/or a direction of the current) predetermined from the predetermined test force, moves the indenter shaft 2 and applies the predetermined test force to the sample S.

The indenter shaft displacement detection section 20 comprises a scale 21 having graduations at predetermined intervals and arranged on the indenter shaft 2 and a linear encoder 22 optically reading the graduations of the scale 21. The section 20 detects an amount of displacement (for example, an amount of penetration of the indenter 1 pushed into the sample S) of the indenter shaft 2 when the indenter shaft 2 is moved to form a dimple in the sample S, and the section 20 outputs an indenter shaft displacement signal based on the amount of displacement to the control section 70.

The vibration detection section 60 detects vibration acting on the indenter shaft 2 from the outside of the hardness testing apparatus 41 as an external force and outputs a vibration detection signal based on the detected vibration to the control section 70.

The control section 70 comprises a central processing unit (CPU) 7a for performing various types of calculations, a read only memory (ROM) 7b for storing various programs and various types of data used for various types of processing such as control, judgement and the like, and a random access memory (RAM) 7c used as a work memory for various types of processing. The control section 70 is connected to the force motor 10, the indenter shaft displacement detection section 20, the vibration detection section 60 and the like through a system bus, a driving circuit and the like.

When a test operation signal indicating the performance of the operation of the hardness test is input to an operation section (not shown), the control section 70 executes a predetermined program stored in the ROM 7b, supplies an amount of current based on a predetermined test force, which is determined according to predetermined operational conditions (for example, an operational condition of the indenter shaft 2) preset to perform a predetermined hardness test, to the driving coil 13 of the force motor 10, drives the force motor 10 to move the indenter shaft 2 and performs an operational control to apply the predetermined test force to the sample S.

Further, the control section 70 performs a control to calculate a hardness of the sample S according to data based on the dimple formed in the sample S, the test force applied for the formation of the dimple and a hardness calculation formula corresponding to a preset hardness test.

Moreover, the control section 70 further comprises a self-weight adjustment and control section 71, a vibration adjustment and control section 72 and a repulsion force adjustment and control section 73 which are embodied by software processing performed by co-operation of the CPU 7a and various processing programs stored in the ROM 7b. The control section 70 performs adjustment and control to apply only a substantial force to the sample S.

In detail, the self-weight adjustment and control section 71 of the control section 70 performs a self-weight adjustment and control to adjust an amount of current flowing through the driving coil 13 of the force motor 10 according to data of the self-weight (mass, weight) of the indenter shaft 2 (and indenter 1) stored in the ROM 7b of the control section 70 so as to deaden a loading force based on the self-weight of the indenter shaft 2 and acting on the sample S.

That is, the self-weight adjustment and control section 71 adjusts the amount of current flowing through the driving coil 13 according to the self-weight data of the indenter shaft 2 (and indenter 1) preset and the processing program so as to deaden the loading force based on the self-weight of the indenter shaft 2 and acting on the sample S, and the section 71 performs the adjustment and control to apply only a substantial test force to the sample S.

The vibration adjustment and control section 72 acting as an external force control section of the control section 70 performs a vibration adjustment and control to adjust the amount of current flowing through the driving coil 13 of the force motor 10 according to a vibration signal based on the vibration detected by the vibration detection section 60 so as to deaden influence of vibration (external force) applied from the outside and acting on the indenter shaft 2.

That is, when the indenter shaft 2 (indenter 1) undesirably applies the force based on the vibration to the sample S, the vibration adjustment and control section 72 adjusts the amount of current flowing through the driving coil 13 according to the vibration (vibration signal) detected by the vibration detection section 60 and the condition (program) preset and stored in the ROM 7b of the control section 70 so as to reduce the force applied by the indenter shaft 2 to the sample S through the indenter 1. In contrast, when the force based on the vibration undesirably reduces the force applied to the sample S, the vibration adjustment and control section 72 adjusts the amount of current flowing through the driving coil 13 so as to increase the force applied by the indenter shaft 2 to the sample S through the indenter 1. As described above, the vibration adjustment and control section 72 performs the adjustment and control to apply only the substantial test force to the sample S by adjusting the movement of the indenter shaft 2.

When the indenter shaft 2 is moved toward the sample S (sample stand 100), the repulsion adjustment and control section 73 of the control section 70 performs repulsion adjustment and control to deaden a repulsion force of the supporting springs 3, which acts in the direction opposite to the moving direction of the indenter shaft 2 due to the warp of the supporting springs 3 caused by the maintaining of the posture of the indenter shaft 2, in response to an indenter shaft displacement signal based on the movement of the indenter shaft 2 and detector by the indenter shaft displacement detection section 20.

That is, the repulsion adjustment and control section 73 performs the adjustment and control according to the displacement of the indenter shaft 2 detected by the indenter shaft displacement detection section 20 and the condition (program) preset and stored in the ROM 7b of the control section 70 to apply only the substantial test force to the sample S by adjusting both the amount of current flowing through the driving coil 13 and the movement of the indenter shaft 2 so as to increase the force applied by the indenter shaft 2 to the sample S through the indenter 1 for the purpose of deadening the repulsion force generated due to the warp and deformation of the supporting springs 3.

As described above, the control section 70 (self-weight adjustment and control section 71, vibration adjustment and control section 72 and repulsion force adjustment and control section 73) adjusts the movement of the indenter shaft 2 by adjusting the amount of current flowing through the driving coil 13 of the force motor 10 so as to cancel the external force and the like applied to the indenter shaft 2, and the section 70 adjusts the force applied by the indenter shaft 2 to the sample S through the indenter 1. Therefore, the section 70 adjusts to apply only the substantial test force to the sample S.

Next, an operation of the hardness testing apparatus 41 having the configuration described above will be described.

For example, when a test operational signal based on the performance of the operation of the hardness test in an operation section (not shown) is initially input to the control section 70, the control section 70 supplies an amount of current corresponding to the predetermined test force to the driving coils 13 and 33 of the force motors 10 and 30 and controls the force motor 10 to generate the driving force. Further, the control section 70 performs the adjustment and control (self-weight adjustment and control section 71, vibration adjustment and control section 72 and repulsion force adjustment and control section 73) to apply only the substantial test force to the sample S.

The force motor 10 moves the indenter shaft 2 toward the sample S arranged below the indenter shaft 2 in the axial direction of the indenter shaft 2 to apply the predetermined force (test force) to the sample S through the indenter 1 of the indenter shaft 2 to form a dimple.

Thereafter, the hardness testing apparatus 41 calculates a hardness of the sample S according to the shape (size (length between predetermined positions), depth) of the dimple, the test force by using a hardness calculation formula corresponding to the hardness test and preset and stored in the ROM 7b of the control section 70.

As described above, because the hardness testing apparatus 41 of this embodiment uses the force motor 10 to drive the indenter shaft 2, the indenter shaft 2 is moved to apply a stepless test force to the sample S through the indenter 1 by adjusting the amount of current supplied to (the driving coil 13 of) the force motor 10 in a stepless manner. Therefore, the hardness testing apparatus 41 can perform the hardness test at a desired optional test force (driving force) within range of the output of the force motor 10. That is, the hardness testing apparatus 41 can perform the hardness test at various test forces.

Further, because the control section 70 of the hardness testing apparatus 41 has the self-weight adjustment and control section 71, the vibration adjustment and control section 72 and the repulsion force adjustment and control section 73, the control section 70 can adjust the driving force output from the force motor 10 by adjusting the amount of current supplied to the force motor 10 (driving coil 13) so as to cancel the external force and the like acting on the indenter shaft 2, and the control section 70 can perform the adjustment and control to make the indenter shaft 2 (indenter 1) apply only the substantial test force to the sample S. Accordingly, the hardness testing apparatus 41 can perform the hardness test based on a further accurate test force.

Second Embodiment

Next, a hardness testing apparatus according to the second embodiment of the present invention will be described with reference to FIGS. 3 and 4. The constituent elements indicated by the same reference numerals as those in the first embodiment are the same as those in the first embodiment. Therefore, the description of the constituent elements is omitted.

Figure 3:
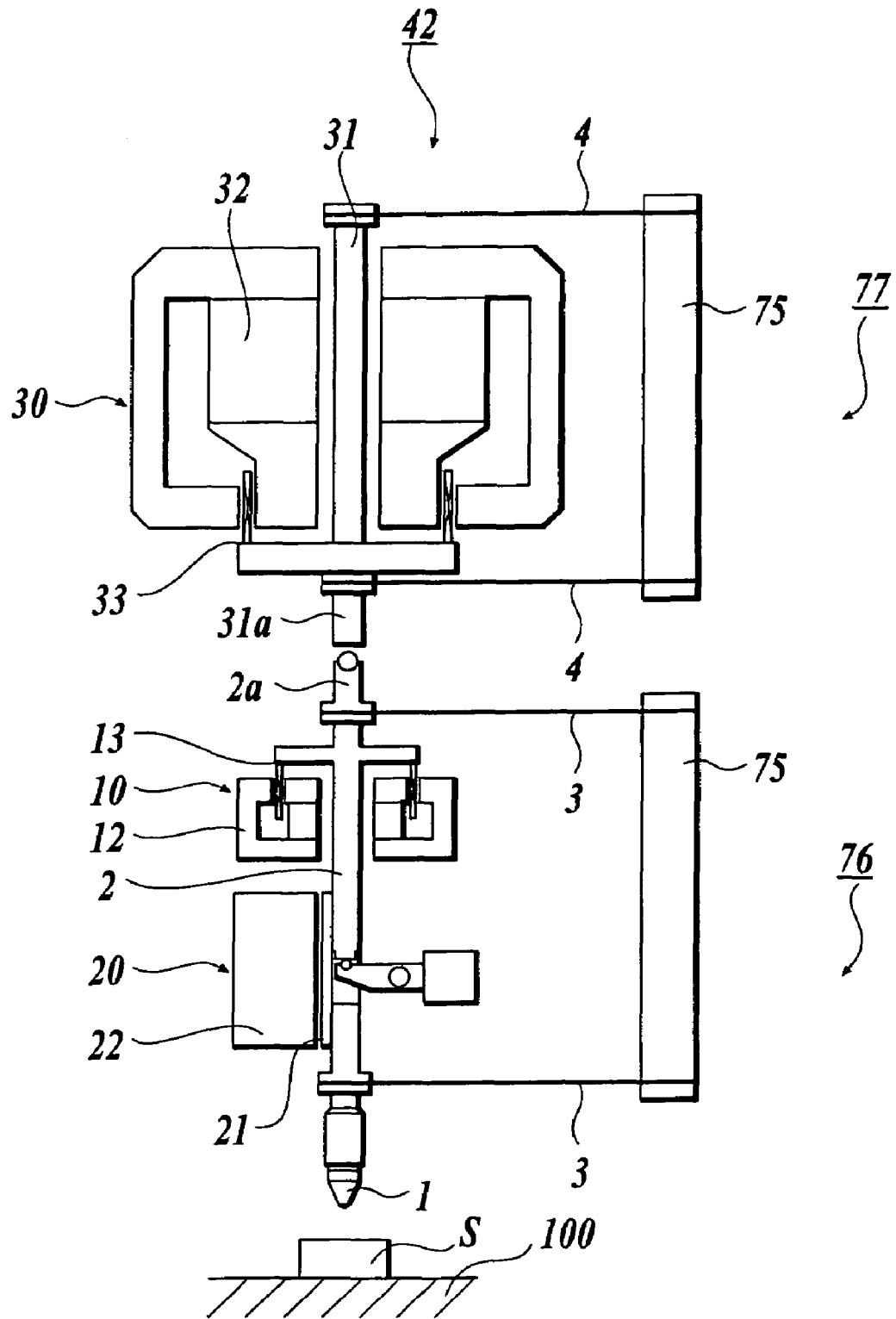
FIG. 3 is a side view in partial cross-section of a hardness testing apparatus according to the second embodiment of the present invention.
Figure 4:
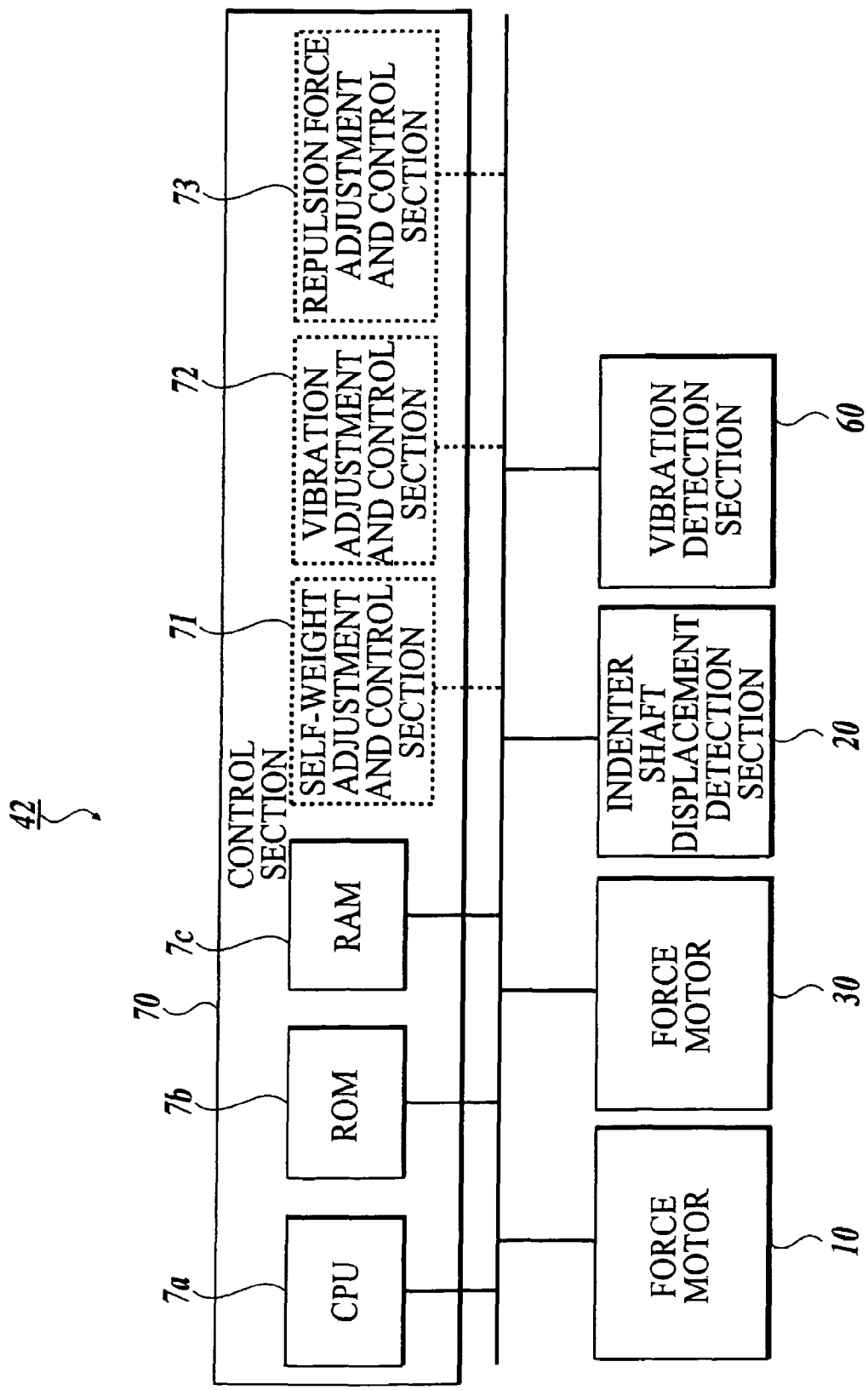
FIG. 4 is a block diagram showing a main section of the hardness testing apparatus according to the second embodiment of the present invention.

FIG. 3 is a side view in partial cross-section of a hardness testing apparatus. FIG. 4 is a block diagram showing a main section of the hardness testing apparatus shown in FIG. 3.

As shown in FIG. 3, a hardness testing apparatus 42 comprises an indenter shaft unit 76 having the indenter shaft 2 and a pushing force applying mechanism 77 for applying a predetermined pushing force to the indenter shaft 2. The indenter shaft 2 has an indenter 1 at the top thereof to form a dimple in the sample S mounted on the sample stand 100.

The indenter shaft unit 76 comprises the supporting springs 3 arranged on the testing apparatus body 75 and acting as an elastic supporting structure, the indenter shaft 2 of which the upper and lower ends are elastically supported by the supporting springs 3 respectively, the force motor 10 acting as a first load applying mechanism for applying a predetermined force to the indenter shaft 2 in an axial direction of the indenter shaft 2 to move the indenter shaft 2 in the axial direction, and the indenter shaft displacement detection section 20 for detecting displacement of the indenter shaft 2.

The force motor 10 can apply various test forces (predetermined test force, force within range of first test force) to the sample S by generating an optional driving force according to an amount of current supplied to the driving coil 13 of the force motor 10 and moving the indenter shaft 2 according to a total driving force.

The pushing force applying mechanism 77 comprises a (second) force motor 30 arranged on the upper side of the indenter shaft unit 76 and acting as a second load applying mechanism, and two supporting springs 4 elastically supporting a load shaft 31 of the force motor 30 on the testing apparatus body 75.

One end of each supporting spring 4 is fixed to the testing apparatus body 75, and the supporting spring 4 extends in the almost horizontal direction from the body 75. The other ends of the supporting springs 4 are connected to the upper and lower ends of the load shaft 31 of the force motor 30 respectively, as described later. The supporting springs 4 elastically support the load shaft 31 coaxially with the indenter shaft 2 and perpendicularly to the sample stand 100. When the load shaft 31 is moved in the upper and lower directions by the force motor 30, the supporting springs 4 are warped so as to maintain the posture of the load shaft perpendicular to the sample stand 100.

The force motor 30 comprises a magnetic circuit structure 32 and a driving coil 33 acting as a pressing member and arranged on the side of the load shaft 31. The force motor 30 generates a force in the magnetic circuit structure 32 by the electromagnetic induction which is based on both a magnetic field induced in a gap by a magnet and a current flowing through the driving coil 33 arranged in the gap. The force motor 30 uses the force as a driving force to move the load shaft 31 in its axial direction and applies a pressing force to the indenter shaft 2 to move the indenter shaft 2 in its axial direction. Thereafter, the force motor 30 applies a predetermined force (second test force) to the sample S through the indenter shaft 2.

That is, the force motor 30 can apply various test forces (forces within a range of second test force) to the sample S by generating an optional driving force according to an amount of current supplied to the driving coil 33 and moving the indenter shaft 2 according to the driving force. Further, when the force motor 30 adjusts the amount of current flowing through the driving coil 33 in a stepless manner, the force motor 30 can output one of stepless driving forces and apply one of stepless test forces (second test force) to the sample S.

The current supplied from the force motor 30 to the driving coil 33 is controlled by the control section 70. The force motor 30 generates the driving force according to an amount of current (and/or a direction of current) predetermined from the predetermined test force, moves the indenter shaft 2 and applies the predetermined test force to the sample S.

The hardness testing apparatus 42 described above has a control section 70 shown in FIG. 4, and the control section 70 is connected to the force motor 10, the force motor 30, the indenter shaft displacement detection section 20, the vibration detection section 60 and the like through a system bus, a driving circuit and the like. Further, the control section 70 has the self-weight adjustment and control section 71, the vibration adjustment and control section 72 and the repulsion force adjustment and control section 73 to be embodied by the cooperation of the CPU 7a with various processing programs stored in the ROM 7b in software processing.

When a test operation signal indicating the performance of the operation of the hardness test is input to in an operation section (not shown), the control section 70 performs an operational control by executing a predetermined program stored in the ROM 7b, supplies an amount of current based on a predetermined test force, which is determined according to predetermined operational conditions (for example, operational condition of indenter shaft 2) preset to perform a predetermined hardness test, to the driving coils 13 and 33 of the force motors 10 and 30, drives the force motors 10 and 30 to move the indenter shaft 2 and applies the predetermined test force to the sample S.

Further, the control section 70 (self-weight adjustment and control section 71, vibration adjustment and control section 72 and repulsion force adjustment and control section 73) adjusts the movement of the indenter shaft 2 by adjusting the amount of current flowing through the driving coils 13 and 33 so as to cancel the external force and the like acting on the indenter shaft 2, and the control section 70 performs the adjustment to make the indenter shaft 2 apply only the substantial test force to the sample S.

Next, an operation of the hardness testing apparatus 42 having the configuration described above will be described.

For example, when a test operational signal based on the performance of the operation of the hardness test in an operation section (not shown) is initially input to the control section 70, the control section 70 supplies an amount of current corresponding to the predetermined test force to the driving coils 13 and 33 of the force motors 10 and 30 and controls the motors 10 and 30 to generate driving forces. Further, the control section 70 performs the adjustment and control (self-weight adjustment and control section 71, vibration adjustment and control section 72 and repulsion force adjustment and control section 73) to apply only the substantial test force to the sample S.

The force motor 10 moves the indenter shaft 2 downward in the axial direction of the indenter shaft 2 to apply the predetermined force (first test force) to the sample S through the indenter 1 of the indenter shaft 2. The force motor 30 applied a pushing force to the indenter shaft 2 by moving the load shaft 31 downward in the axial direction of the load shaft 31 to make the lower end 31a of the load shaft 31 push down the upper end 2a of the indenter shaft 2 and to move the indenter shaft 2 downward in the axial direction of the indenter shaft 2. Thereafter, the force motor 30 applies the predetermined force (second test force) to the sample S through the indenter 1 of the indenter shaft 2.

As described above, the hardness testing apparatus 42 forms a dimple at the test force which is obtained by combining the predetermined force (first test force) applied to the sample S by the force motor 10 and the predetermined force (second test force) applied to the sample S by the force motor 30.

Thereafter, the hardness testing apparatus 42 calculates a hardness of the sample S according to the shape (size (length between predetermined positions), depth) of the dimple, the test force by using a hardness calculation formula corresponding to the hardness test and preset and stored in the ROM 7b of the control section 70.

As described above, because the hardness testing apparatus 42 of this embodiment uses the force motors 10 and 30 to drive the indenter shaft 2, the indenter shaft 2 is moved to apply a stepless test force to the sample S through the indenter 1 by adjusting the amount of current supplied to (the driving coils 13 and 33 of) the force motors 10 and 30 in a stepless manner. Therefore, the hardness testing apparatus 42 can perform the hardness test at a desired optional test force (driving force) within a range of the outputs of the force motors 10 and 30. That is, the hardness testing apparatus 42 can perform the hardness test at various test forces in a wide range.

Further, because the control section 70 of the hardness testing apparatus 42 has the self-weight adjustment and control section 71, the vibration adjustment and control section 72 and the repulsion force adjustment and control section 73, the control section 70 can adjust the driving forces output from the force motors 10 and 30 by adjusting the amount of current supplied to the force motors 10 and 30 (driving coils 13 and 33) so as to cancel the external force and the like acting on the indenter shaft 2, and the control section 70 can perform the adjustment and control to make the indenter shaft 2 (indenter 1) apply only the substantial test force to the sample S. Accordingly, the hardness testing apparatus 42 can perform the hardness test based on the further correct test force.

Moreover, because the hardness testing apparatus 42 can adjust the output test force (driving force) by adjusting the amount of current supplied to the force motors 10 and 30, the moving speed of the indenter shaft 2 (indenter 1) moving toward the sample S and the duration of the applying of the test force from the indenter 1 arranged on the indenter shaft 2 to the sample S can be selected and adjusted.

Furthermore, the hardness testing apparatus 42 can perform the hardness test at the test force which is obtained by combining the test force (driving force) based on the force motor 10 and the test force (driving force) based on the force motor 30. Accordingly, the hardness testing apparatus 42 can perform the hardness test at the test force which is obtained by combining the test forces (driving force) output from the force motors 10 and 30 respectively. That is, the hardness testing apparatus 42 can perform the hardness test by various test forces in further a wide range.

For example, when the test force (driving force) output from the force motor 30 is almost the same as that output from the force motor 10, the test force output by combining the forces of the force motors 10 and 30 can become almost twice that compared with the use of the single force motor.

Further, when one force motor is appropriate to the outputting of a large test force (driving force) and the other force motor is appropriate to the outputting of a small test force (driving force), the hardness testing apparatus 42 can output further changeable test forces in a further wide range.

Moreover, when the hardness testing apparatus 42 adjusts the amount of current supplied to the driving coils 13 and 33 of the force motors 10 and 30 so as to balance the amount of current with a dead weight such as a known weight while weighting a load shaft (load shaft 31, indenter shaft 2) with the dead weight, the correlation of the amount of current and the driving force output from the force motors can be ascertained. Accordingly, because the driving force (test force) output from the force motors can be revised in the hardness testing apparatus 42, further accurate hardness test can be performed.

It is preferable that each of two force motors (force motor 10, force motor 30) perform the output control and adjustment control of the test force to perform the hardness test at a predetermined test force in the hardness testing apparatus 42. Further, it is preferable that one force motor (for example, force motor 30) perform the output control of the test force moving the load shaft so as to output a predetermined force and the other force motor (for example, force motor 10) performs the adjustment and control to cancel a force which acts on the indenter shaft 2 to deaden the test force applied to the indenter shaft 2.

Third Embodiment

Next, a hardness testing apparatus according to the third embodiment of the present invention will be described with reference to FIGS. 5 and 6. The constituent elements indicated by the same reference numerals as those in the first and second embodiments are the same as those in the first embodiment. Therefore, the description of the constituent elements is omitted.

Figure 5:
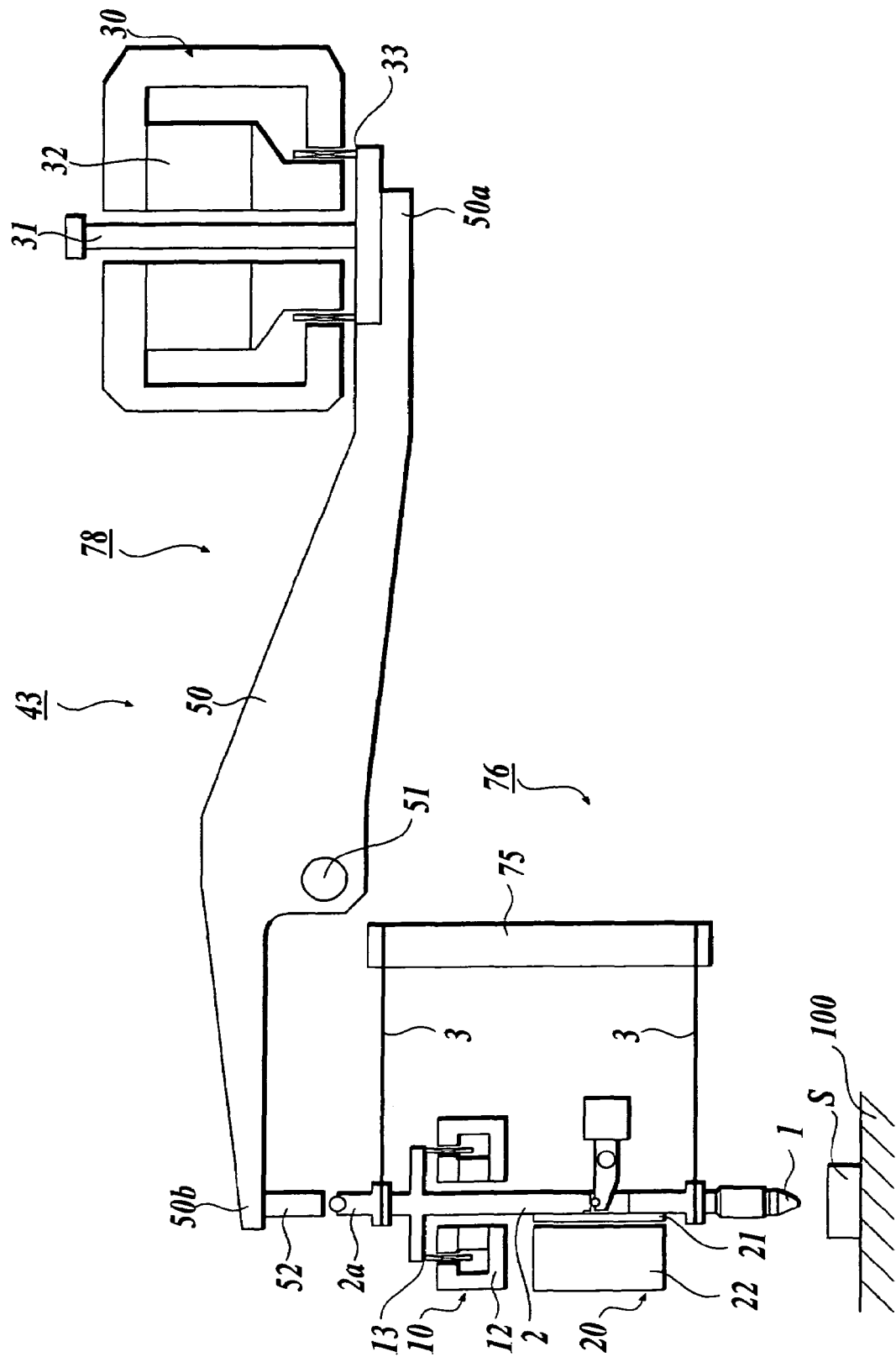
FIG. 5 is a side view in partial cross-section of a hardness testing apparatus according to the third embodiment of the present invention.
Figure 6:
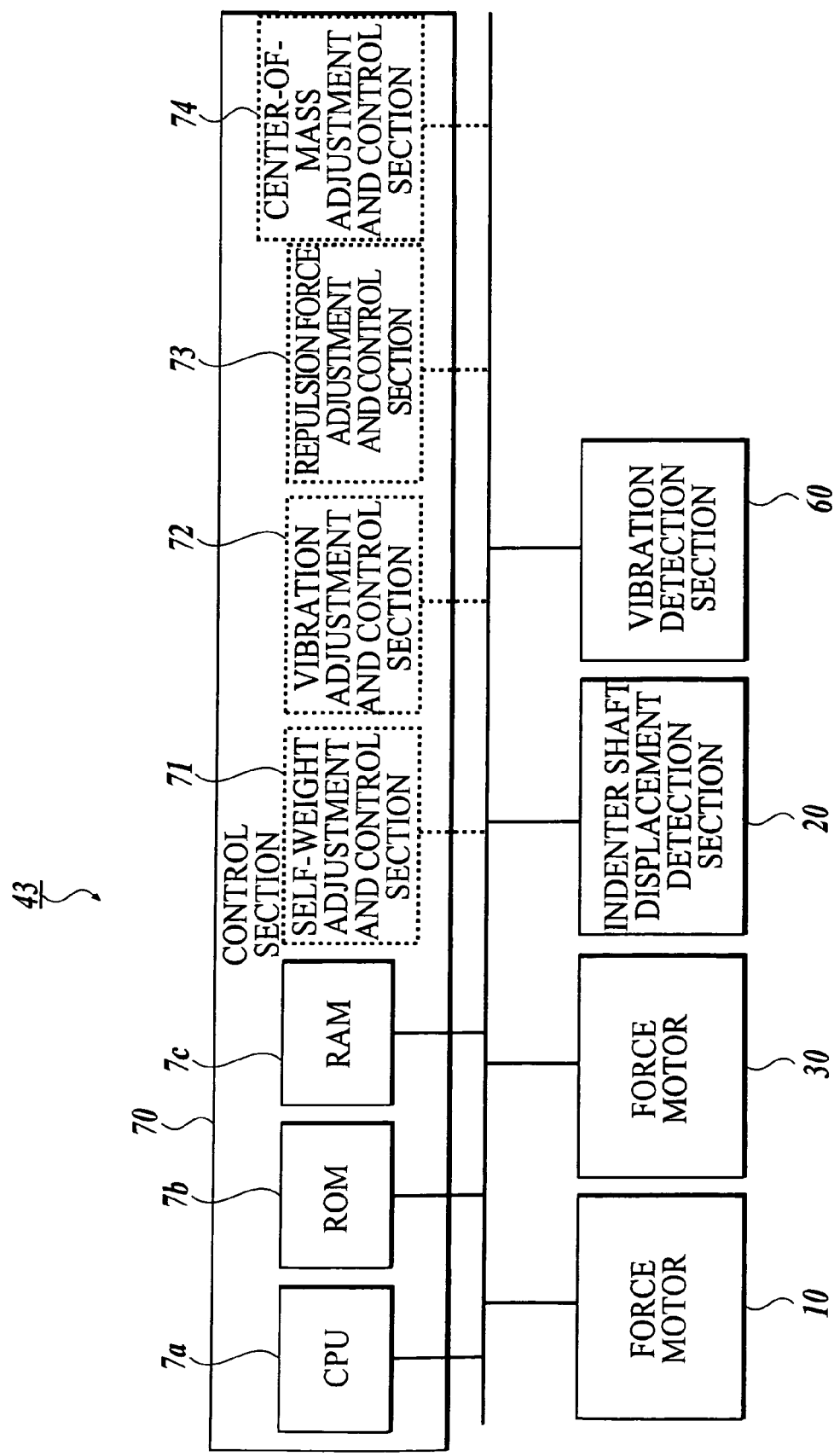
FIG. 6 is a block diagram showing a main section of the hardness testing apparatus according to the third embodiment of the present invention.

FIG. 5 is a side view in partial cross-section of a hardness testing apparatus according to the third embodiment of the present invention. FIG. 6 is a block diagram showing section of the hardness testing apparatus shown in FIG. 5.

As shown in FIG. 5, a hardness testing apparatus 43 comprises the indenter shaft unit 76 having the indenter shaft 2 and a pushing force applying mechanism 78 for applying a predetermined pushing force to the indenter shaft 2.

The pushing force applying mechanism 78 comprises a control lever 50 arranged above the indenter shaft unit 76 and acting as a pushing member, and the force motor 30 applying an action force to the control lever 50 and acting as a second force motor.

The control lever 50 is rotatably supported on a body (not shown) of the testing apparatus by a rotational shaft 51 at the almost center of the control lever 50. The force motor 30 is attached to an end 50a of the control lever 50. The control lever 50 extends from the force motor 30 to the rotational shaft 51, and further to the indenter unit 76, where another end 50b of the control lever 50 is placed above the indenter shaft 2. A pushing member 52 is arranged at the end 50b to push down the upper end 2a of the indenter shaft 2 of the indenter shaft unit 76.

In the force motor 30, a force generated in the magnetic circuit structure 32 by electromagnetic induction, which is based on both a magnetic field induced in a gap by a magnet and a current flowing through the driving coil 33 arranged in the gap, is used as a driving force. The force motor 30 moves the load shaft 31 in its axial direction by the driving force and applies an action force to the end 50a of the control lever 50 to rotate the control lever 50. The force motor 30 makes the other end 50b of the control lever 50 incline downward and pushes down the indenter shaft 2 in its axial direction by the pushing member 52 arranged on the end 50b.

The hardness testing apparatus 43 described above has a control section 70 shown in FIG. 6, and the control section 70 is connected to the force motor 10, the force motor 30, the indenter shaft displacement detection section 20, the vibration detection section 60 and the like through a system bus, a driving circuit and the like. Further, the control section 70 has the self-weight adjustment and control section 71, the vibration adjustment and control section 72, the repulsion force adjustment and control section 73 and a center-of-mass adjustment and control section 74 to be embodied by cooperation of the CPU 7a with various processing programs stored in the ROM 7b in software processing.

The center-of-mass adjustment and control section 74 of the control section 70 performs the center-of-mass adjustment and control according to data of an amount of movement (amount of inclination) of the control lever 50 stored in the ROM 7b of the control section 70b to adjust an amount of current flowing through the driving coils 13 and 33 of the force motors 10 and 30 so as to deaden the influence (force) based on the self-weight of the control lever 50 acting on the indenter shaft 2 due to the movement of the center-of-mass of the control lever 50.

That is, when the center-of-mass of the control lever 50 is displaced due to the movement and inclination of the control lever 50 to give a moment force to the indenter shaft, 2, the center-of-mass adjustment and control section 74 adjust the amount of current flowing through the driving coils 13 and 33 to reduce the force applied by the indenter shaft 2 to the sample S through the indenter 1. In contrast, when the control lever 50 cancels out a moment force applied to the indenter shaft 2, the center-of-mass adjustment and control section 74 adjust the amount of current flowing through the driving coils 13 and 33 to increase the force applied by the indenter shaft 2 to the sample S through the indenter 1. Therefore, the center-of-mass adjustment and control section 74 performs the adjustment and control to make the indenter shaft 2 apply only the predetermined substantial test force to the sample S by adjusting the movement of the indenter shaft 2.

When a test operational signal based on the performance of the operation of the hardness test is initially input to an operation section (not shown), the control section 70 performs operational control by executing a predetermined program stored in the ROM 7b according to a predetermined operational condition (for example, operational condition of the indenter shaft 2) preset to perform a predetermined hardness test to supply an amount of current corresponding to the predetermined test force to the driving coils 13 and 33 of the force motors 10 and 30, move the indenter shaft 2 by driving the force motors 10 and 30 and apply a predetermined test force to the sample S.

Further, the control section 70 (self-weight adjustment and control section 71, vibration adjustment and control section 72, repulsion force adjustment and control section 73 and center-of-mass adjustment and control section 74) adjusts the movement of the indenter shaft 2 to deaden the external force acting on the indenter shaft 2 by adjusting the amount of current flowing through the driving coils 13 and 33 of the force motors 10 and 30 and performs the adjustment to make the indenter shaft 2 (or the indenter 1) apply only the predetermined substantial test force to the sample S.

Next, an operation of the hardness testing apparatus 43 having the configuration described above will be described.

For example, when a test operational signal based on the performance of the operation of the hardness test in an operation section (not shown) is initially input to the control section 70, the control section 70 supplies an amount of current corresponding to the predetermined test force to the driving coils 13 and 33 of the force motors 10 and 30 and controls the force motors 10 and 30 to generate driving forces. Further, the control section 70 performs the adjustment and control (self-weight adjustment and control section 71, vibration adjustment and control section 72, repulsion force adjustment and control section 73 and center-of-mass adjustment and control section 74) to apply only the substantial test force to the sample S.

The force motor 10 moves the indenter shaft 2 downward in the axial direction of the indenter shaft 2 to apply the predetermined force (first test force) to the sample S through the indenter 1 of the indenter shaft 2.

The force motor 30 rotates the control lever 50 to move the end 50a of the control lever 50 upward by moving the load shaft 31 in its axial direction. Thereafter, the force motor 30 makes the pushing member 52 arranged on the other end 50b of the control lever 50 push down the upper end 2a of the indenter shaft 2 by moving the other end 50b downward and move the indenter shaft 2, and the force motor 30 applies a predetermined force (second test force) to the sample S through the indenter 1 of the indenter shaft 2. That is, the force motor 30 applies the pressing force to the indenter shaft 2 through the control lever 50 and makes the indenter 1 of the indenter shaft 2 apply the pressing force to the sample S by moving the indenter shaft 2 downward in its axial direction.

As described above, the hardness testing apparatus 43 forms a dimple by the test force which is obtained by combining the predetermined force (first test force) applied to the sample S by the force motor 10 and the predetermined force (second test force) applied to the sample S by the force motor 30.

Thereafter, the hardness testing apparatus 43 calculates a hardness of the sample S according to the shape (size (length between predetermined positions), depth) of the dimple, the test force by using a hardness calculation formula corresponding to the hardness test and preset and stored in the ROM 7b of the control section 70.

As described above, the hardness testing apparatus 43 can perform the hardness test at the test force, which is obtained by combining the driving force based on the force motor 10 and the driving force based on the force motor 30, by using the force motors 10 and 30 to drive the indenter shaft 2. Accordingly, because the hardness testing apparatus 43 can perform the hardness test at the test force (driving force) which is obtained by combining the driving forces output from the force motors 10 and 30 respectively, the hardness testing apparatus 43 can perform the hardness test at various test forces in a further wide range.

Particularly, because the driving force output from the force motor 30 is transmitted through the control lever 50 rotated on the rotational shaft 51, even in the case of a small driving force, the driving force can be applied to the indenter shaft 2 as a larger test force (pressing force) by using so-called "principle of lever".

In the hardness testing apparatuses 41, 42 and 43, because the force motor 10 or the force motors 10 and 30 are used, each hardness testing apparatus can apply a stepless test force to the sample S through the indenter 1 of the indenter shaft 2 by adjusting the amount of current supplied to the driving coil(s) of the force motor(s). Accordingly, the hardness testing apparatuses 41, 42 and 43 can perform the hardness test at the desired optional test force according to the adjustable test force in a stepless manner within a range of the output(s) of the force motor(s). That is, the hardness testing apparatuses 41, 42 and 43 can perform the hardness test at various test forces.

Further, because the control section 70 of each hardness testing apparatus has adjustment and control sections such as the self-weight adjustment and control section 71, the vibration adjustment and control section 72, the repulsion force adjustment and control section 73, the center-of-mass adjustment and control section 74 and the like, when the control section 70 adjusts the driving forces output from the force motors 10 and 30 so as to deaden the external force and the like acting on the indenter shaft 2, the control section 70 can perform the adjustment and control to adjust the amount of current supplied to the force motors 10 and 30 (driving coils 13 and 33) and to make the indenter shaft 2 (indenter 1) apply only the predetermined substantial test force to the sample S. Accordingly, the hardness testing apparatuses 41, 42 and 43 can perform the hardness test based on the further correct test force.

Moreover, the hardness testing apparatuses 42 and 43 can perform the hardness test based on the test force, which is obtained by combining the test force based on the force motor 10 and the test force based on the force motor 30, by using the two force motors 10 and 30. Accordingly, the hardness testing apparatuses 42 and 43 can perform the hardness test obtained by combining the test forces (first test force, second test force) output from two force motors and can perform the hardness test at various test forces in a further wide range.

In the first to third embodiments, the indenter shaft 2 is moved by using the force motor(s). However, the hardness testing apparatus according to this invention is not limited to this. A load applying mechanism acting as the force motor(s) may be arranged on condition that the stepless load or test force applied to the sample S by moving the indenter shaft 2 is adjustable.

Further, the self-weight adjustment and control section 71, the vibration adjustment and control section 72, the repulsion force adjustment and control section 73 and the center-of-mass adjustment and control section 74 are embodied by the cooperation of the CPU 7a with various processing programs stored in the ROM 7b in software processing. However, the adjustment and control sections 71 to 74 may be embodied by private hardware which is operated under control of the CPU 7a so as to perform the function of the processing programs.

Further, minute structures of the apparatuses can be appropriately changed.

Fourth Embodiment

Figure 7:
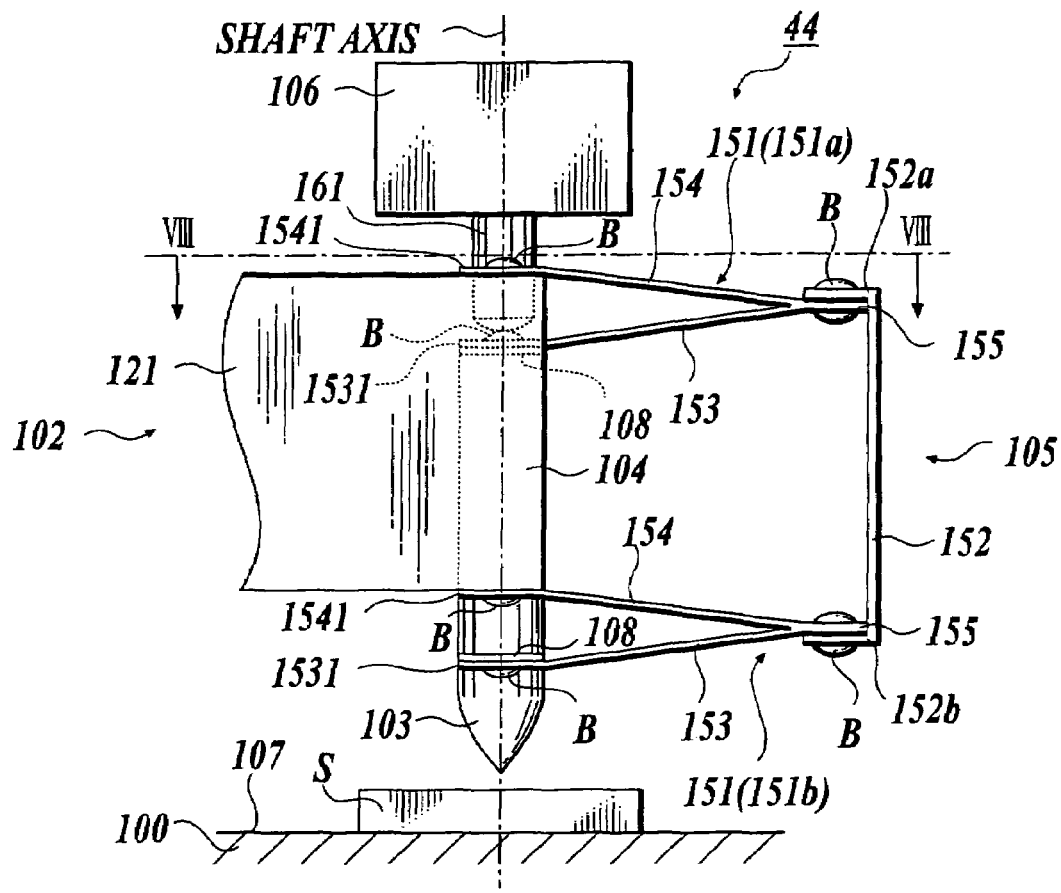
FIG. 7 is a side view showing a main part of a hardness testing apparatus according to the fourth embodiment of the present invention.
Figure 8:
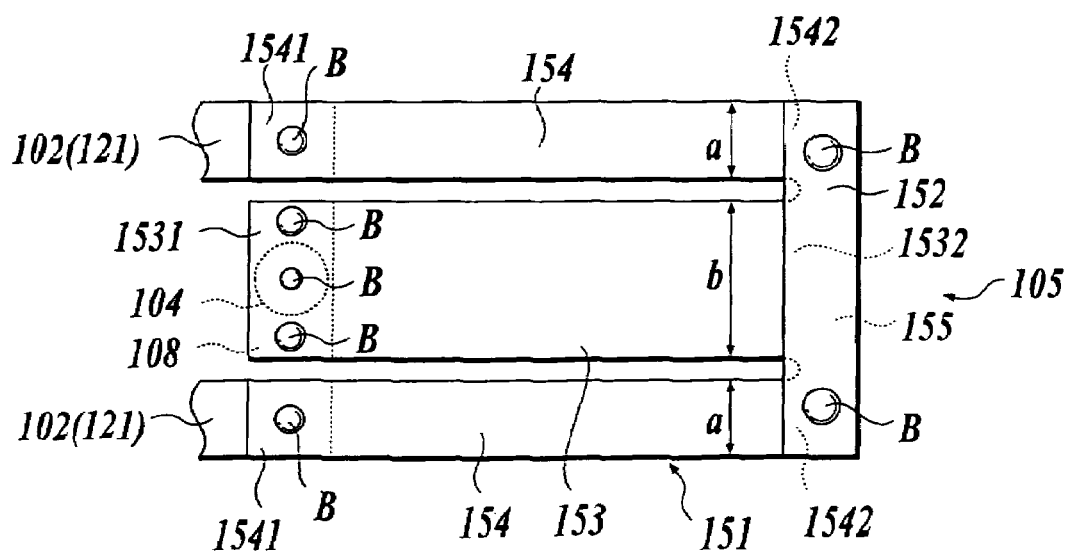
FIG. 8 is a plan view seen from line VIII-VIII of FIG. 7.

FIG. 7 is a side view showing a main part of a hardness testing apparatus according to the fourth embodiment of the present invention. FIG. 8 is a plan view seen from line VIII-VIII of FIG. 7.

As shown in FIGS. 7 and 8, a hardness testing apparatus 44 comprises a testing apparatus body 102 having an indenter shaft attaching member 121, an indenter shaft 104 changeably having an indenter 103 at the top (lower end) of the shaft 104, a supporting structure 105 for elastically supporting the indenter shaft 104 to be moveable in its axial direction and to be attached to the indenter shaft attaching member 121 of the testing apparatus body 102, a load applying mechanism 106 for applying a predetermined force to the indenter shaft 104 in its axial direction, and the sample stand 100 having a mounting surface 107 for mounting the sample S.

The supporting structure 105 comprises two upper and lower folding springs 151 (151a, 151b) for connecting the indenter shaft attaching member 121 to the indenter shaft 104 at upper and lower ends of the indenter shaft 104 respectively, and a connecting member 152 connecting the folding springs 151 to each other.

As shown in FIG. 8, each folding spring 151 comprises a middle plate spring 153 extending to the left of the drawing to have an end 1531 on the left and acting as a first elastic member, and two outer plate springs 154 arranged on both sides of the middle plate spring 153 (upper and lower sides of the middle plate spring 153 in the drawing), extending to the left of the drawing to have an end 1541 on the left and acting as a second elastic member. Another end 1532 of the middle plate spring 153 is integrally connected to other ends 1542 of the outer plate springs 154 on the right of the drawing at a spring end 155 acting as a connecting portion. The folding spring 151 is formed in E shape in plan view.

Width b (length in the vertical direction of the drawing) of the middle plate spring 153 is set to be almost twice of width a (length in the vertical direction of the drawing) of the outer plate spring 154. That is, length and thickness of the middle plate spring 153 are the almost same as those of each outer plate spring 154, and the width of the middle plate spring 153 is substantially the same as that of the combination of the outer plate springs 154. Therefore, the spring constant of the middle plate spring 153 is the almost same as that of the combination of the outer plate springs 154.

As shown in FIG. 7, the middle plate spring 153 of the folding spring 151 is inclined so as to place the end 1531 to the lower left of the spring 153 in the drawing. The outer plate spring 154 of the folding spring 151 is inclined so as to place the end 1541 to the upper left of the spring 154 in the drawing. The folding spring 151 is formed in almost V shape in side view.

In the upper folding spring 151a, the end 1531 of the middle plate spring 153 is fixed to the upper end of the indenter shaft 104 by bolts B, and the ends 1541 of the outer plate springs 154 are fixed to the upper surface of the indenter shaft attaching member 121 by bolts B.

In the lower folding spring 151b, the end 1531 of the middle plate spring 153 is fixed to a portion between the lower end of the indenter shaft 104 and the indenter 103 by bolts B, and the ends 1541 of the outer plate springs 154 are fixed to the lower surface of the indenter shaft attaching member 121 by bolts B.

The folding springs 151 adjacent to each other are connected to each other by the connecting member 152.

The connecting member 152 is made of non-magnetic conductor such as aluminum, copper or the like. As shown in FIG. 7, the connecting member 152 is formed in almost U shape in side view. The spring end 155 of the upper folding spring 151a is fixed to the upper end 152a of the connecting member 152 by bolts B, and the spring end 155 of the lower folding spring 151b is fixed to the lower end 152b of the connecting member 152 by bolts B. The connecting member 152 connects the upper folding spring 151a and the lower folding spring 151b.

In each folding spring 151, the other end 1532 of the middle plate spring 153 and the other ends 1542 of the outer plate springs 154 are connected to each other to have a supporting point by fixing the spring end 155 of the folding spring 151 to the upper or lower end 152a or 152b of the connecting member 152.

The indenter shaft 104 is attached to the testing apparatus body 102 (indenter shaft attaching member 121) through the folding springs 151 so as to make the axial direction of the indenter shaft 104 be perpendicular to the mounting surface 107 of the sample stand 100, and the indenter shaft 104 is elastically supported by the folding springs 151.

As shown in FIG. 7, the connecting member 152 is arranged so as to make the extending direction of the connecting member 152 be parallel to the axial direction of the indenter shaft 104.

The load applying mechanism 106 is, for example, a force motor or the like. The mechanism 106 uses a force, as a driving force, generated in a magnetic circuit structure (not shown) of the force motor by electromagnetic induction which is based on both a magnetic field induced in a gap by a magnet and a current flowing through a driving coil arranged in the gap. The mechanism 106 applies a predetermined force (load) to the indenter shaft 104 by moving a load shaft 161 of the load applying mechanism 106 in its axial direction.

Next, an operation of each section of the hardness testing apparatus 44 in the hardness test will be described.

The sample S is initially mounted on the mounting surface 107 of the sample stand 100, and an operational section (not shown) is operated to perform the hardness test of the hardness testing apparatus 44. Thereafter, a control section (not shown) supplies a predetermined amount of current to the load applying mechanism 106 according to the input to the operational section, and the load applying mechanism 106 is operated.

The load shaft 161 is moved downward according to the operation of the load applying mechanism 106, and the load applying mechanism 106 (load shaft 161) applies a predetermined force (load) to the indenter shaft 104 to move the indenter shaft 104 in its axial direction.

The indenter shaft 104 is moved downward while deforming the folding springs 151 of the supporting structure 105, pushes the indenter 103 to the surface of the sample S at the predetermined force (load) and forms a dimple.

Thereafter, the apparatus 44 performs the test of measuring a hardness of the sample S, for example, Vickers hardness test according to the dimple formed by the indenter 103 (indenter shaft 104) in the sample S.

Next, the movement of the indenter shaft 104 and the motion of the folding springs 151 of the supporting structure 105 caused by the movement of the indenter shaft 104 in the hardness test of the hardness testing apparatus 44 will be described with reference to FIGS. 9A and 9B.

Figure 9A:
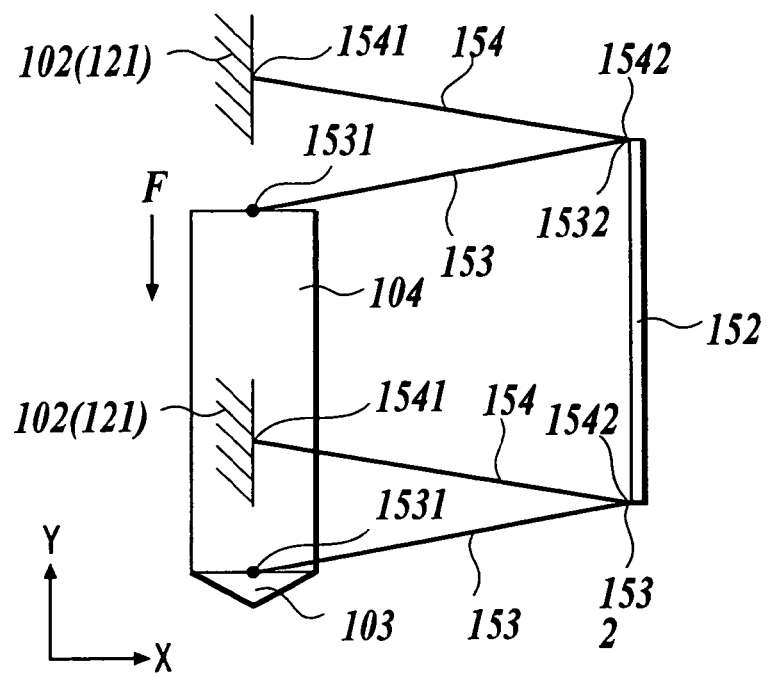
FIG. 9A-B are side views schematically showing operation states of a supporting structure of the hardness testing apparatus according to the fourth embodiment of the present invention.
Figure 9B:
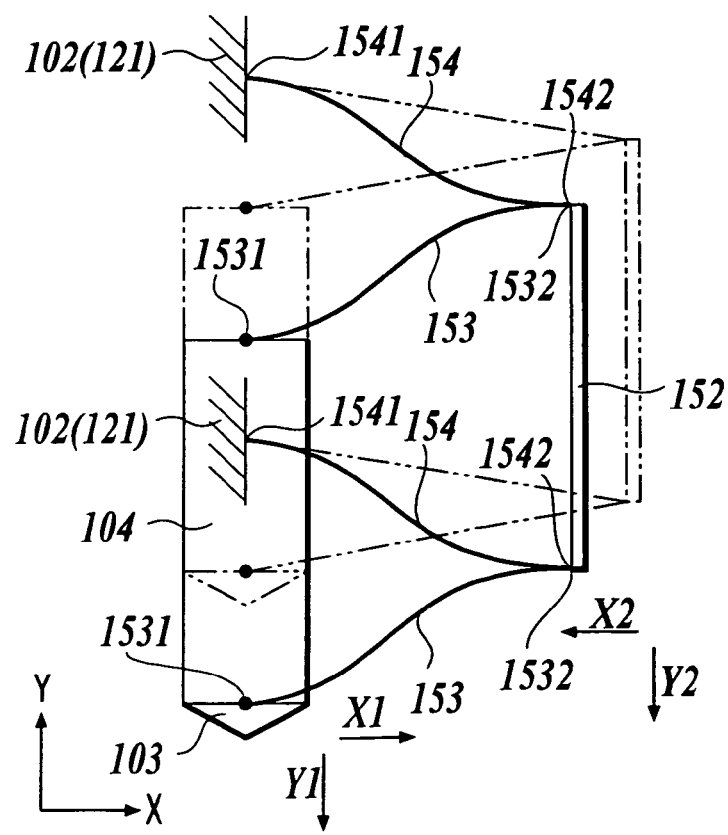

As shown in FIGS. 9A and 9B, when the load applying mechanism 106 applies the predetermined force (load) F to the indenter shaft 104, the indenter shaft 104 is moved downward. The middle plate springs 153, of which the ends 1531 are fixed to the indenter shaft 104, are elastically deformed and warped due to the movement of the indenter shaft 104.

Due to the elastic deformation of the middle plate springs 153, a Y-axis directional moment parallel to the axial direction of the indenter shaft 104 and an X-axis directional moment perpendicular to the Y-axis are generated. As shown in FIG. 9B, the Y-axis directional moment in the middle plate springs 153 acts to move the indenter shaft 104 in its axial direction (Y-axis direction) (refer to arrow Y1 in FIG. 9B). The X-axis directional moment in the middle plate springs 153 acts to move the indenter shaft 104 fixed to the ends 1531 of the middle plate springs 153 to the side of the other ends 1532 (connecting member 152) of the middle plate springs 153 (refer to arrow X1 in FIG. 9B).

Because the other ends 1532 of the middle plate springs 153 are connected to the other ends 1542 of the outer plate springs 154 though the connecting member 152 in the hardness testing apparatus 44, the moments generated by the movement of the indenter shaft 104 are transmitted to the outer plate springs 154 through the connecting member 152. Therefore, the outer plate springs 154 are also elastically deformed, and an X-axis directional moment and a Y-axis directional moment are generated in the outer plate springs 154. As shown in FIG. 9B, the Y-axis directional moment in the outer plate springs 154 acts to move the connecting member 152 downward (Y-axis direction) (refer to arrow Y2 in FIG. 9B), and the X-axis directional moment in the outer plate springs 154 acts to move the connecting member 152 fixed to the other ends 1542 of the outer plate springs 154 to the side of the ends 1541 (testing apparatus body 102) of the outer plate springs 154 (refer to arrow X2 in FIG. 9B).

Particularly, because the ends 1541 of the outer plate springs 154 are fixed to the testing apparatus body 102 (indenter shaft attaching member 121), the X-axis directional moment generated by the elastic deformation of the outer plate springs 154 acts to draw the ends 1542 (connecting member 152) toward the testing apparatus body 102.

Further, because the spring constant of the middle plate spring 153 is almost the same as that of the combination of the two outer plate springs 154, the elastic deformation of the middle plate spring 153 due to the moments caused by the movement of the indenter shaft 104 is similar to that of the combination of the outer plate springs 154. That is, as shown in FIG. 9B, the middle plate spring 153 having the end 1531 placed at the lower position is symmetric with the outer plate spring 154 having the other end 1542 placed at the lower position with respect to a central line between the plate springs 153 and 154 in side view, and the amount of displacement of the middle plate spring 153 in the X-axis direction and the amount of displacement of the middle plate spring 153 in the Y-axis direction are the same as those of the outer plate springs 154.

Therefore, as shown in FIG. 9B, because the X-axis directional moment due to the warp of the two outer plate springs 154 cancels out the X-axis directional moment due to the warp of the middle plate spring 153, the displacement of the shaft axis of the indenter shaft 104 to the direction perpendicular to the axial direction of the indenter shaft 104 due to the warp of the two outer plate springs 154 cancels out that due to the warp of the middle plate spring 153, and the indenter shaft 104 is moved in the Y-axis direction. That is, the apparatus 44 has the configuration that the indenter shaft 104 is not moved in the X-axis direction but is selectively moved in the Y-axis direction by relatively moving the supporting structure 105 (connecting member 152) to the side of the indenter shaft 104.

As described above, in the hardness testing apparatus 44, the other ends 1542 of the outer plate springs 154, of which the ends 1541 are fixed to the testing apparatus body 102, are connected to the other ends 1532 of the middle plate springs 153 of which the ends 1531 are connected to the indenter shaft 104. Therefore, the displacement of the indenter shaft 104 to the direction perpendicular to the axial direction of the indenter shaft 104 due to the warp of the two outer plate springs 154 can cancel out that due to the warp of the middle plate spring 153. Therefore, the indenter 103 of the indenter shaft 104 can be pushed to the surface of the sample S in the axial direction of the indenter shaft 104. Accordingly, a further accurate dimple can be formed on the surface of the sample S by the indenter 103, and the measuring test of the hardness of the sample S can be performed with further accuracy.

Particularly, in the hardness testing apparatus 44, the folding springs 151 are elastically connected to the upper and lower ends of the indenter shaft 104 and the testing apparatus body 102 (indenter shaft attaching member 121) through the middle plate springs 153 and the outer plate springs 154, and the upper and lower folding springs 151 are connected to each other through the connecting member 152 of which the axial direction is parallel to that of the indenter shaft 104. As described above, because the connecting member 152 connecting the indenter shaft 104 and the testing apparatus body 102 are connected to each other through the connecting member 152 of which the axial direction is parallel to that of the indenter shaft 104, the inclination of the shaft axis of the indenter shaft 104 can be easily prevented. Accordingly, when the indenter shaft 104 is moved in its axial direction, the axial direction can be easily maintained to be perpendicular to the mounting surface 107 of the sample stand 100, the shaft axis of the indenter shaft 104 is hardly displaced, and the dimple can be formed with further accuracy.

Further, when shapes of the middle plate spring 153 and the outer plate springs 154 in each folding spring 151 are adjusted, the spring constant and the warp can be easily adjusted. Accordingly, when the shape of the middle plate spring 153 is set to be substantially the same as that of the two outer plate springs 154, the spring constant and the warp in the middle plate spring 153 can be adjusted to be almost the same as that in the two outer plate springs 154.

First Modification

Next, the first modification of the fourth embodiment will be described with reference to FIG. 10. The constituent elements indicated by the same reference numerals as those in the fourth embodiment are the same as those in the fourth embodiment. Therefore, the description of the constituent elements is omitted.

Figure 10:
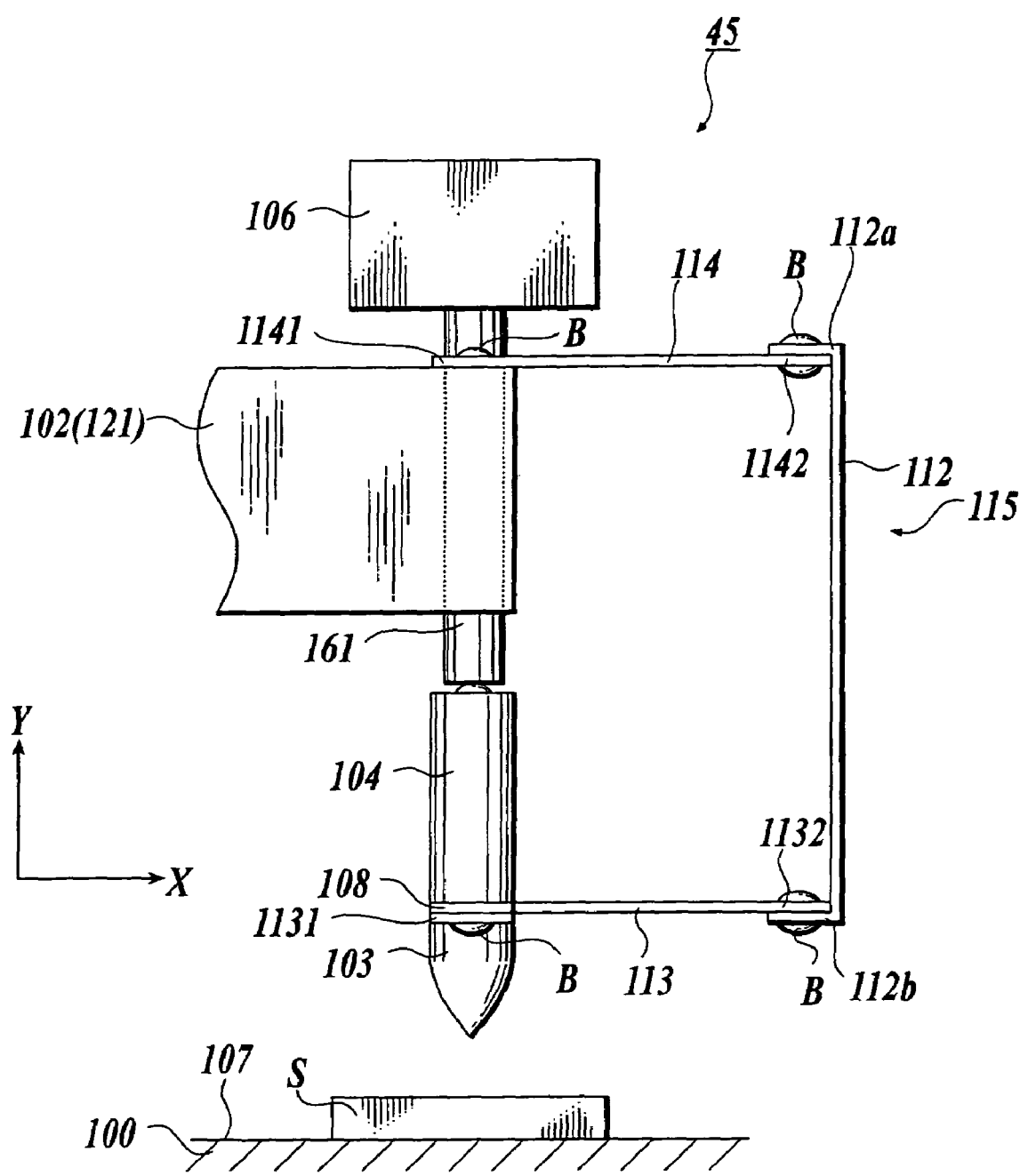
FIG. 10 is a side view showing a main part of a hardness testing apparatus according to the first modification of the fourth embodiment of the present invention.

FIG. 10 is a side view showing a main part of a hardness testing apparatus according to the first modification.

As shown in FIG. 10, a hardness testing apparatus 45 comprises the testing apparatus body 102 having the indenter shaft attaching member 121, the indenter shaft 104 changeably having the indenter 103 at the top (lower end) of the shaft 104, a supporting structure 115 for elastically supporting the indenter shaft 104 to be movably in its axial direction and to be attached to the indenter shaft attaching member 121 of the testing apparatus body 102, the load applying mechanism 106 for applying a predetermined force to the indenter shaft 104 in its axial direction, and the sample stand 100 having the mounting surface 107 for mounting the sample S.

The supporting structure 115 comprises a plate spring 113 acting as a first elastic member, a plate spring 114 acting as a second elastic member, and a connecting member 112. An end 1131 of the plate spring 113 is fixed to a portion between the lower end of the indenter shaft 104 and the indenter 103 through a fixed plate 108 by bolts B. An end 1141 of the plate spring 114 is fixed to the upper surface of the indenter shaft attaching member 121 by bolts B. The connecting member 112 connects another end 1132 of the plate spring 113 and another end 1142 of the plate spring 114.

The shape and spring constant of the plate spring 113 are substantially the same as those of the plate spring 114.

As shown in FIG. 10, the connecting member 112 is formed in an almost U shape in side view. The end 1142 of the plate spring 114 is fixed to an upper end 112a of the connecting member 112 by bolts B, and the end 1132 of the plate spring 113 is fixed to a lower end 112b of the connecting member 112 by bolts B. The connecting member 112 connects the plate spring 113 and the plate spring 114.

The indenter shaft 104 is attached to the testing apparatus body 102 (indenter shaft attaching member 121) through the supporting structure 115 so as to set the axial direction of the indenter shaft 104 perpendicular to the mounting surface 107 of the sample stand 100, and the indenter shaft 104 is elastically supported by the supporting structure 115. As shown in FIG. 10, the connecting member 112 is arranged to make the extending direction of the connecting member 112 be parallel to the axial direction (shaft axis) of the indenter shaft 104.

In the hardness testing apparatus 45, the load applying mechanism 106 applies a predetermined force (load) to the indenter shaft 104, and the indenter shaft 104 is moved downward. The plate spring 113, of which the end 1131 is fixed to the indenter shaft 104, is elastically deformed and warped due to the movement of the indenter shaft 104. The moment caused by the warp of the plate spring 113 is transmitted to the plate spring 114 through the connecting member 112, and the plate spring 114 is also elastically deformed. Because the shape and spring constant of the plate spring 114 are substantially the same as those of the plate spring 113, the plate springs 113 and 114 are elastically deformed in the same manner as the middle plate spring 153 and the outer plate spring 154 so as to make the deformed shapes of the plate springs 113 and 114 in side view be similar to and symmetric with each other with respect to a central line of the plate springs 113 and 114. An amount of displacement caused by the elastic deformation of the plate spring 113 in the X-axis direction is almost the same as that in the plate spring 114, and the direction of the displacement in the plate spring 113 is opposite to that in the plate spring 114. Therefore, the displacements of the plate springs 113 and 114 in the X-axis direction cancel each other out. Because the movement of the indenter shaft 104 in the X-axis direction is prevented, the indenter shaft 104 is moved in the Y-axis direction according to the displacements caused in the Y-axis direction by the deformation of the plate springs 113 and 114. That is, the apparatus 45 has the configuration that the indenter shaft 104 is not moved in the X-axis direction but is selectively moved in the Y-axis direction by relatively moving the supporting structure 115 (connecting member 112) to the side of the indenter shaft 104.

Therefore, in the hardness testing apparatus 45 having the supporting structure 115, the indenter 103 of the indenter shaft 104 can be pushed to the surface of the sample S in the direction of the indenter shaft 104. Accordingly, a dimple can be formed on the surface of the sample S by the indenter 103 with further accuracy, and the measuring test of the hardness of the sample S can be performed with further accuracy.

Second Modification

The second modification of the fourth embodiment will be described with reference to FIG. 11. The constituent elements indicated by the same reference numerals as those in the fourth embodiment are the same as those in the fourth embodiment. Therefore, the description of the constituent elements is omitted.

Figure 11:
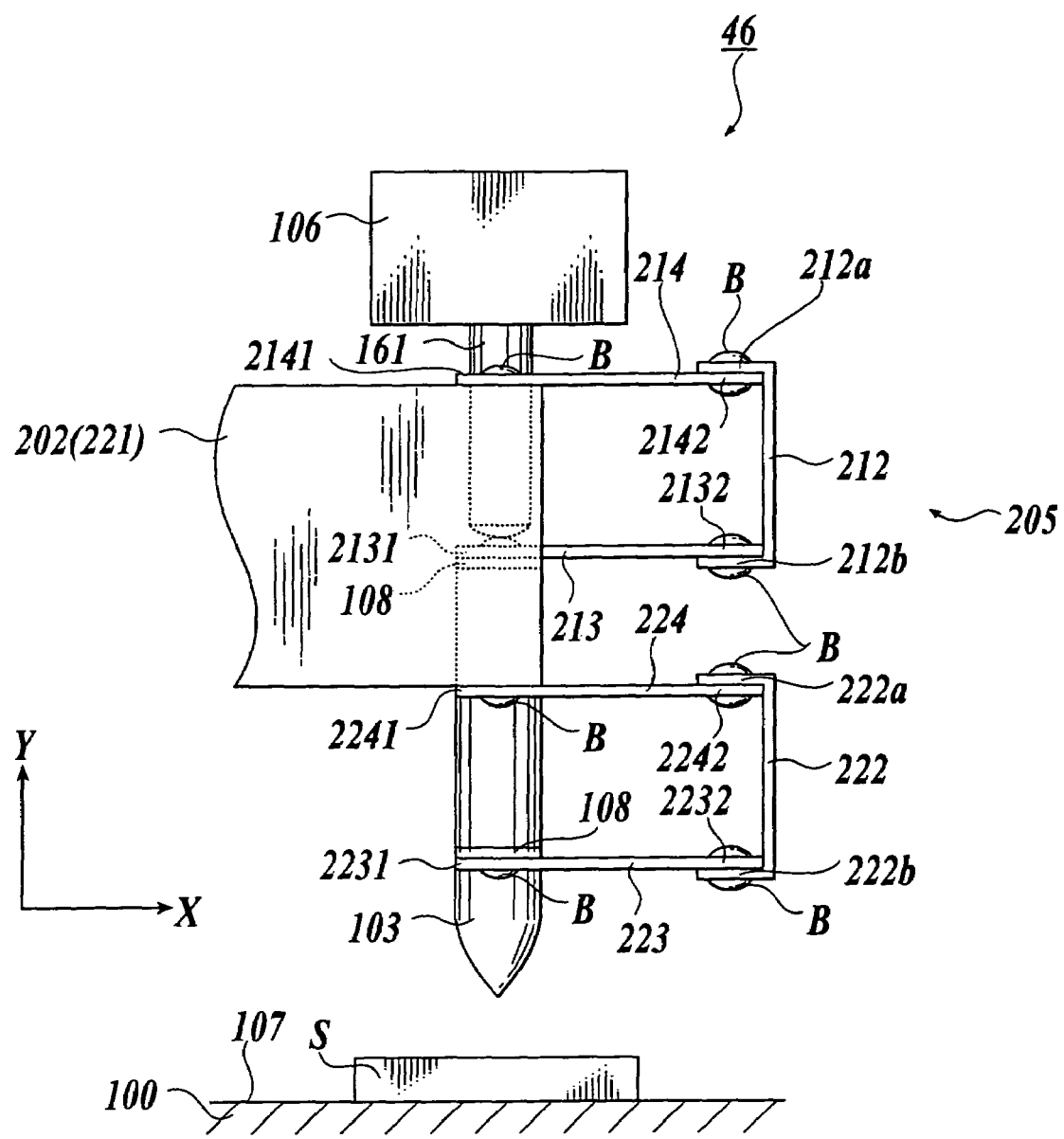
FIG. 11 is a side view showing a main part of a hardness testing apparatus according to the second modification of the fourth embodiment of the present invention.

FIG. 11 is a side view showing a main part of a hardness testing apparatus according to the second modification.

As shown in FIG. 11, a hardness testing apparatus 46 comprises a testing apparatus body 202 having an indenter shaft attaching member 221, the indenter shaft 104 changeably having the indenter 103 at the top (lower end) of the shaft 104, a supporting structure 205 elastically supporting the indenter shaft 104 to be movably in its axial direction and to be attached to the indenter shaft attaching member 221 of the testing apparatus body 202, the load applying mechanism 106 for applying a predetermined force to the indenter shaft 104 in its axial direction, and the sample stand 100 having the mounting surface 107 for mounting the sample S.

The supporting structure 205 comprises a plate spring 213 acting as a first elastic member, a plate spring 223 acting as the first elastic member, a plate spring 214 acting as a second elastic member, a plate spring 224 acting as the second elastic member, a connecting member 212 and a connecting member 222. An end 2131 of the plate spring 213 is fixed to the upper end of the indenter shaft 104 through one fixed plate 108 by bolts B. An end 2231 of the plate spring 223 is fixed to a portion between the lower end of the indenter shaft 104 and the indenter 103 through the other fixed plate 108 by bolts B. An end 2141 of the plate spring 214 is fixed to the upper surface of the indenter shaft attaching member 221 by bolt s B. An end 2241 of the plate spring 224 is fixed to the lower surface of the indenter shaft attaching member 221 by bolts B. The connecting member 212 connects another end 2132 of the spring 213 and another end 2142 of the plate spring 214. The connecting member 222 connects another end 2232 of the plate spring 223 and another end 2242 of the plate spring 224.

The plate springs 213, 214, 223 and 224 substantially have the same shape and spring constant as one another.

As shown in FIG. 11, each of the connecting members 212 and 222 is formed in an almost U shape in side view.

The other end 2142 of the plate spring 214 is fixed to an upper end 212a of the connecting member 212 by the bolts B, and the other end 2132 of the plate spring 213 is fixed to a lower end 212b of the connecting member 212 by the bolts B. The connecting member 212 connects the plate springs 213 and 214.

The other end 2242 of the plate spring 224 is fixed to an upper end 222a of the connecting member 222 by the bolts B, and the other end 2232 of the plate spring 223 is fixed to a lower end 222b of the connecting member 222 by the bolts B. The connecting member 222 connects the plate springs 223 and 224.

The indenter shaft 104 is attached to the testing apparatus body 202 (indenter shaft attaching member 221) through the supporting structure 205 so as to set the axial direction of the indenter shaft 104 perpendicular to the mounting surface 107 of the sample stand 100, and the indenter shaft 104 is elastically supported by the supporting structure 205. As shown in FIG. 11, the connecting members 212 and 222 are arranged to make the extending direction of the connecting members 212 and 222 be parallel to the axial direction (shaft axis) of the indenter shaft 104.

In the hardness testing apparatus 46, the load applying mechanism 106 applies a predetermined force (load) to the indenter shaft 104, and the indenter shaft 104 is moved downward. The plate springs 213 and 223, of which the ends 2131 and 2231 are fixed to the indenter shaft 104, are elastically deformed and warped due to the movement of the indenter shaft 104. The moment caused by the warp of the plate springs 213 and 223 is transmitted to the plate springs 214 and 224 through the connecting members 212 and 222, and the plate springs 214 and 224 are also elastically deformed. Because the plate springs 213, 214, 223 and 224 substantially have the same shape and spring constant as one another, in the same manner as the plate springs 153 and 154, the plate springs 213 and 214 are elastically deformed so as to make the deformed shapes of the plate springs 213 and 214 in side view be similar to and symmetric with each other, and the plate springs 223 and 224 are elastically deformed so as to make the deformed shapes of the plate springs 223 and 224 in side view be similar to and symmetric with each other. Amounts of displacement caused by the elastic deformation of the plate springs 213 and 214 in the X-axis direction are almost the same as each other, and directions of the displacement in the plate springs 213 and 214 are opposite to each other. Amounts of displacement caused by the elastic deformation of the plate springs 223 and 224 in the X-axis direction are almost the same as each other, and directions of the displacement in the plate springs 223 and 224 are opposite to each other. Therefore, the displacements of the plate springs 213 and 214 in the X-axis direction cancel each other out, and the displacements of the plate springs 223 and 224 in the X-axis direction cancel each other out. In this case, the movement of the indenter shaft 104 in the X-axis direction is prevented, and the indenter shaft 104 is moved in the Y-axis direction. That is, the apparatus 46 has the configuration that the indenter shaft 104 is not moved in the X-axis direction but is selectively moved in the Y-axis direction by relatively moving the supporting structure 205 (connecting members 212 and 222) to the side of the indenter shaft 104.

Therefore, in the hardness testing apparatus 46 having the supporting structure 205, the indenter 103 of the indenter shaft 104 can be pushed to the surface of the sample S in the axial direction of the indenter shaft 104. Accordingly, a dimple can be formed on the surface of the sample S by the indenter 103 with further accuracy, and the measuring test of the hardness of the sample S can be performed with further accuracy.

When the connecting members 212 and 222 in the second modification are integrally connected to each other, the supporting structure 205 becomes substantially the same as the supporting structure 105 of the hardness testing apparatus 44 of the fourth embodiment. That is, the hardness testing apparatus 46 becomes substantially the same as the hardness testing apparatus 44.

As described above, in the hardness testing apparatuses 44, 45 and 46, each of the supporting structures 105, 115 and 205 prevents the movement of the indenter shaft 104 perpendicular to its axial direction so as to selectively move the indenter shaft 104 in its axial direction. Therefore, the indenter 103 of the indenter shaft 104 can be pushed to the surface of the sample S in the direction of the indenter shaft 104. Accordingly, a dimple can be formed on the surface of the sample S by the indenter 103 with further accuracy, and the measuring test of the hardness of the sample S can be performed with further accuracy.

In the fourth embodiment, the force motor is used as the load applying mechanism 106. However, the hardness testing apparatus according to this invention is not limited to this. The load applying mechanism 106 may have a mechanism in which load based on dead weights or the rotation of an arm (lever) driven by a servomotor is applied.

Further, it is not required that the shape and spring constant of the first elastic member are substantially the same as those of the second elastic member. It is not required that the elastically-deformed shape of the first elastic member is the same as or similar to that of the second elastic member. The first and second elastic members may be structured on condition that the displacement and movement of the indenter shaft 104 in the X-axis direction due to the deformation of the first elastic member cancels out those in the second elastic member.

A guide member for guiding the movement of the indenter shaft 104 in its axial direction may be arranged to easily and selectively move the indenter shaft 104 in its axial direction. In this case, the shaft axis of the indenter shaft 104 is further hardly inclined.

Figure 25:
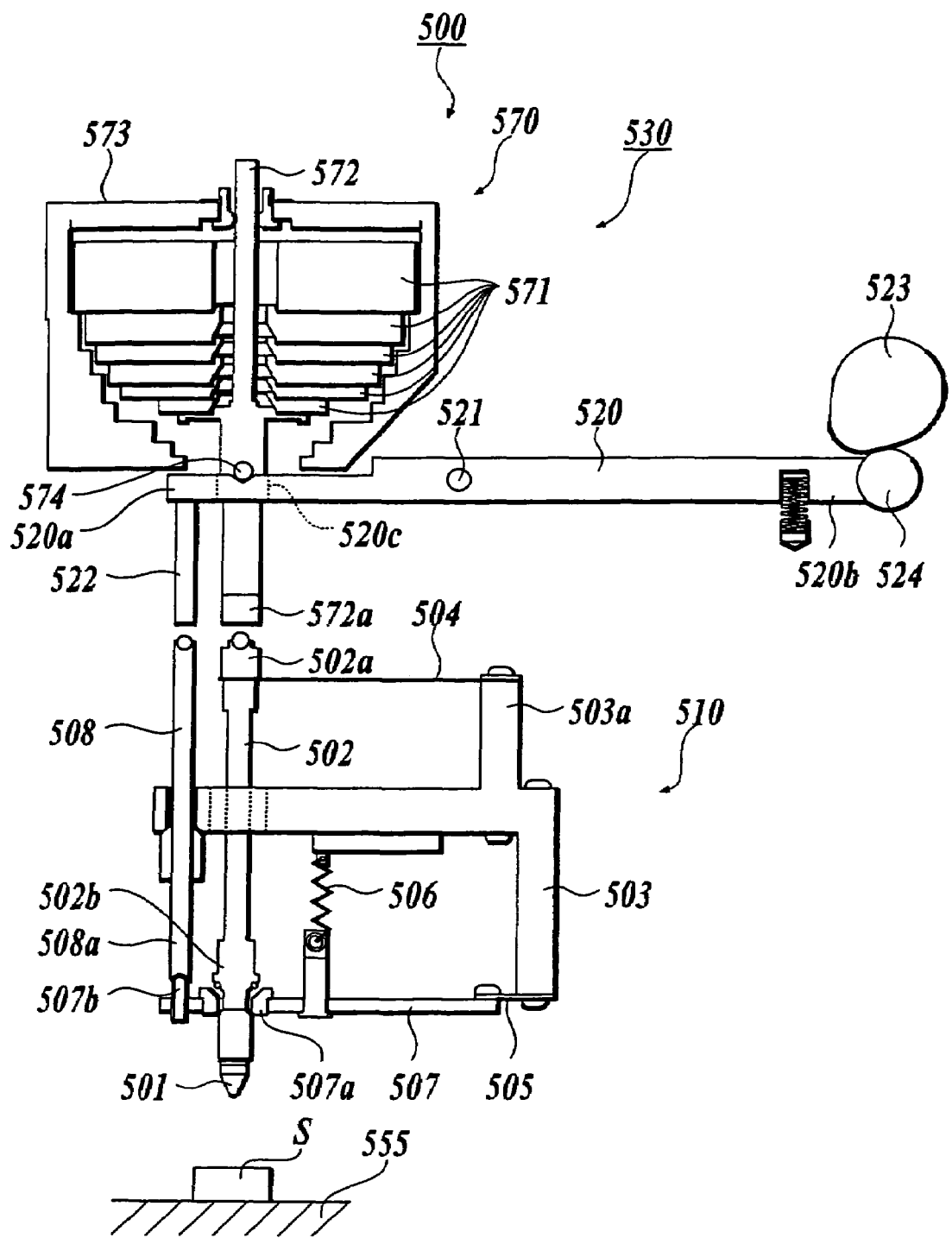
FIG. 25 is a side view schematically showing a main part of a hardness testing apparatus according to an earlier development.
Figure 26A:
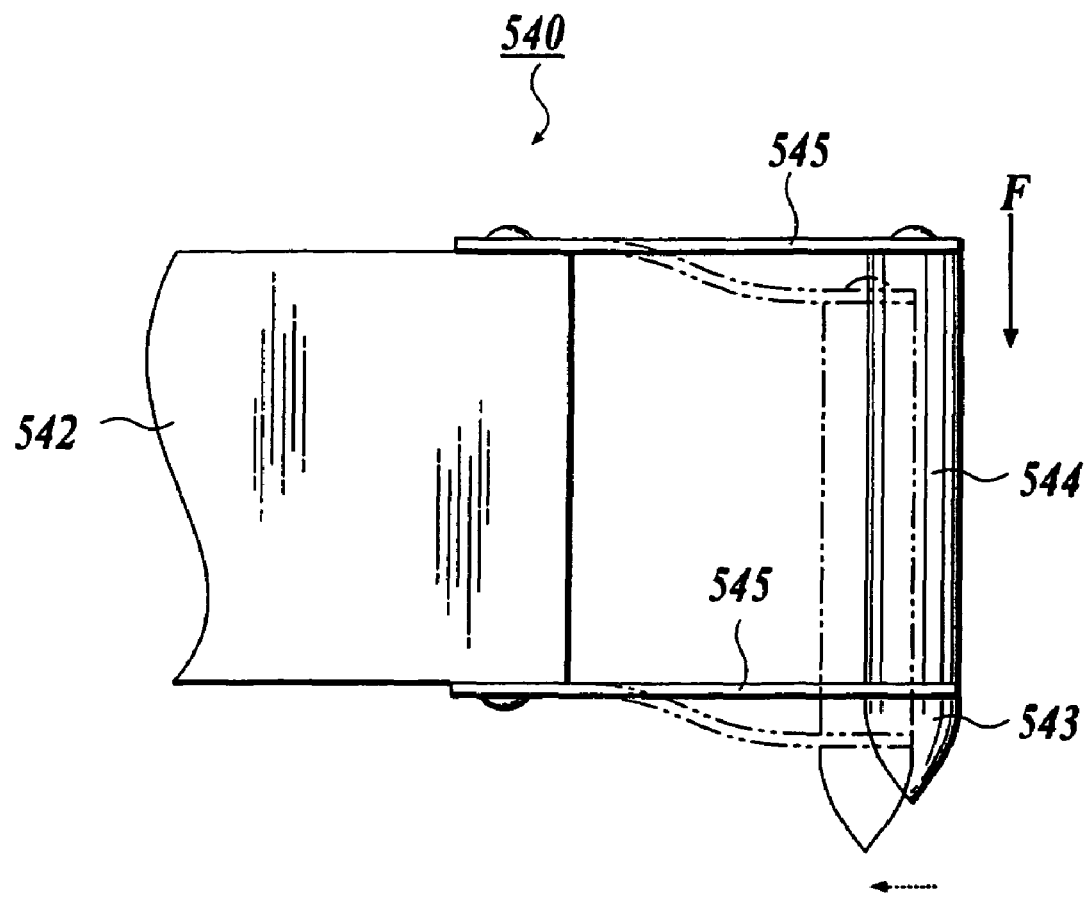
FIG. 26A is a side view schematically showing a main part of a hardness testing apparatus according to another earlier development.
Figure 26B:
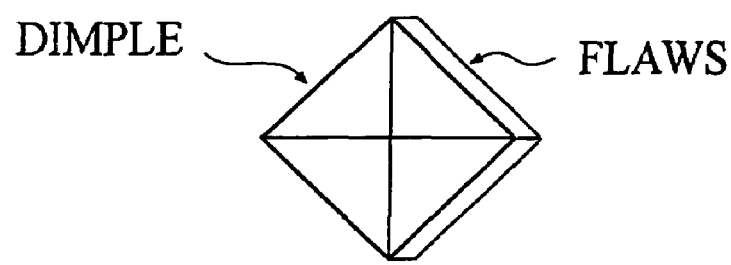
FIG. 26B is an explanatory view showing an example of a dimple.

Further, in the case of the use of the dimple forming mechanism of the earlier development shown in FIG. 25A in a small displacement region (condition for slightly moving and displacing the indenter shaft (indenter)), when the shaft axis of the indenter shaft is slightly displaced, the mechanism can be used. However, in the dimple forming mechanism according to the fourth embodiment, in addition to the use in the small displacement region, even though the warp of the plate springs and the stroke and displacement of the indenter shaft are large, the mechanism can be used and is especially effective.

Moreover, detailed structures of the hardness testing apparatus can be appropriately changed.

Fifth Embodiment

A hardness testing apparatus of the fifth embodiment will be described with reference to FIGS. 12 to 15.

Figure 12:
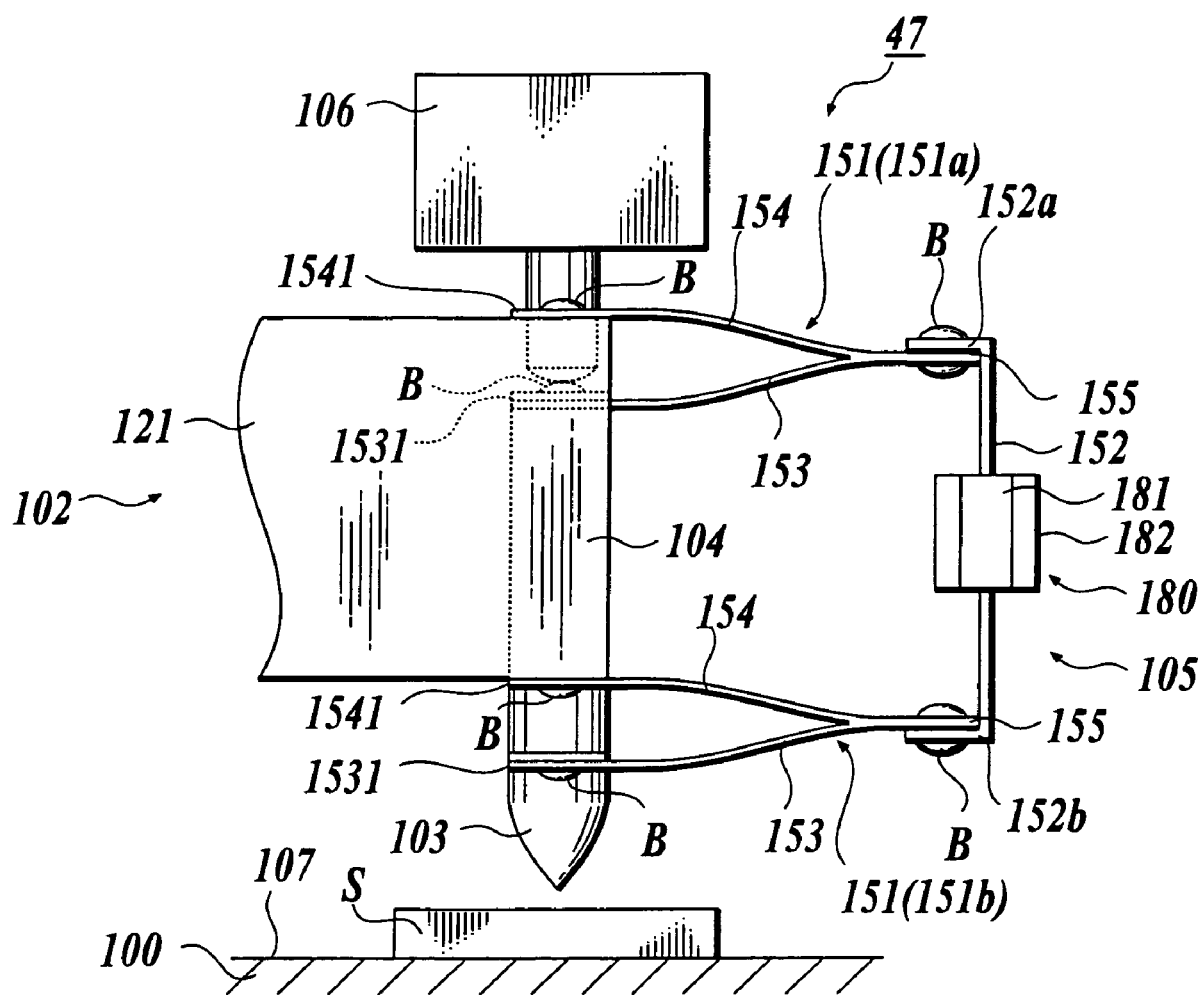
FIG. 12 is a side view showing a main part of a hardness testing apparatus according to the fifth embodiment of the present invention.
Figure 13:
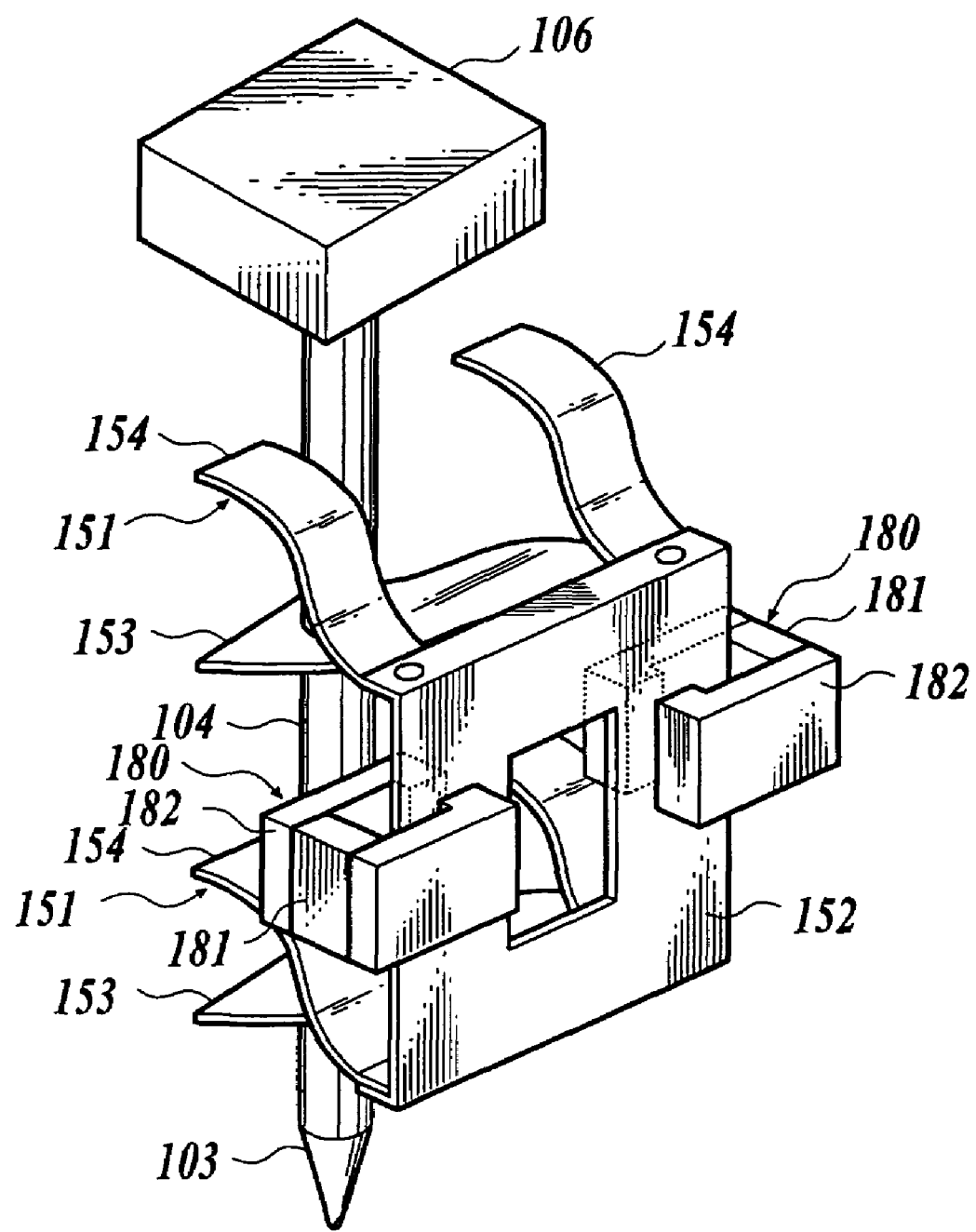
FIG. 13 is a perspective side view of the hardness testing apparatus shown in FIG. 12.
Figure 14:
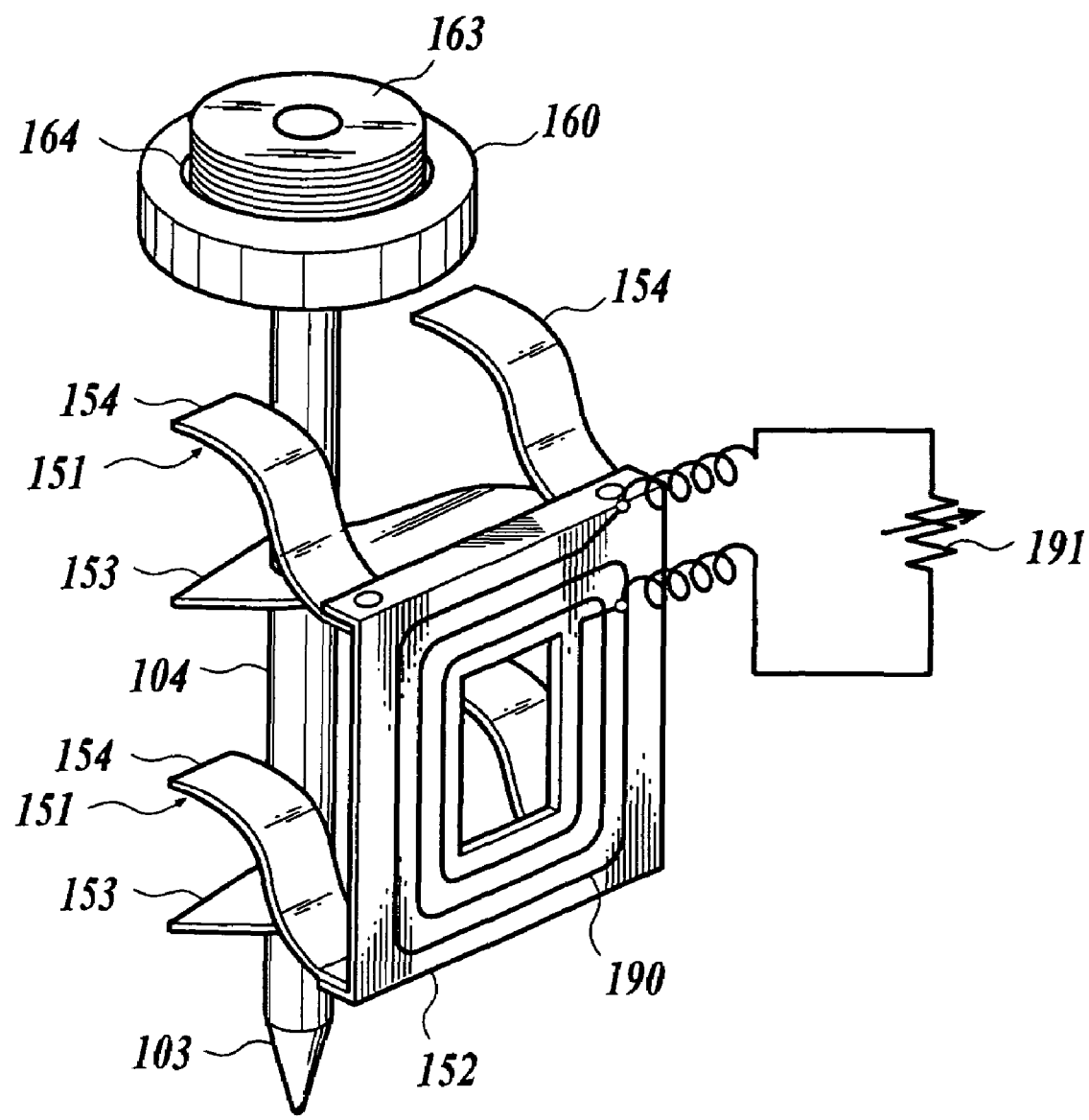
FIG. 14 is a perspective side view showing the inside of a load applying mechanism and the inside of a connecting member in the hardness testing apparatus shown in FIG. 12.
Figure 15:
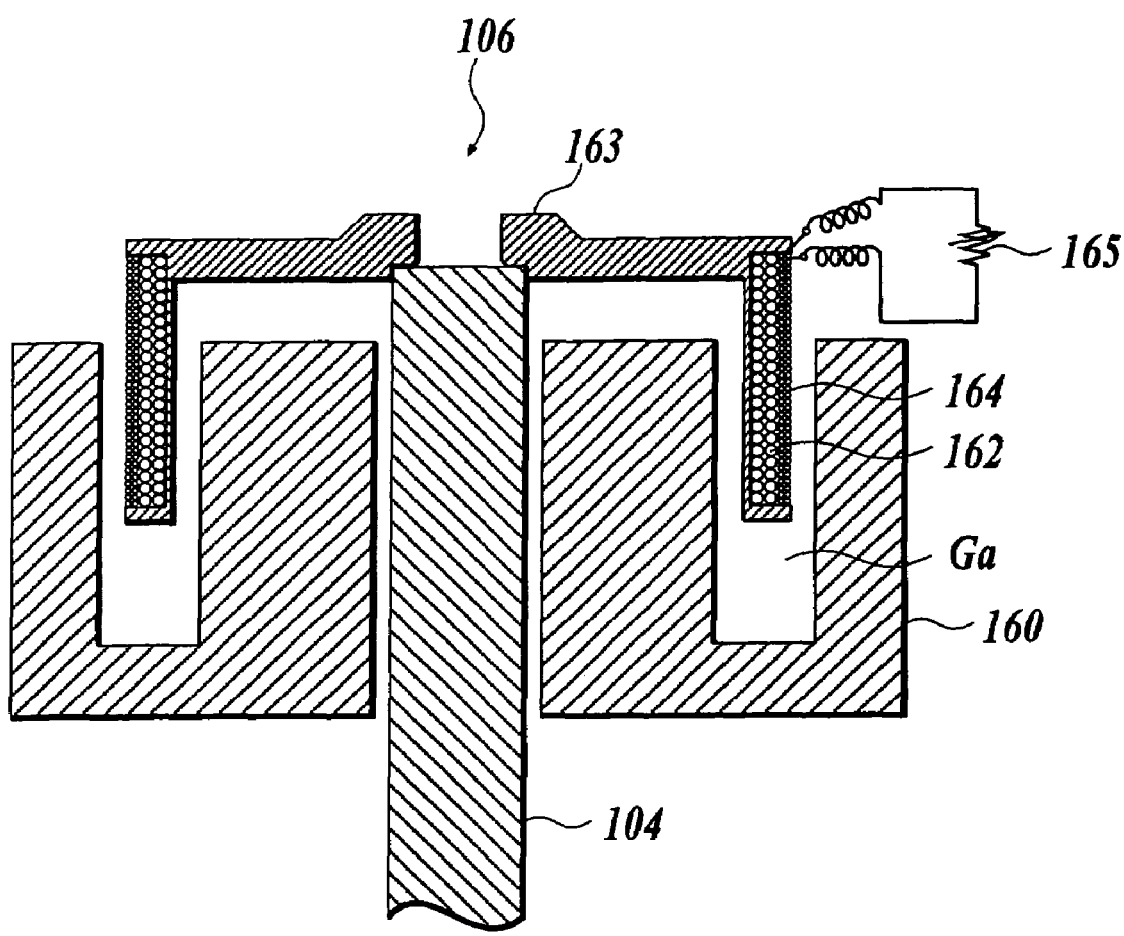
FIG. 15 is a sectional side view of the load applying mechanism according to the fifth embodiment of the present invention.

FIG. 12 is a side view showing a main part of a hardness testing apparatus 47 according to the fifth embodiment of the present invention. FIG. 13 is a perspective side view of the hardness testing apparatus 47 shown in FIG. 12. FIG. 14 is a perspective side view showing the inside of a load applying mechanism and the inside of a connecting member in the hardness testing apparatus 47 shown in FIG. 12. FIG. 15 is a sectional side view of the load applying mechanism.

As shown in FIGS. 12 and 13, the hardness testing apparatus 47 differs from the hardness testing apparatus 44 of FIG. 7 in that the hardness testing apparatus 47 further comprises two connecting member magnetic field inducing members 180 arranged to be opposite to each other through the connecting member 152. Each connecting member magnetic field inducing member 180 comprises a permanent magnet 181 and a pair of yokes 182 arranged on both sides of the permanent magnet 181 and formed integrally with the permanent magnet 181. The connecting member magnetic field inducing member 180 is formed in an almost U shape in plan view.

An open-side end of each yoke 182 of the connecting member magnetic field inducing member 180 is bent toward the side of the connecting member 152 and is arranged to be apart from the connecting member 152. The permanent magnet 181 is placed between the other ends of the yokes 182 and is supported and fixed by the yokes 182. Therefore, a magnetic field is induced by magnetic fluxes of the permanent magnet 181 concentrated and maximized in a predetermined direction by the yokes 182. That is, a portion of the connecting member 152 is arranged in the magnetic field.

Because the connecting member 152 is made of the non-magnetic conductor, no magnetic path is formed between the connecting member magnetic field inducing member 180 and the connecting member 152.

As shown in FIG. 14, the connecting member 152 comprises a connecting member damping coil 190 wound inside the member 152, and a connecting member variable resistor 191 electrically connected to the connecting member damping coil 190. The connecting member damping coil 190 is arranged in the magnetic field induced by the connecting member magnetic field inducing member 180. Therefore, when the connecting member 152 is vibrated with the vibration of the indenter shaft 104 at its characteristic frequency in the hardness test, an electromotive force is generated in the connecting member damping coil 190 arranged in the magnetic field in proportional to the speed of the vibration. Therefore, current flows through the connecting member damping coil 190, and an attenuation force acts on the connecting member 152 so as to attenuate the vibration of the connecting member 152.

Further, the strength of the attenuation force can be adjusted by making the connecting member variable resistor 191 change a resistive value of the connecting member damping coil 190.

As described above, the connecting member damping coil 190 and the connecting member variable resistor 191 function as a connecting member attenuator.

As shown in FIG. 15, the load applying mechanism 106 comprises a magnetic field inducing member 160 for inducing a magnetic field, a driving coil 162 arranged in the magnetic field induced by the magnetic field inducing member 160, a power supply (not shown) for supplying driving current to the driving coil 162, and a coil bobbin 163 having the driving coil 162 wound thereon and arranged movably in the upper and lower directions.

The magnetic field inducing member 160 is, for example, made of a permanent magnet. As shown in FIGS. 14 and 15, the indenter shaft 104 penetrates through the center of the magnetic field inducing member 160 to be movable in the axial direction of the indenter shaft 104. A groove Ga for receiving the driving coil 162 is formed on the upper surface of the magnetic field inducing member 160.

The coil bobbin 163 has a bobbin of a predetermined width, and the driving coil 162 is wounded on the bobbin. The coil bobbin 163 is tightly fitted to the upper end of the indenter shaft 104 and is arranged to place a portion of the driving coil 162 in the groove Ga of the magnetic field inducing member 160. Therefore, when the driving current is supplied to the driving coil 162 arranged in the magnetic field, a driving force is generated. The coil bobbin 163 having the driving coil 162 wound thereon is moved downward by the driving force to press down the indenter shaft 104, and the coil bobbin 163 moves the indenter shaft 104 in its axial direction to apply a predetermined test force to the sample S through the indenter shaft 104. Therefore, the coil bobbin 163 functions as a pressing member for pressing the indenter shaft 104.

Further, the coil bobbin 163 is made of a conductive material, and the portion of the coil bobbin 163 having the driving coil 162 wound thereon is placed in the magnetic field. Therefore, simultaneously with the generation of the driving force in the driving coil 162 of the coil bobbin 163, the attenuation force directed reversely to the moving direction of the coil bobbin 163 is generated in proportional to a moving speed of the coil bobbin 163. That is, for example, when the indenter shaft 104 is vibrated with vibration of disturbance, the coil bobbin 163 fixed to the indenter shaft 104 is also vibrated, and an electromotive force proportional to the speed of the vibration is generated in the coil bobbin 163 made of conductor. Therefore, current flows through the coil bobbin 163, the attenuation force is generated, and the vibration of the indenter shaft 104 is attenuated by the attenuation force.

Moreover, a damping coil 164 is wound on the coil bobbin 163 on the outside of the driving coil 162 to attenuate the vibration of the indenter shaft 104. A variable resistor 165 is electrically connected to the damping coil 164 to obtain a dumping coil 164 having a changeable resistive value. That is, for example, when the indenter shaft 104 is vibrated due to vibration of disturbance, an electromotive force proportional to the speed of the vibration of the indenter shaft 104 is generated in the damping coil 164, current flows through the damping coil 164, and the attenuation force for attenuating the vibration of the indenter shaft 104 is generated.

Further, the strength of the attenuation force is changeable by making the variable resistor 165 change the resistive value of the damping coil 164.

As described above, the coil bobbin 163, the damping coil 164 and the variable resistor 165 function as the attenuator for attenuating the vibration of the indenter shaft 104.

Next, an operation of the hardness testing apparatus 47 in the hardness test will be described.

The sample S is initially mounted on the mounting surface 107 of the sample stand 100, and an operational section (not shown) is operated to perform the hardness test of the hardness testing apparatus 47. Thereafter, a control section (not shown) supplies a predetermined amount of current to the driving coil 162 of the load applying mechanism 106 according to the input to the operational section, and the driving force is generated. When the driving force is generated in the driving coil 162, the coil bobbin 163 having the driving coil 162 wound thereon is moved downward to press down the indenter shaft 104, and the indenter shaft 104 is moved in its axial direction.

Due to the movement of the indenter shaft 104, the middle plate springs 153 having the ends 1531 fixed to the indenter shaft 104 are elastically deformed and warped, and the outer plate springs 154 are elastically deformed and warped. The spring motion caused by the warp of the outer plate springs 154 cancels out the spring motion caused by the warp of the middle plate springs 153. Therefore, the displacement of the shaft axis of the indenter shaft 104 in the direction perpendicular to its axial direction is prevented, and the indenter shaft 104 is moved in its axial direction. Thereafter, the indenter shaft 104 is moved downward while deforming the folding springs 151 and pushes the indenter 103 to the surface of the sample S at the predetermined force (load), and a dimple is formed.

Thereafter, a measuring test of a hardness of the sample S, for example, a low hardness test is performed according to the dimple formed by the indenter 103 (indenter shaft 104) in the sample S.

In the hardness test, when the moving speed of the indenter shaft 104 is, for example, heightened, the indenter shaft 104 is vibrated at its characteristic frequency due to the driving force acting on the indenter shaft 104. At this time, the attenuation force is generated in both the coil bobbin 163 of the load applying mechanism 106 and the damping coil 164 wound on the coil bobbin 163, and the vibration of the indenter shaft 104 is attenuated by the attenuation force.

Simultaneously with the attenuation of the vibration of the indenter shaft 104, an attenuation force proportional to the vibration is generated in the connecting member damping coil 190 arranged in the connecting member 152, and the vibration of the connecting member 152 due to the vibration of the indenter shaft 104 is attenuated.

When the indenter shaft 104 is vibrated at its characteristic frequency due to vibration of disturbance in the hardness test, an attenuation force is generated in the same manner, and the vibration of the indenter shaft 104 and the vibration of the connecting member 152 are attenuated.

To adjust the attenuation force, the resistive value of the damping coil 164 or the connecting member damping coil 190 is changed by the variable resistor 165 or the connecting member variable resistor 191.

As described above, in the hardness testing apparatus 47 of the fifth embodiment, when the indenter shaft 104 is vibrated due to vibration of disturbance, the electromotive force is generated in the damping coil 164 arranged in the magnetic field of the magnetic field inducing member 160, the current flows to generate the attenuation force, and the vibration of the indenter shaft 104 can be attenuated by the attenuation force.

Further, because the resistive value of the damping coil 164 can be changed by the variable resistor 165 connected to the damping coil 164, the attenuation force for attenuating the vibration of the indenter shaft 104 can be adjusted.

Further, the electromotive force is generated in the coil bobbin 163 made of a conductive material and having the driving coil 162 thereon, and the current flows to generate the attenuation force. Accordingly, the vibration of the indenter shaft 104 can be further attenuated.

Further, because the spring ends 155 of the folding springs 151 adjacent to each other are connected to each other by the connecting member 152, independent motion of the folding springs 151 can be prevented, and a further degree of straightness of material of the indenter shaft 104 in its axial direction can be achieved.

Further, because the electromotive force is generated in the connecting member damping coil 190 arranged in the magnetic field of the connecting member magnetic field inducing member 180, the current flows to generate the attenuation force. Accordingly, the vibration of the connecting member 152 caused by the vibration of the indenter shaft 104 can be attenuated.

Further, because the resistive value of the connecting member damping coil 190 can be changed by the connecting member variable resistor 191 connected to the connecting member damping coil 190, the attenuation force for attenuating the vibration of the connecting member 152 caused by the vibration of the indenter shaft 104 can be adjusted.

Further, because the portion of the connecting member 152 made of a non-magnetic conductive material is arranged in the magnetic field induced by the connecting member magnetic field inducing member 180, the electromotive force is generated in the connecting member 152, and the current flows to generate the attenuation force. Accordingly, the vibration of the connecting member 152 caused by the vibration of the indenter shaft 104 can be attenuated.

The hardness testing apparatus of the present invention is not limited to the fifth embodiment. For example, vibration of an indenter shaft may be attenuated by using an attenuator (for example, damping coil or coil bobbin) arranged in a load applying mechanism without arranging any connecting member attenuating member in a connecting member. Alternatively, vibration of an indenter shaft may be attenuated by using a connecting member attenuating member (for example, a connecting member damping coil or the like) arranged in a connecting member without arranging any attenuator in a load applying mechanism.

Further, the load applying mechanism may have a driving coil and a damping coil wound as an attenuator on the outside of the driving coil without using any coil bobbin as the attenuator.

Further, only a coil bobbin may be used as the attenuator of the load applying mechanism without using any damping coil.

Further, only a connecting member damping coil may be used as a connecting member attenuator to use a connecting member made of a non-conducting material. Alternatively, no connecting member damping coil may be used as a connecting member attenuator to use a connecting member made of a non-magnetic conductive material.

Further, a magnetic field inducing member arranged in the load applying mechanism may be made of an electromagnetic coil. In this case, current is supplied to the electromagnetic coil, and a magnetic field is induced.

The hardness testing apparatus of the present invention is applicable to Vickers hardness test and large stroke pushing-in test.

Sixth Embodiment

Figure 16:
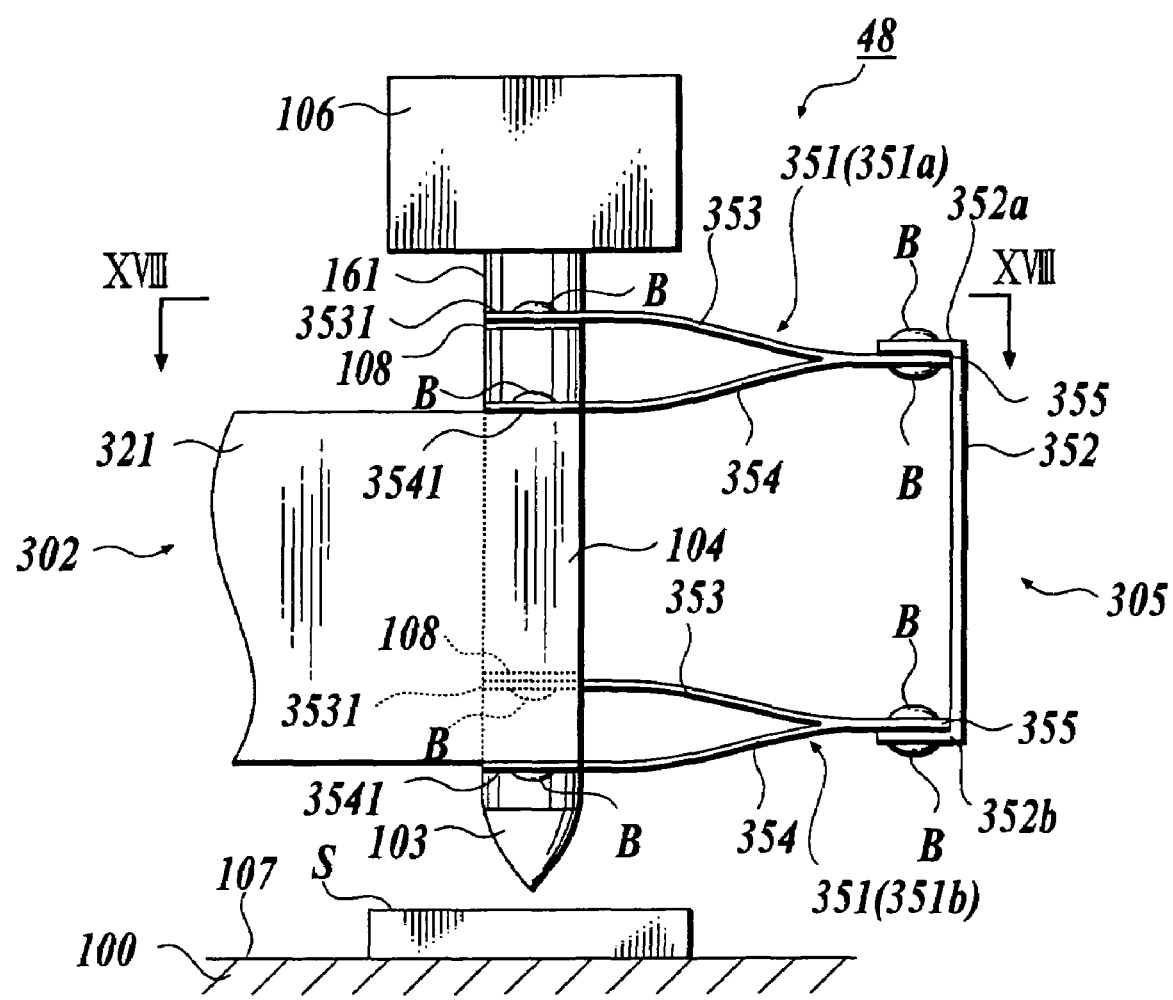
FIG. 16 is a side view showing a main part of a hardness testing apparatus according to the sixth embodiment of the present invention.
Figure 17:
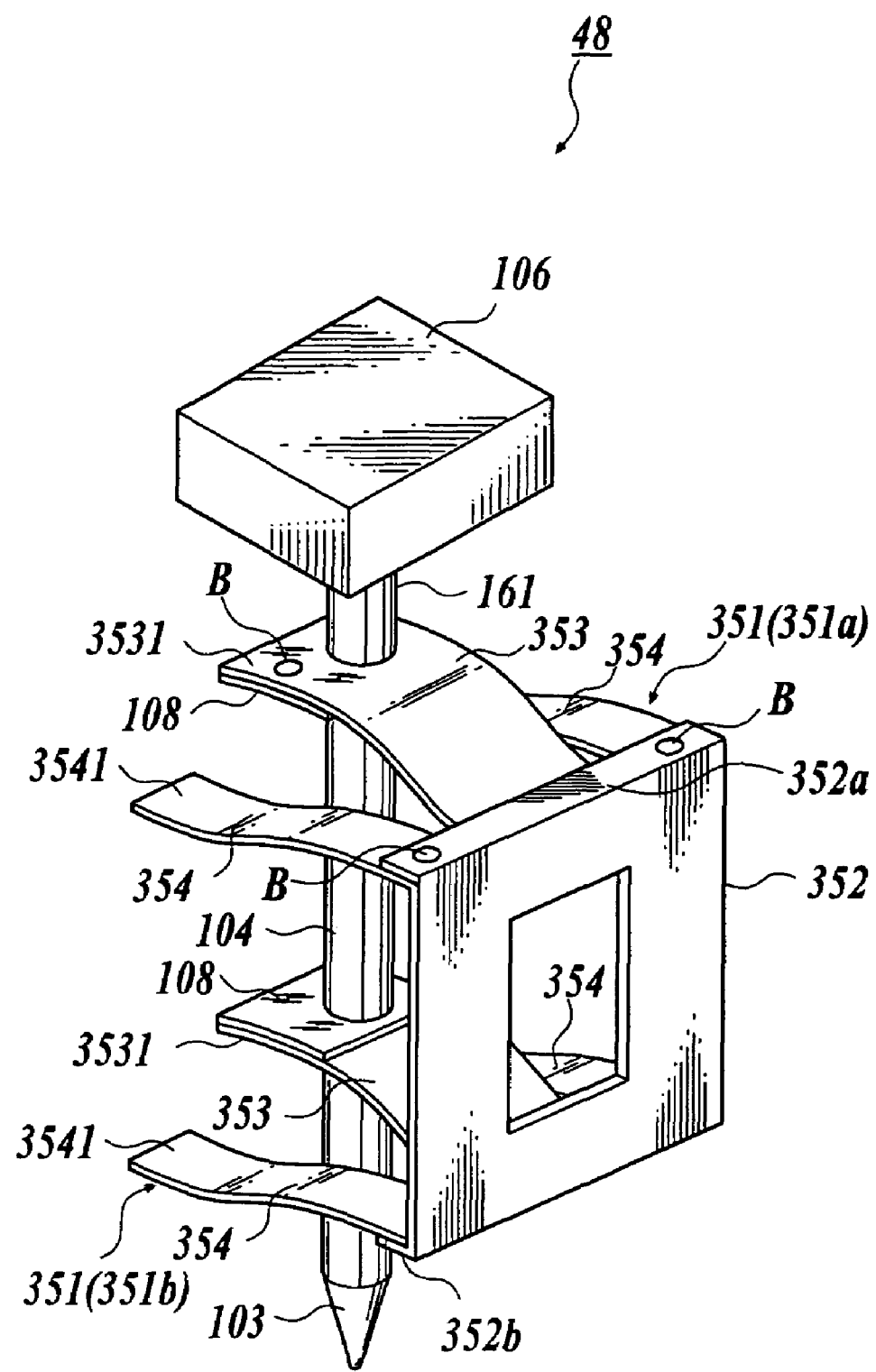
FIG. 17 is a perspective side view of the hardness testing apparatus shown in FIG. 16.
Figure 18:
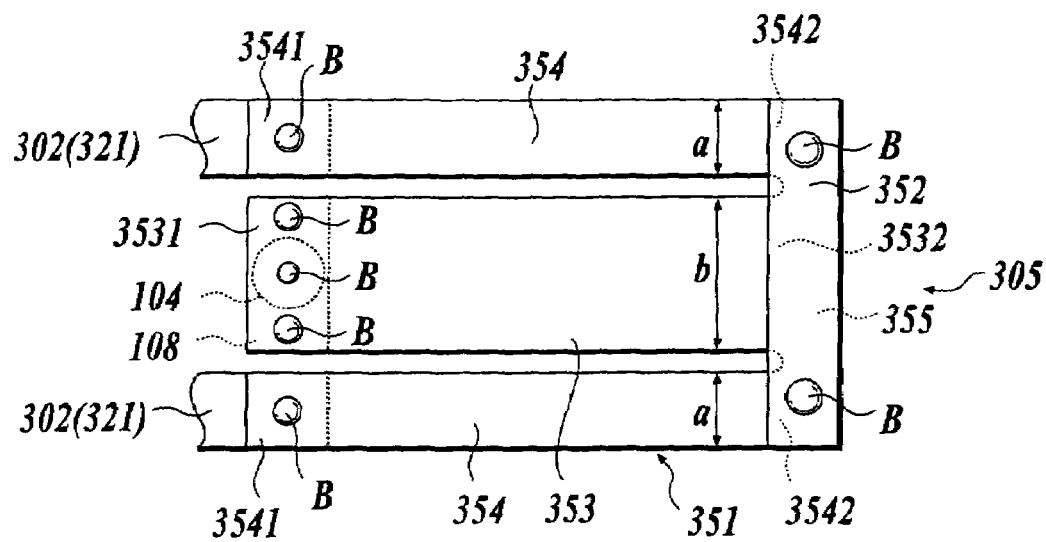
FIG. 18 is a plan view seen from line XVIII-XVIII of FIG. 16.
Figure 19:
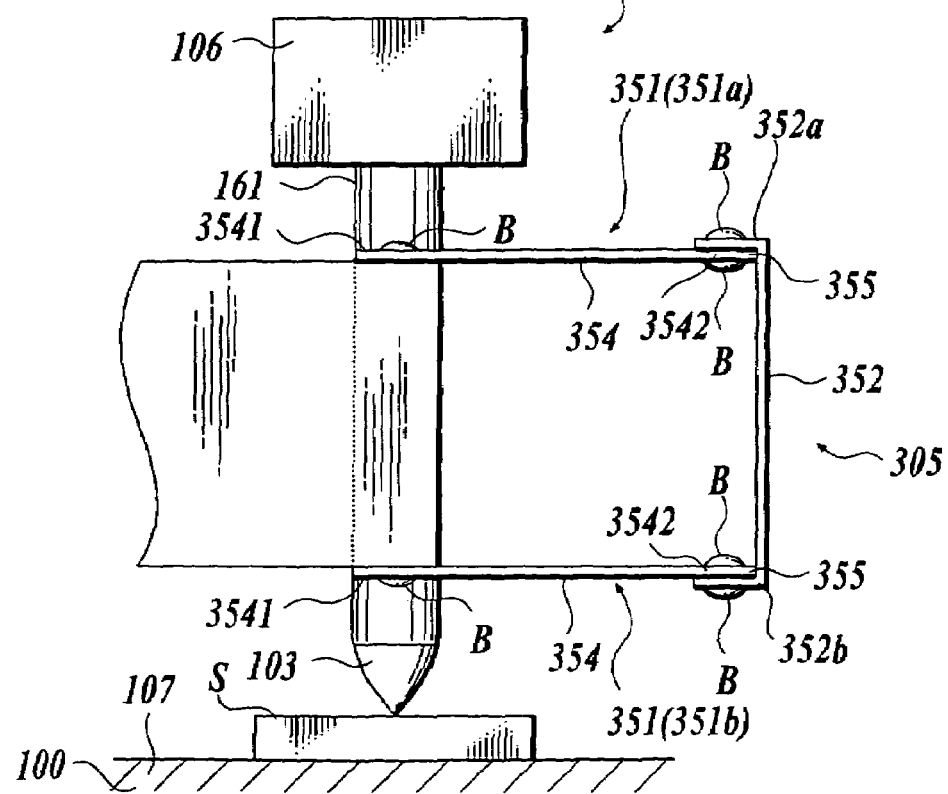
FIG. 19 is a side view of a main part of the hardness testing apparatus in the hardness test according to the sixth embodiment of the present invention.
Figure 20:
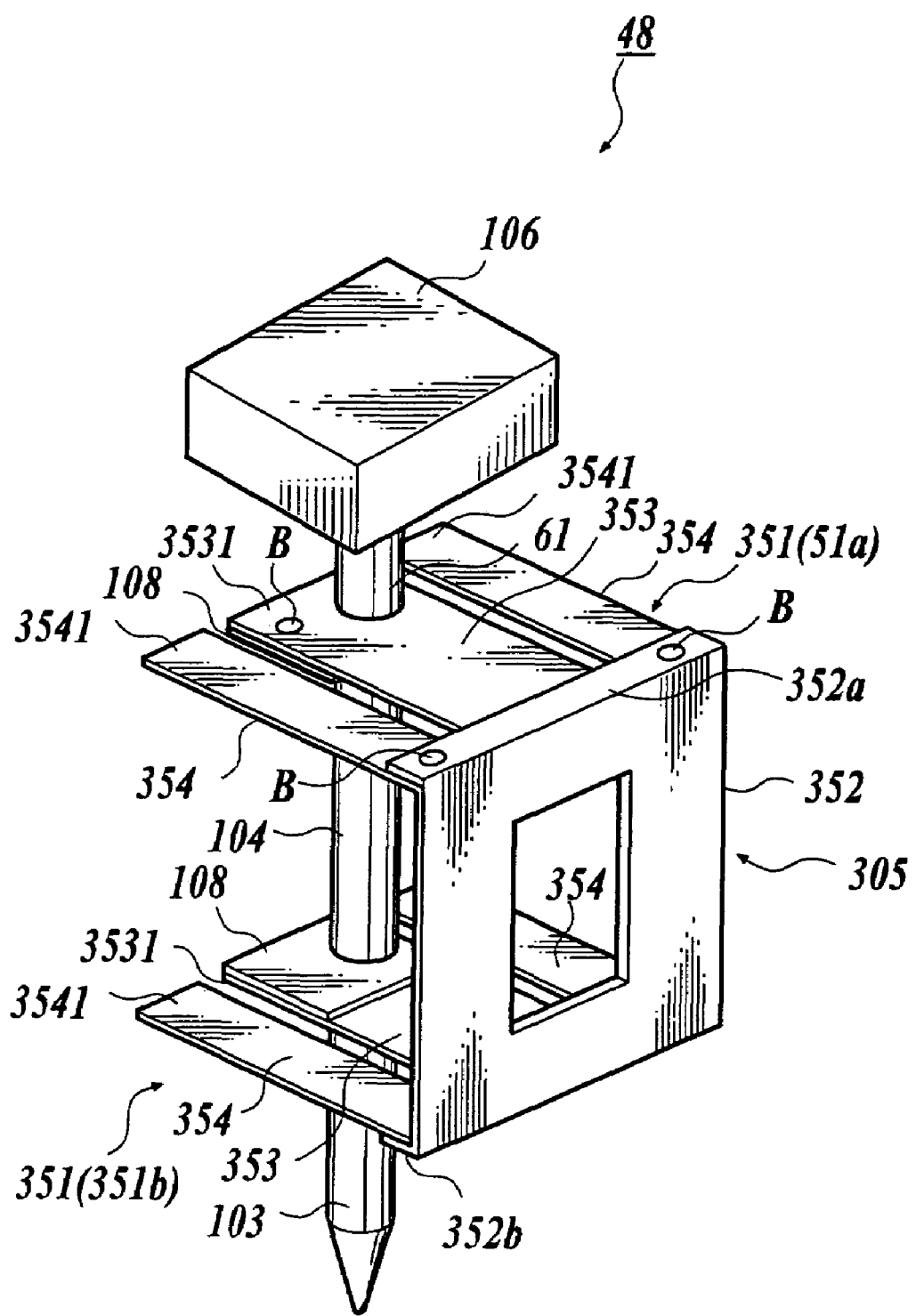
FIG. 20 is a perspective side view of a main part of the hardness testing apparatus shown in FIG. 19.

A hardness testing apparatus 48 of the sixth embodiment will be described with reference to FIGS. 16 to 20. FIG. 16 is a side view showing a main part of a hardness testing apparatus 48 according to the sixth embodiment of the present invention. FIG. 17 is a perspective side view of the hardness testing apparatus 48 of FIG. 16. FIG. 18 is a plan view seen from line XVIII-XVIII of FIG. 16. FIG. 19 is a side view of the main part of the hardness testing apparatus 48 in the hardness test. FIG. 20 is a perspective side view of the main part of the hardness testing apparatus 48 of FIG. 19.

As shown in FIG. 16, the hardness testing apparatus 48 comprises a testing apparatus body 302 having an indenter shaft attaching member 321, the indenter shaft 104 having the indenter 103 at the top (lower end) thereof, a supporting structure 305 elastically supporting the indenter shaft 104 to be movable in its axial direction and to be attached to the indenter shaft attaching member 321 of the testing apparatus body 302, the load applying mechanism 106, and the sample stand 100.

The supporting structure 305 comprises two folding springs 351 (351a, 351b) for connecting the indenter shaft attaching member 321 to the indenter shaft 104 at upper and lower ends of the indenter shaft 104 respectively, and a connecting member 352 connecting the upper and lower folding springs 351 to each other.

As shown in FIG. 18, each folding spring 351 comprises a middle plate spring 353 extending to the left of the drawing to have an end 3531 on the left and acting as a first elastic member, and two outer plate springs 354 arranged on both sides of the middle plate spring 353 (upper and lower sides of the middle plate spring 353 in the drawing), extending to the left of the drawing to have an end 3541 on the left and acting as a second elastic member. Another end 3532 of the middle plate spring 153 is integrally connected to other ends 3542 of the outer plate springs 354 on the right of the drawing at a spring end 355 acting as a connecting portion.

In the same manner as in the folding springs 151 shown in FIG. 8, the folding springs 351 are structured. That is, length and thickness of the middle plate spring 353 are almost the same as those of each outer plate spring 354, and the width of the middle plate spring 353 is substantially the same as that of the combination of the outer plate springs 354. Therefore, a spring constant of the middle plate spring 353 is almost the same as that of the combination of the outer plate springs 354.

Each folding spring 351 is, for example, made of beryllium copper and is shaped by age hardening in a shape that the spring 351 is in advance warped in a V shape in side view. That is, each middle plate spring 353 is warped so as to be projected upward and to have the end 3531 at an upper position, and each outer plate spring 354 is warped so as to be projected downward and to have the end 3541 at a lower position.

The folding springs 351 shaped as described above have non-linear elastic characteristic. That is, the smaller the displacement of the plate springs 353 and 354 is, the larger the spring constant of the plate springs 353 and 354 is. The larger the displacement of the plate springs 353 and 354 is, the smaller the spring constant of the plate springs 353 and 354 is.

The small displacement of the plate springs 353 and 354 indicates the condition that the folding springs 351 elastically support the indenter shaft 104 before the hardness test. The large displacement of the plate springs 353 and 354 indicates the condition of the hardness test that the indenter shaft 104 is moved toward the sample S and the warped plate springs 353 and 354 of the folding springs 351 extend almost straight.

As shown in FIG. 16, the middle plate springs 353 of the folding springs 351 are inclined so as to place those ends 3531 to upper left of the plate springs 353 in the drawing, and the outer plate springs 354 of the folding springs 351 are inclined so as to place those ends 3451 to lower left of the plate springs 354 in the drawing.

In the upper folding spring 351a, the ends 3531 of the middle plate springs 353 are fixed to the upper end of the indenter shaft 104 through the fixing plate 108 by bolts B, and the ends 3541 of the outer plate springs 354 are fixed to the upper surface of the indenter shaft attaching member 321 by bolts B.

In the lower folding spring 351b, the ends 3531 of the middle plate springs 353 are fixed to a portion between the lower end of the indenter shaft 104 and the indenter 103 through the fixing plate 108 by bolts B, and the ends 3541 of the outer plate springs 354 are fixed to the lower surface of the indenter shaft attaching member 321 by bolts B.

The folding springs 351 adjacent to each other are connected to each other by a connecting member 352.

As shown in FIG. 16, the connecting member 352 is formed in a U shape in side view. The spring end 355 of the upper folding spring 151a is fixed to an upper end 352a of the connecting member 352 by bolts B, and the spring end 355 of the lower folding spring 351b is fixed to a lower end 352b of the connecting member 352 by bolts B. The connecting member 352 connects the upper folding spring 351a and the lower folding spring 351b.

In each folding spring 351, the end 3532 of the middle plate spring 353 and the ends 3542 of the outer plate springs 354 are connected to each other to have a supporting point by fixing the spring end 355 of the folding spring 351 to the upper or lower end 352a or 352b of the connecting member 352.

The indenter shaft 104 is attached to the testing apparatus body 302 by the folding springs 351 so as to make the axial direction of the indenter shaft 104 be perpendicular to the mounting surface 107 of the sample stand 100, and the indenter shaft 104 is elastically supported by the folding springs 351.

Further, as shown in FIGS. 19 and 20, as the indenter shaft 104 is moved in its axial direction by applying the test force to the indenter shaft 104, the warped spring shapes of the middle plate springs 353 and the outer plate springs 354 of the folding springs 351 approach straight spring shapes. When the indenter 103 reaches the surface of the sample S, the middle plate springs 353 and the outer plate springs 354 extend in almost straight shape in the direction perpendicular to the axial direction of the indenter shaft 104. That is, the upper and lower folding springs 351 are elastically deformed in plane shape, and the plane surface of each folding spring 351 is placed in a plane extending in the direction perpendicular to the axial direction of the indenter shaft 104.

The indenter shaft 104 is attached to the testing apparatus body 302 (indenter shaft attaching member 321) by the folding springs 351 so as to make the axial direction of the indenter shaft 104 be perpendicular to the mounting surface 107 of the sample stand 100, and the indenter shaft 104 is elastically supported.

As shown in FIG. 16, the connecting member 352 is arranged so as to make the extending direction of the connecting member 352 be parallel to the axial direction of the indenter shaft 104.

Next, an example of an operation of the hardness testing apparatus 48 in the hardness test will be described in detail.

The sample S is initially mounted on the mounting surface 107 of the sample stand 100, and an operational section (not shown) is operated to perform the hardness test of the hardness testing apparatus 48. Thereafter, a control section (not shown) supplies a predetermined amount of current to a driving coil of the load applying mechanism 106 according to the input to the operational section, and a driving force is generated. Thereafter, when the driving force is generated in the driving coil, the load shaft 161 presses the indenter shaft 104 in its axial direction by the driving force, and the indenter shaft 104 is moved.

When the load applying mechanism 106 applies the test force to the indenter shaft 104, the indenter shaft 104 is moved toward the sample S. At this time, the spring motion caused by the displacement of the outer plate springs 354 of the folding springs 351 cancels out the spring motion caused by the displacement of the middle plate springs 353, and the displacement of the indenter shaft 104 in the direction perpendicular to its axial direction is prevented, and the indenter shaft 104 is moved in its axial direction.

The middle plate springs 353 having the ends 3531 fixed to the indenter shaft 104 are elastically deformed while the indenter shaft 104 is moved toward the sample S, and the warped spring shape of each middle plate spring 353 approaches the straight spring shape. In the same manner, the outer plate springs 354 are elastically deformed, and the warped spring shape of each outer plate spring 354 approaches the straight spring shape. Thereafter, when the indenter 103 arrives at the surface of the sample S, as shown in FIG. 19, the middle plate springs 353 and the outer plate springs 354 of the folding springs 351 extend in almost straight shape in the direction perpendicular to the axial direction of the indenter shaft 104. That is, as shown in FIG. 20, the upper and lower folding springs 351 are made plane by the extension of the middle plate springs 353 and the outer plate springs 354 of the folding springs 351, and the plane surface of each folding spring 351 is placed in a plane extending in the direction perpendicular to the axial direction of the indenter shaft 104.

Thereafter, the indenter shaft 104 is moved downward while elastically deforming the folding springs 351, and the indenter shaft 104 makes the indenter 103 push to the surface of the sample S at a predetermined force to form a dimple. Thereafter, a hardness measuring test of the sample S, for example, a low hardness test is performed according to the dimple formed by the indenter 103 in the sample S.

As described above, in the hardness testing apparatus 48, as the indenter shaft 104 is moved toward the sample S, the warped spring shape of each middle plate spring 353 in the supporting structure 305 approaches the straight spring shape, and the warped spring shape of each outer plate spring 354 approaches the straight spring shape. When the indenter 103 arrives at the surface of the sample S, the middle plate springs 353 and the outer plate springs 354 extend in almost straight shape in the direction perpendicular to the axial direction of the indenter shaft 104. Therefore, even though vibration of disturbance occurs in the connecting member 352 of the upper and lower folding springs 351 during the formation of the dimple on the surface of the sample S by the indenter 103, the indenter shaft 104 is not displaced in the direction perpendicular to its axial direction. Accordingly, no deformation is generated in the dimple formed by the indenter 103, and error in the calculated hardness can be reduced without any complicated mechanism.

Further, the middle plate springs 353 and the outer plate springs 354 of the folding springs 351 have the non-linear elastic characteristic. That is, the smaller the displacement of the springs is, the larger the spring constant is. The larger the displacement of the springs is, the smaller the spring constant is. Therefore, when the displacement of the folding springs 351 is large, that is, when the warped spring shape of each folding spring 351 is changed to the straight spring shape by the movement of the indenter shaft 104 toward the sample S caused by the applying of the test force to the indenter shaft 104, because the spring constant becomes small, the stiffness of the folding springs 351 in the axial direction of the indenter shaft 104 can be lowered. Accordingly, in correction in the calculation of a substantial test force, because the amount of correction can be reduced, error in the calculated hardness can be reduced.

Moreover, because the folding springs 351 have the non-linear elastic characteristic, the indenter shaft 104 can be supported by only the folding springs 351. Accordingly, no other mechanism for supporting the indenter shaft 104 is required.

The hardness testing apparatus of the present invention is not limited to this embodiment. For example, the present invention is not limited to the folding spring made of beryllium copper, and material obtaining a non-linear elastic characteristic by shaping may be applicable for the folding spring. Further, the shaping method, the setting of the non-linear elastic characteristic and the like in the folding spring can be appropriately modified without departing from the scope of the invention.

Seventh Embodiment

A hardness testing apparatus 601 of the seventh embodiment will be described in detail with reference to FIGS. 21 to 23.

Figure 21:
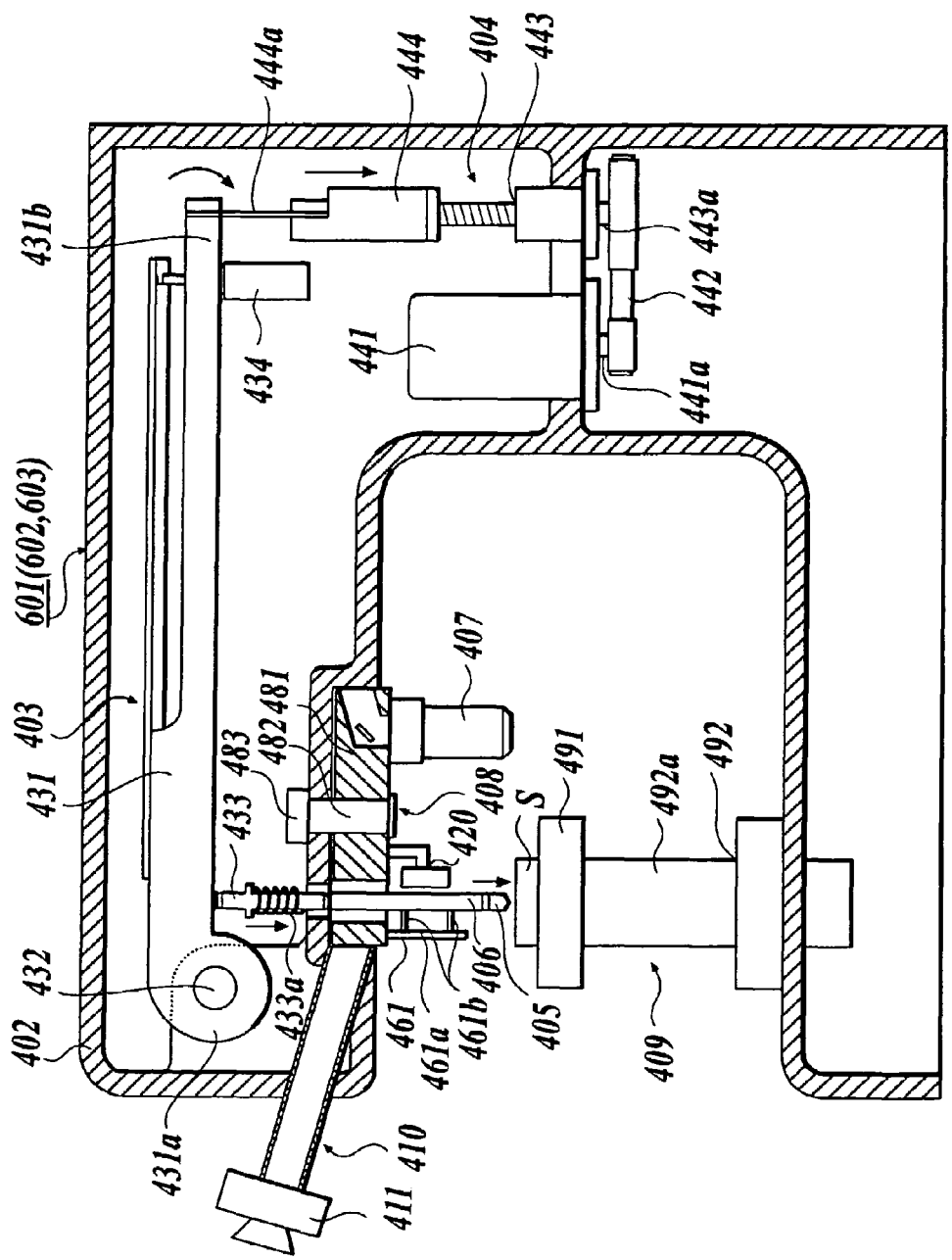
FIG. 21 is a cross sectional view schematically showing a hardness testing apparatus according to the seventh, eighth and ninth embodiments of the present invention.
Figure 22:
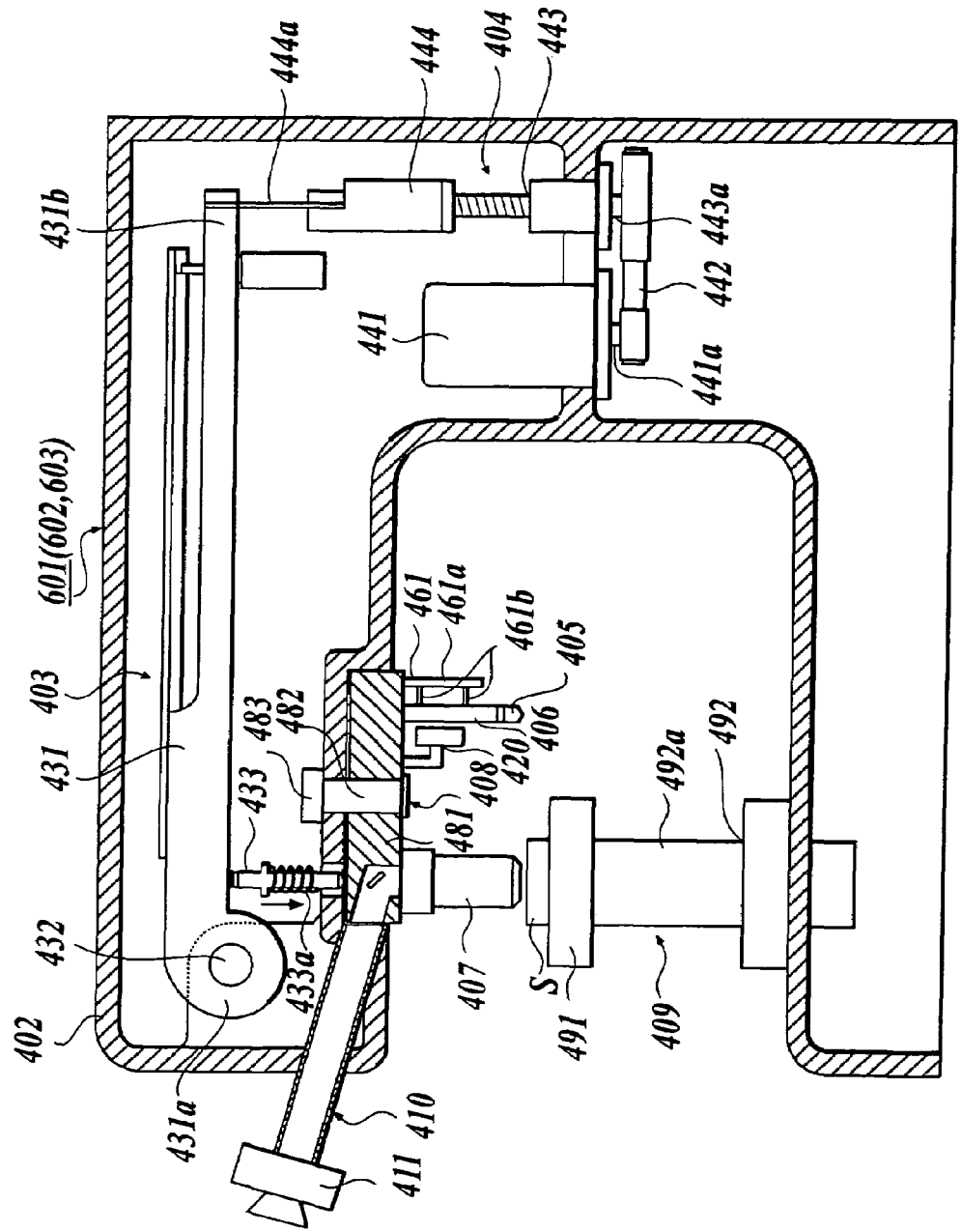
FIG. 22 is a cross sectional view schematically showing the hardness testing apparatus according to the seventh, eighth and ninth embodiments of the present invention.
Figure 23:
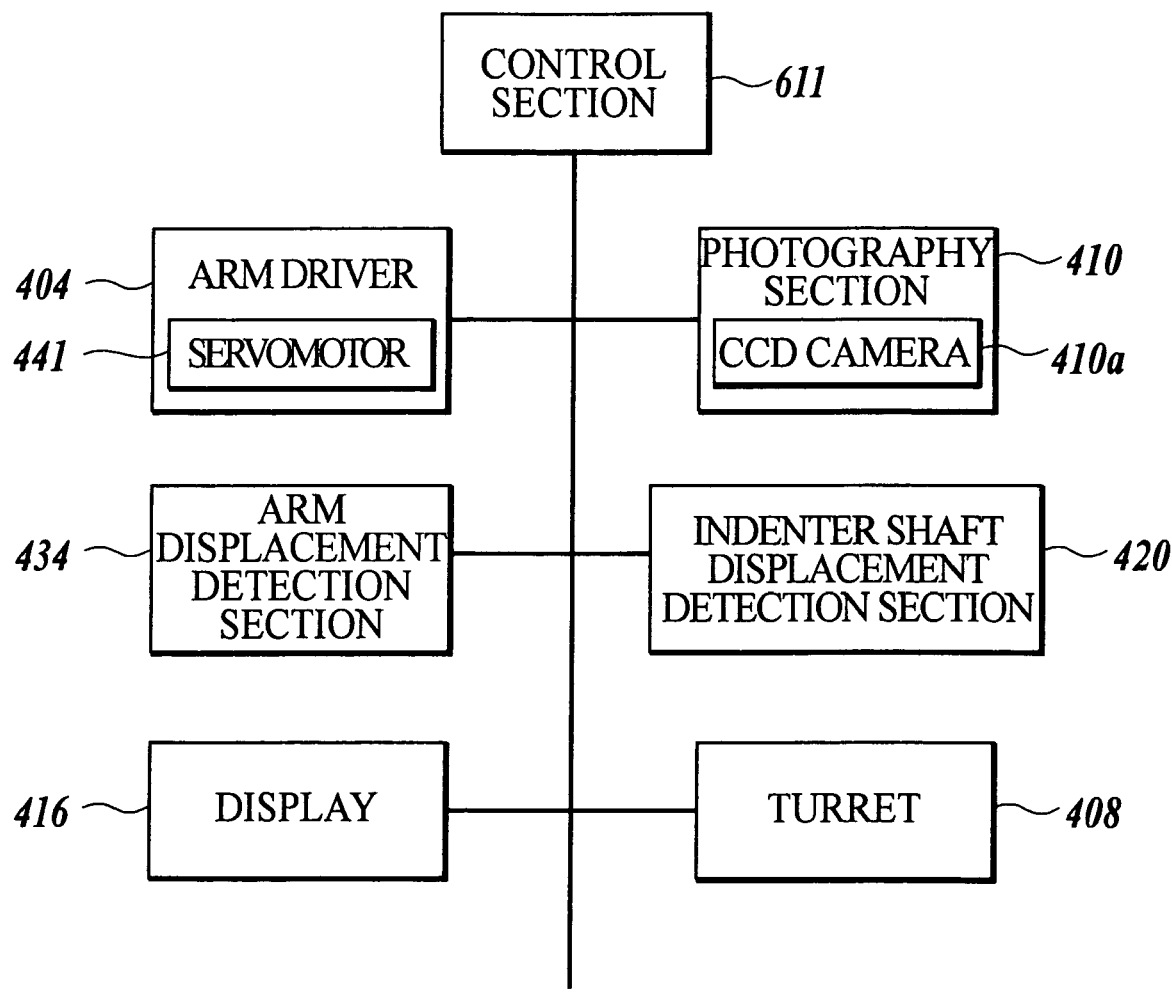
FIG. 23 is a block diagram schematically showing the hardness testing apparatus according to the seventh embodiment of the present invention.

As shown in FIGS. 21 and 22, the hardness testing apparatus 601 comprises a testing apparatus body 402 having constitutional elements of the apparatus 601 in the inside thereof, a loading arm 403 rotatably supported by the testing apparatus body 402, an arm driver 404 acting as a test force applying section for applying a test force to the loading arm 403 and driving the loading arm 403, a turret 408 rotatably arranged below the loading arm 403 in the testing apparatus body 402 and acting as a supporting section, an indenter shaft 406 attached to the turret 408 and having an indenter 405 at the top of the indenter shaft 406, a plurality of objective lenses 407 attached to the turret 408, a sample stand 409 having the sample S mounted thereon and arranged opposite to the turret 408, a photography section 410 for photographing a dimple formed in the sample S on the sample stand 409, and a display 416 for displaying an enlarged image of the dimple. A control section 611 shown in FIG. 23 controls operations of the members of the hardness testing apparatus 601.

The loading arm 403 comprises an arm body 431 and a rotational shaft 432 for rotatably supporting an end 431a of the arm body 431 in the testing apparatus body 402. Another end 431b of the arm body 431 is divided into a first other end 431b and a second other end 431c so as to diverge at the fork. The first other end 431b is formed in plate spring shape and has a warp performance to be able to be warped.

On the lower surface side of the arm body 431, a loading shaft 433 elastically supported by a coil spring 433a is arranged between the lower surface of the arm body 431 and the testing apparatus body 402. In the arm body 431, an arm displacement detection member 434 is arranged to detect an amount of divergence between the first other end 431b and the second other end 431c when the loading arm 403 (arm body 431) is driven.

In the arm body 431, the end 431a of the arm body 431 is rotatably supported by the rotational shaft 432 in the testing apparatus body 402. The arm driver 404 is connected to the first other end 431b and generates an action force for driving the loading arm 403 as a test force. When the arm driver 404 is operated, the arm body 431 is rotationally moved around the rotational shaft 432. When the arm body 431 is rotationally moved downward, the arm body 431 pushes the loading shaft 433 downward and moves the loading shaft 433. The loading shaft 433 transmits the driving and operation of the arm body 431 (loading arm 403) to the indenter shaft 406 (refer to FIG. 21).

For example, the arm displacement detection member 434 comprises a scale having graduations curved at predetermined intervals, and a linear encoder for optically reading the graduations of the scale. When the arm body 431 is rotationally moved to make the indenter 405 push into the sample S through the indenter shaft 406, the arm displacement detection member 434 detects an amount of divergence (amount of spring displacement) between the first other end 431b and the second other end 431c and outputs an arm displacement signal based on the detected amount of divergence to the control section 611. The amount of divergence (amount of spring displacement) corresponds to a pushing force (test force) for pushing the sample S by the indenter 405 or a load applied to the sample S.

The arm driver 404 comprises a servomotor 441, a ball screw 443, a timing belt 442 wound on a motor shaft 441a of the servomotor 441 and a screw shaft 443a of the ball screw 443, and a fixed jig 444 held by the ball screw 443. The arm driver 404 is connected to the loading arm 403 by fixing a plate spring 444a of the fixed jig 444 to the first other end 431b of the arm body 431.

The servomotor 441 is driven according to a driving control signal received from the control section 611. The driving force of the motor shaft 441a of the servomotor 441 rotated by the driving of the servomotor 441 is transmitted to the screw shaft 443a of the ball screw 443 through the timing belt 442, and the ball screw 443 is rotated. The fixed jig 444 is vertically moved due to the rotational driving of the ball screw 443.

As described above, the arm driver 404 vertically moves the fixed jig 444 according to the driving of the servomotor 441, transmits the driving (driving force) to the first other end 431b of the arm body 431 connected to the fixed jig 444 and rotationally moves the arm body 431 (loading arm 403). When the arm driver 404 drives the loading arm 403, the plate spring 444a is warped.

The sample stand 409 comprises a sample stage 491 mounting the sample S thereon and a stage lifting member 492 arranged on the lower surface of the sample stage 491. The stage lifting member 492 has a screw 492a, and the sample stage 491 can be vertically moved relatively to the testing apparatus body 402 by rotating the screw 492a.

The turret 408 comprises a turret body 481 and a rotational shaft 482 for rotatably supporting the turret body 481 in the testing apparatus body 402.

In the turret body 481, the indenter shaft 406, the objective lens 407 and an indenter shaft displacement detection member 420 acting as a penetration detection member for detecting an amount of displacement of the indenter shaft 406 are arranged. The indenter shaft 406 is placed in the turret body 481 by using an indenter shaft holder 461. The turret body 481 is connected to a driving motor 483 acting as a driving section. The driving motor 483 is driven by supplying current from the control section 611 to the driving motor 483, and positions of the indenter shaft 406 and the objective lens 407 are changed to other ones by rotating the turret body 481.

The indenter shaft holder 461 comprises a longitudinal holding member 461a and two plate springs 461b laterally extending from the longitudinal holding member 461a. The indenter shaft 406 is elastically supported by the plate springs 461b. The indenter shaft 406 is placed perpendicularly to the sample mounting surface of the sample stage 491, particularly, the surface (upper surface) of the sample S mounted on the sample stage 491.

The indenter 405 is changeably placed at the lower end of the indenter shaft 406.

As shown in FIG. 21, when the turret 408 (turret body 481) is rotated to change the position of the indenter shaft 406 to another position corresponding to the loading shaft 433, the action force for moving the loading shaft 433 downward while rotationally moving the loading arm 403 can be transmitted to the indenter shaft 406, and the indenter 405 can be pushed into the sample S by pressing the indenter 405 to the sample S.

A microscope 411 of the photography section 410 has the objective lens 407. As shown in FIG. 22, when the turret 408 (turret body 481) is rotated to change the position of the objective lens 407 to another position corresponding to the photography section 410, the photography section 410 can photograph the sample S.

The indenter shaft displacement detection member 420, for example, comprises a scale having graduations curved at predetermined intervals, and a linear encoder for optically reading the graduations of the scale. The detection member 420 detects an amount of displacement of the indenter shaft 406 moved to form a dimple in the sample S (that is, an amount of penetration of the indenter 405 pushed into the sample S, depth of the dimple) and outputs an indenter shaft displacement detection signal based on the detected amount of displacement to the control section 611.

The photography section 410 comprises the microscope 411, a charge coupled device (CCD) camera 410a (refer to FIG. 23) attached to the microscope 411 and an illuminating device (not shown) for illuminating an observation position of the sample S. The photography section 410 (CCD camera 410a) photographs the dimple formed on the surface of the sample S and outputs image data of the photographed dimple to the control section 611.

The display 416 is, for example, a liquid crystal monitor or the like and displays the image data of the photographed dimple. Further the display 416 displays the test force at which the indenter 405 is pushed into the surface of the sample S and which is calculated by the control section 611.

The control section 611 comprises arithmetic devices including a central processing unit (CPU), a read only memory (ROM), a random access memory (RAM) and the like. To form a dimple according to predetermined operational conditions (operational conditions of each hardness test) preset to perform a predetermined hardness test, the control section 611 controls operations of the members of the apparatus 601 by executing a predetermined program stored in the ROM.

For example, the control section 611 compares the arm displacement signal received from the arm displacement detection member 434 and preset arm displacement data and outputs a driving control signal to the servomotor 441 to control the arm driver 404 (servomotor 441) for the purpose of rotatably moving the loading arm 403 so as to make the indenter 405 act on the sample S at a predetermined test force (load).

Further, the control section 611 functions as a distance calculation section for calculating distance between predetermined characteristic points of the dimple according to the amount of penetration of the indenter 405 into the sample S detected by the indenter shaft displacement detection member 420.

Moreover, the control section 611 functions as an objective lens selection section for selecting an objective lens 407, which is optimum to display an enlarged image of the dimple, from the plurality of objective lenses 407 held by the turret 408 according to the calculated distance between the predetermined characteristic points of the dimple. The selection criterion of an objective lens 407 is that the objective lens 407 capable of displaying the dimple at the largest image on the display 416 is optimum.

Furthermore, the control section 611 functions as a driving control section for controlling the driving motor 483 connected to the turret 408 to move the indenter shaft 406 after the formation of the dimple and to move the selected objective lens 407 above the dimple.

Next, a hardness testing method using the hardness testing apparatus 601 will be described.

The indenter 405 is initially attached to the indenter shaft 406, the sample S is mounted on the sample stand 409, and the turret 408 and the sample stand 409 are adjusted.

Thereafter, the control section 611 drives the arm driver 404 to rotationally move the loading arm 403 downward and to move the indenter shaft 406 downward through the loading shaft 433. Therefore, the indenter 405 attached to the top of the indenter shaft 406 is pushed into the sample S, and a dimple having an almost rectangular shape is formed in the sample S.

After the formation of the dimple in the sample S, the control section 611 controls the indenter shaft displacement detection member 420 to detect an amount of penetration of the indenter 405 into the sample S, that is, depth of the dimple. Thereafter, the control section 611 calculates length of a diagonal line of the dimple from the detected depth of the dimple. In the calculation of the length of the diagonal line of the dimple, a relational formula indicating the relation between the depth of the dimple and the length of the diagonal line is used.

After the calculation of the length of the diagonal line of the dimple, the control section 611 selects the objective lens 407 optimum to the size of the dimple. In the selection of the objective lens 407, the objective lens 407 having a magnification, at which the image of the dimple is enlarged at superior visibility without deforming the image of the dimple to display the enlarged image on the display 416 of the hardness testing apparatus 601, is selected.

Thereafter, the control section 611 controls the driving motor 483 to rotate the turret 408, and the position of the selected objective lens 407 shown in FIG. 22 is changed to a position of the dimple observation, that is, a position corresponding to the photography section 410. Thereafter, the photography section 410 photographs the dimple formed in the sample S and outputs image data of the photographed dimple to the control section 611, and the control section 611 displays the image of the dimple on the display 416.

In the hardness testing apparatus 601 of this embodiment, when the arm driver 404 applies the test force to the indenter 405, the indenter 405 is pushed into the sample S, and the dimple is formed in the sample S. At this time, the indenter shaft displacement detection member 420 detects the amount of penetration of the indenter 405 into the sample S, and the control section 611 calculates the length of the diagonal line of the dimple according to the detected amount of penetration. The control section 611 selects the optimum objective lens 407 from the plurality of objective lenses 407 according to the length of the diagonal line of the dimple and rotates the turret 408 to move the selected objective lens 407 above the dimple. That is, though the selection of the objective lens 407 based on the dimple is performed by user's experience in the earlier development, the hardness testing apparatus 601 automatically performs the selection of the objective lens 407.

Accordingly, because the user using the hardness testing apparatus 601 to perform the hardness test is not required to select the objective lens 407 by user's experience or knowledge and is not required to set the objective lens corresponding to the dimple by himself or herself, even a person insufficiently skilled in the hardness test can easily perform the hardness test.

Further, because the control section 611 selects the objective lens 407 corresponding to the display of the largest image of the dimple on the display 416, the user can easily grasp features of the dimple.

Eighth Embodiment

First, an example that a hardness testing apparatus 602 of the eighth embodiment automatically selects one objective lens 407 according to information relating to size of a dimple will be described. The constituent elements indicated by the same reference numerals as those in the seventh embodiment are the same as those in the seventh embodiment. Therefore, the description of the constituent elements is omitted.

Figure 24:
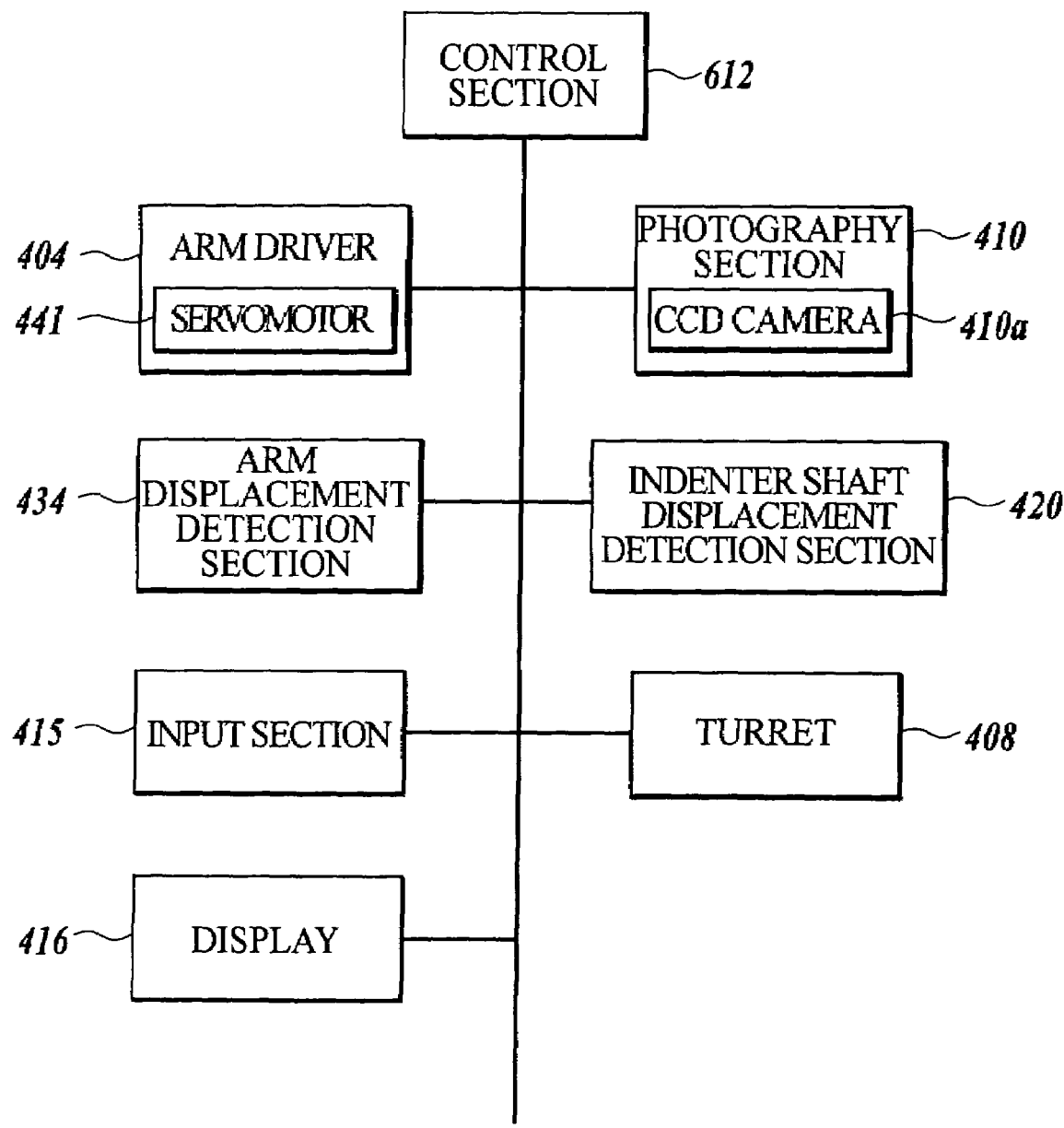
FIG. 24 is a block diagram schematically showing the hardness testing apparatus according to the eighth and ninth embodiments of the present invention.

As shown in FIGS. 21, 22 and 24, the hardness testing apparatus 602 comprises the testing apparatus body 402, the loading arm 403, the arm driver 404, the turret 408, the indenter shaft 406, the objective lens 407, the sample stand 409, the photography section 410, the display 416, the indenter shaft displacement detection member 420, the arm displacement detection member 434 and an input section 415 for receiving information relating to a hardness of the sample S and/or size of a dimple. A control section 612 shown in FIG. 24 controls operations of the members of the hardness testing apparatus 602.

The input section 415 is, for example, a keyboard or a mouse. The input section 415 functions as an assumed hardness input section for receiving a hardness of the sample S assumed by the user and functions as a dimple information input section for receiving information relating to size of the dimple.

The control section 612 functions as the driving control section in the same manner as sin the control section 611 and functions as an objective lens selection section for selecting the objective lens 407 to be used for observation of the dimple according to information relating to size of the dimple received in the input section 415.

Further, the control section 612 functions as a test force calculation section for calculating a test force, at which the indenter 405 is pushed to the surface of the sample S, according to both the hardness of the sample S received in the input section 415 and the objective lens 407 selected by the control section 612.

Next, a hardness testing method using the hardness testing apparatus 602 will be described.

The indenter 405 is initially attached to the indenter shaft 406, the sample S is mounted on the sample stand 409, and the turret 408 and the sample stand 409 are adjusted.

Thereafter, the user assumes a hardness of the sample S for a hardness test and inputs the assumed hardness to the input section 415. Further, the user inputs conditions (for example, a condition for observing the dimple with high accuracy, a condition for observing inside of the sample S at top priority and the like) relating to size of a dimple to the input section 415. The control section 612 selects one objective lens 407 optimum to the observation of the dimple according to the input information relating to the size of the dimple.

Thereafter, the control section 612 calculates a test force according to the input hardness of the sample S and a magnification of the selected objective lens 407. In the calculation of the test force, a relational formula, a table or the like indicating the relation among the hardness of the sample S, the magnification of the objective lens 407 and the test force is used.

After the calculation of the test force, the control section 612 drives the arm driver 404 to rotationally move the loading arm 403 downward and to move downward the indenter shaft 406 through the loading shaft 433. The indenter 405 attached to the top of the indenter shaft 406 is pushed into the sample S at the calculated test force, and a dimple formed in almost rectangular shape is formed in the sample S.

Thereafter, the control section 612 controls the driving motor 483 to rotate the turret 408, and the position of the selected objective lens 407 is changed to a position of the dimple observation, that is, a position corresponding to the photography section 410, as shown in FIG. 22. Thereafter, the photography section 410 photographs the dimple formed in the sample S and outputs image data of the photographed dimple to the control section 612, and the control section 612 displays the image of the dimple on the display 416.

In the hardness testing apparatus 602 of the eighth embodiment, the user inputs the assumed hardness of the sample S and information relating to the size of the dimple to the input section 415. The control section 612 selects one objective lens 407 used for the observation of the dimple according to the information relating to the size of the dimple received in the input section 415. Further, the control section 612 calculates the test force, at which the indenter 405 is pushed to the surface of the sample S, according to the hardness of the sample S received in the input section 415 and the objective lens 407 selected by the control section 612. After the formation of the dimple, the control section 612 moves the indenter 405 and controls the driving motor 483 to move the selected optimum objective lens 407 above the dimple.

Therefore, when the user inputs only the hardness of the sample S for the hardness test, the hardness testing apparatus 602 selects the objective lens 407 used for observation and calculates the test force required for the formation of the sample. Accordingly, the user is not required to set the test force by user's experience performed in the earlier, development, and an accurate test force corresponding to the hardness of the sample S assumed by the user can be set.

Further, because the display 416 displays the test force calculated by the control section 612, the test force can be visually notified to the user. Accordingly, the hardness test can be easily performed, and the test force can be conveniently recorded.

Ninth Embodiment

Next, an example that a user manually selects and inputs one objective lens 407 will be described. In the ninth embodiment, only points different from those in the eight embodiment are described, and the description common to the eighth embodiment is omitted while using the same reference numerals as those in the eighth embodiment.

In a hardness testing apparatus 603 of the ninth embodiment, the input section 415 functions as an objective lens selection section for making a user select one objective lens 407 to be used for observation of the dimple. The control section 612 functions as a recognition section for recognizing a magnification of the selected objective lens 407. Further, the control section 612 functions as a test force calculation section for calculating a test force, at which the indenter 405 is pushed into the surface of the sample S, according to both the hardness of the sample S received in the input section 415 and the magnification of the objective lens 407 recognized by the control section 612.

Next, a hardness testing method using the hardness testing apparatus 603 will be described.

The indenter 405 is initially attached to the indenter shaft 406, the sample S is mounted on the sample stand 409, and the turret 408 and the sample stand 409 are adjusted.

Thereafter, the user assumes a hardness of the sample S for a hardness test and inputs the hardness to the input section 415. Further, the user inputs one objective lens 407 to be used for observation of the dimple to the input section 415. The control section 612 recognizes a magnification of the input objective lens 407 and calculates a test force according to the input hardness of the sample S and the recognized magnification of the objective lens 407. In the calculation of the test force, a relational formula, a table or the like indicating the relation among the hardness of the sample S, the magnification of the objective lens 407 and the test force is used.

After the calculation of the test force, the control section 612 drives the arm driver 404 to rationally move the loading arm 403 downward and to move downward the indenter shaft 406 through the loading shaft 433. The indenter 405 attached to the top of the indenter shaft 406 is pushed into the sample S at the calculated test force, and a dimple formed in almost rectangular shape is formed in the sample S.

Thereafter, the control section 612 controls the driving motor 483 to rotate the turret 408, and the position of the selected objective lens 407 is changed to a position of the dimple observation, that is, a position corresponding to the photography section 410, as shown in FIG. 22. Thereafter, the photography section 410 photographs the dimple formed in the sample S and outputs image data of the photographed dimple to the control section 612, and the control section 612 displays the image of the dimple on the display 416.

In the hardness testing apparatus 603 of the ninth embodiment, the user inputs the hardness of the sample S assumed by the user to the input section 415, and the user selects and inputs one objective lens 407 to be used for the observation of the dimple to the input section 415. The control section 612 recognizes a magnification of the input objective lens 407 and calculates a test force, at which the indenter 405 is pushed to the surface of the sample S, according to the input hardness of the sample S and the recognized magnification of the objective lens 407. After the formation of a dimple, the control section 612 moves the indenter 405 and controls the driving motor 483 to move the selected optimum objective lens 407 above the dimple.

Therefore, when the user inputs the hardness of the sample S for the hardness test and selects one objective lens 407 to be used for the observation of the dimple, the hardness testing apparatus 603 calculates a test force required for the formation of the sample. Accordingly, the user is not required to set the test force performed by user's experience in the earlier development, and an accurate test force corresponding to the hardness of the sample S assumed by the user can be set.

Further, because the display 416 displays the test force calculated by the control section 612, the test force can be visually notified to the user. Accordingly, the hardness test can be easily performed, and the test force can be conveniently recorded.

The hardness testing apparatus according to this invention is not limited to the seventh, eighth and ninth embodiments. In these embodiments, when the optimum objective lens 407 is selected, the selected objective lens 407 is automatically placed above the sample S by rotating the turret 408. However, a speaker (not shown) or the display 416 acting as a notification section may notify the user of the selected objective lens 407 indicated by voice or sound output from the speaker or an image displayed on the display 416. The speaker and the display 416 acting as the notification section may be arranged. The invention can be appropriately modified without departing from the scope of the invention.

The entire disclosure of Japanese Patent Application No. Tokugan 2003-17427 filed on Jan. 27, 2003 including specification, claims, drawings and summary, Japanese Patent Application No. Tokugan 2003-41062 filed on Feb. 19, 2003 including specification, claims, drawings and summary, Japanese Patent Application No. Tokugan 2002-374670 filed on Dec. 25, 2002 including specification, claims, drawings and summary, Japanese Patent Application No. Tokugan 2003-298764 filed on Aug. 22, 2003 including specification, claims, drawings and summary, Japanese Patent Application No.

Tokugan 2003-361881 filed on Oct. 22, 2003 including specification, claims, drawings and summary, Japanese Patent Application No. Tokugan 2003-350747 filed on Oct. 9, 2003 including specification, claims, drawings and summary and Japanese Patent Application No. Tokugan 2003-350796 filed on Oct. 9, 2003 including specification, claims, drawings and summary are incorporated herein by reference in its entirety.

What is claimed is:

1. A hardness testing apparatus, which has a test force applying section for applying a predetermined test force at which an indenter is pushed into a surface of a sample, and a plurality of object lenses to display an enlarged image of a dimple formed on the surface of the sample by the indenter on a display and measures a hardness of the sample according to the dimple, comprising:
    a hardness input section to receive an assumed hardness of the sample assumed by a user;
    a dimple information input section for receiving information relating to a size of the dimple from the user;
    an objective lens selection section for selecting one objective lens to be used for observation of the dimple according to the information relating to the size of the dimple inputted using the dimple information input section; and
    a test force calculation section for calculating a test force, at which the indenter is pushed into the surface of the sample, according to the hardness of the sample inputted by the hardness input section and a magnification of the objective lens selected by the objective lens selection section.

2. The hardness testing apparatus as claimed in claim 1; wherein the display displays the test force calculated by the test force calculation section.

3. The hardness testing apparatus as claimed in claim 1; further comprising:
    a supporting section for supporting the indenter and the objective lenses;
    a driving section for driving the supporting section to make the indenter and the objective lenses be movable; and
    a driving control section for controlling the driving section to move the indenter after formation of the dimple and to move the objective lens selected by the objective lens selection section above the dimple.

4. A hardness testing apparatus, which has a test force applying section for applying a predetermined test force at which an indenter is pushed into a surface of a sample, and a plurality of object lenses to display an enlarged image of a dimple formed on the surface of the sample by the indenter on a display and measures a hardness of the sample according to the dimple, comprising:
    a hardness input section to receive an assumed hardness of the sample assumed by a user;
    an objective lens selection section for making the user select one objective lens to be used for observation of the dimple;
    a recognition section for recognizing a magnification of the objective lens selected in the objective lens selection section; and
    a test force calculation section for calculating a test force, at which the indenter is pushed into the surface of the sample, according to the hardness of the sample inputted by the hardness input section and the magnification of the objective lens recognized by the recognition section.

5. The hardness testing apparatus as claimed in claim 4; wherein the display displays the test force calculated by the test force calculation section.

6. The hardness testing apparatus as claimed in claim 4; further comprising:
    a supporting section for supporting the indenter and the objective lenses;
    a driving section for driving the supporting section to make the indenter and the objective lenses be movable; and
    a driving control section for controlling the driving section to move the indenter after formation of the dimple and to move the objective lens selected by the objective lens selection section above the dimple.

* * * * *